(12) United States Patent
Ishino et al.

(10) Patent No.: US 12,163,158 B2
(45) Date of Patent: Dec. 10, 2024

(54) ORGANOID AND METHOD FOR PRODUCING SAME

(71) Applicants: Fumitoshi Ishino, Tokyo (JP); Jiyoung Lee, Tokyo (JP)

(72) Inventors: Fumitoshi Ishino, Tokyo (JP); Jiyoung Lee, Tokyo (JP)

(73) Assignees: Fumitoshi Ishino, Tokyo (JP); Jiyoung Lee, Tokyo (JP)

( * ) Notice: Subject to any disclaimer, the term of this patent is extended or adjusted under 35 U.S.C. 154(b) by 429 days.

(21) Appl. No.: 16/644,677

(22) PCT Filed: Sep. 28, 2018

(86) PCT No.: PCT/JP2018/036538
§ 371 (c)(1),
(2) Date: May 21, 2020

(87) PCT Pub. No.: WO2019/066059
PCT Pub. Date: Apr. 4, 2019

(65) Prior Publication Data
US 2020/0283735 A1    Sep. 10, 2020

(30) Foreign Application Priority Data

Sep. 29, 2017  (JP) .................... 2017-190950

(51) Int. Cl.
*C12N 5/071* (2010.01)
*C12N 5/077* (2010.01)
*G01N 33/50* (2006.01)

(52) U.S. Cl.
CPC ......... *C12N 5/0697* (2013.01); *C12N 5/0657* (2013.01); *C12N 5/0688* (2013.01); *G01N 33/5014* (2013.01); *C12N 2501/113* (2013.01); *C12N 2501/115* (2013.01); *C12N 2501/155* (2013.01); *C12N 2501/235* (2013.01); *C12N 2506/03* (2013.01); *C12N 2533/52* (2013.01)

(58) Field of Classification Search
CPC ............... C12N 5/0697; C12N 5/0657; C12N 5/0688; C12N 2501/113; C12N 2501/115; C12N 2501/155; C12N 2501/235; C12N 2506/03; C12N 2533/52; G01N 33/5014
See application file for complete search history.

(56) References Cited

U.S. PATENT DOCUMENTS

| | | |
|---|---|---|
| 2016/0348070 A1 | 12/2016 | Kirkeby et al. |
| 2017/0002330 A1 | 1/2017 | Vunjak-Novakovic et al. |
| 2017/0275592 A1 | 9/2017 | Sachs et al. |
| 2018/0030409 A1 | 2/2018 | Lewis et al. |
| 2019/0153391 A1 | 5/2019 | Ochi et al. |

FOREIGN PATENT DOCUMENTS

| | | |
|---|---|---|
| WO | 2005/017131 A2 | 2/2005 |
| WO | 2016/043168 A1 | 3/2016 |
| WO | 2016/141137 A1 | 9/2016 |
| WO | 2016/162747 A2 | 10/2016 |

OTHER PUBLICATIONS

Otsuki et al. Effective embryoid body formation from induced pluripotent stem cells for regeneration of respiratory epithelium, Laryngoscope, 124: E8-E14. (Year: 2014).*
Rosenblatt-Velin et al., FGF-2 controls the differentiation of resident cardiac precursors into functional cardiomyocytes, The Journal of Clinical Investigation, 115(7): 1724-1733. (Year: 2005).*
Kadari et al., Robust generation of cardiomyocytes from human iPS cells requires precise modulation of BMP and WNT signaling, Stem Cell Reviews and Reports., 11: 560-569. (Year: 2015).*
Wei et al., Embryonic stem cells and cardiomyocyte differentiation: phenotypic and molecular analyses, Journal of Cellular and Molecular Medicine, 9(4): 804-817. (Year: 2005).*
Braam, et l., Inhibition of ROCK improves survival of human embryonic stem cell-derived cardiomyocytes after dissociation, Annals of the New York Academy of Sciences, 1188: 52-57 (Year: 2010).*
Khademhosseini et al., Microfluidic patterning for fabrication of contractile cardiac organoids, Biomedical Microdevices, 9:149-157. (Year: 2007).*
Simian et al., Organoids: a historical perspective of thinking in three dimension, Journal of Cell Biology, 216(1): 31-40, published online Dec. 28, 2016. (Year: 2017).*
Lonza EGM-2 media, data sheet, retrieved from the internet Dec. 15, 2022. (Year: 2022).*
Lonza, FGM-3 media, data sheet, retrieved from the internet Dec. 15, 2022. (Year: 2022).*
Takei et al. (Bone morphogenetic protein-4 promotes induction of cardiomyocytes from human embryonic stem cells in serum-based embryoid body development, Am J Physiol Heart Circ Physiol 296: H1793-H1803. (Year: 2009).*
Richards et al., Inspiration from heart development: Biomimetic development of functional human cardiac organoids, Biomaterials, 142: 112-123 and Supplementary Figures, S1-S12. (Year: 2017).*
Lough et al., Combined BMP-2 and FGF-4, but Neither Factor Alone, Induces Cardiogenesis in Non-Precardiac Embryonic Mesoderm, Developmental Biology, 178: 198-202. (Year: 1996).*
Yamada et al., Laminin-111-derived peptide-hyaluronate hydrogels as a synthetic basement membrane, Biomaterials 34: 6539-6547. (Year: 2013).*
Zhou et al., Embryoid bodies formation and differentiation from mouse embryonic stem cells in collagen/Matrigel scaffolds, Journal of Genetics and Genomics, 37: 451-460. (Year: 2010).*
Zhu et al., Evidence that Fibroblast Growth Factors 1 and 4 Participate in Regulation of Cardiogenesis, Developmental Dynamics 207: 429-438. (Year: 1996).*
Mohr et al., The microwell control of embryoid body size in order to regulate cardiac differentiation of human embryonic stem cells, Biomaterials, 31: 1885-1893. (Year: 2010).*

(Continued)

*Primary Examiner* — Arthur S Leonard
*Assistant Examiner* — Joseph Paul Miano
(74) *Attorney, Agent, or Firm* — Sughrue Mion, PLLC

(57) ABSTRACT

The present invention provides a method for producing a heart organoid and/or a lung organoid, comprising the step of: culturing an embryoid body in the presence of an FGF protein on a surface of a gel containing an extracellular matrix constituent protein.

3 Claims, 52 Drawing Sheets

(56) References Cited

OTHER PUBLICATIONS

Dylan J. Richards et al., "Inspiration from heart development: Biomimetic development of functional human cardiac organoids", Biomaterials, Jul. 12, 2017, pp. 112-123, vol. 142.

Artem Shkumatov et al., "Matrix Rigidity-Modulated Cardiovascular Organoid Formation from Embryoid Bodies", Plos One, Apr. 2014, vol. 9, Issue 4, e94764, pp. 1-10.

Steven J. Kattman et al., "Multipotent Flk-1+ Cardiovascular Progenitor Cells Give Rise to the Cardiomyocyte, Endothelial, and Vascular Smooth Muscle Lineages", Developmental Cell, Nov. 2006, pp. 723-732, vol. 11.

Steven J. Kattman et al., "Stage-Specific Optimization of Activin/Nodal and BMP Signaling Promotes Cardiac Differentiation of Mouse and Human Pluripotent Stem Cell Lines", Cell Stem Cell, Feb. 4, 2011, pp. 228-240, vol. 8.

Alessandra Moretti et al., "Multipotent Embryonic Isl1+ Progenitor Cells Lead to Cardiac, Smooth Muscle, and Endothelial Cell Diversification", Cell, Dec. 15, 2006, pp. 1151-1165, vol. 127.

Christina Mauritz et al., "Generation of Functional Murine Cardiac Myocytes From Induced Pluripotent Stem Cells", Circulation, Molecular Cardiology, Jul. 29, 2008, pp. 507-517.

Valerie Kouskoff et al., "Sequential development of hematopoietic and cardiac mesoderm during embryonic stem cell differentiation", PNAS, Sep. 13, 2005, pp. 13170-13175, vol. 102, No. 37.

Hans Jorg Fehling et al., "Tracking mesoderm induction and its specification to the hemangioblast during embryonic stem cell differentiation", Development, 2003, vol. 130, pp. 4217-4227.

Genta Narazaki et al., "Directed and Systematic Differentiation of Cardiovascular Cells from Mouse Induced Pluripotent Stem Cells", Circulation, Molecular Cardiology, Jul. 29, 2008, pp. 498-506.

Jun K. Yamashita et al., "Prospective identification of cardiac progenitors by a novel single cell-based cardiomyocyte induction", The FASEB Journal, Jul. 20, 2005, pp. 1-29.

Jianhua Zhang et al., "Extracellular Matrix Promotes Highly Efficient Cardiac Differentiation of Human Pluripotent Stem Cells: The Matrix Sandwich Method", *Circ Res.*, Oct. 12, 2012, pp. 1125-1136, vol. 111, No. 9.

Meritxell Huch et al., "Modeling mouse and human development using organoid cultures", Development, 2015, pp. 3113-3125, vol. 142.

Taka-Aki K. Noguchi et al., "Generation of stomach tissue from mouse embryonic stem cells", Nature Cell Biology, Aug. 2015, pp. 984-993, vol. 17, No. 8.

International Search Report for PCT/JP2018/036538 dated Nov. 13, 2018 [PCT/ISA/210].

Dye et al., "In vitro generation of human pluripotent stem cell derived lung organoids", eLife, 2015, vol. 4, pp. 1-25 (25 pages total).

Extended European Search Report, dated Jun. 4, 2021, issued by the European Patent Office in European Application No. 18860752.7.

Di Napoli, et al. " Simvastatin reduces reperfusion injury by modulating nitric oxide synthase expression: an ex vivo study in isolated working rat hearts", Cardiovascular Research, Apr. 4, 2001, vol. 51, pp. 283-293 (11 pages).

Neuhaus, et al. "Assessment of long-term cultivated human precision-cut lung slices as an ex vivo system for evaluation of chronic cytotoxicity and functionality", Journal of Occupational Medicine and Toxicology, 2017, vol. 12, No. 13, pp. 1-8 (8 pages).

Communication dated Apr. 29, 2024 in European Application No. 18 860 752.7.

* cited by examiner

ORGANOID AND METHOD FOR PRODUCING SAME

CROSS REFERENCE TO RELATED APPLICATIONS

This application is a National Stage of International Application No. PCT/JP2018/036538, filed Sep. 28, 2018, claiming priority based on Japanese Patent Application No. 2017-190950, filed Sep. 29, 2017.

TECHNICAL FIELD

The present invention relates to an organoid and a method for producing the same. The present invention particularly relates to a method for producing heart organoids and/or lung organoids, and to heart organoids, lung organoids, or fragments or cells of these organoids produced by the method. The present invention also relates to a kit used for the production method. Moreover, the present invention relates to a method for evaluating the toxicity of a compound to the organ using the heart organoids or the lung organoids, and a method for evaluating a therapeutic activity of a compound on a disease relating to the organ.

BACKGROUND ART

The heart is a vital organ which is responsible for blood circulation by rhythmic contraction, sustaining the life of an animal. Since this organ is composed of various types of cells such as endothelial cells, cardiomyocytes, and smooth muscle cells, and enables rhythmic contraction, these groups of cells having different functions and morphologies are delicately and elaborately arranged in the heart during their development process.

In the development of the heart, first, a cardiac crescent including a first heart field and a second heart field is formed. Then, the cells on both the left and right sides are fused to form a heart tube having a tubular shape. Then, this heart tube loops to form a looping heart tube, and further, an atrial chamber and a ventricular chamber are generated. In addition, following these processes in which the cells differentiate and cooperate into ones that have various functions, the heart is completed as a cooperative and functional organ while having a complicated three-dimensional structure.

Various methods have been developed to reproduce such differentiation induction into the heart in vitro. A method for inducing differentiation of pluripotent stem cells (iPS cells, ES cells) into cells of the heart system in vitro, a method for producing various types of cardiac cells through embryoid body (EB) derived cardiac progenitor cells under monolayer culture conditions, a method for inducing cardiac progenitor cells from somatic cells by cell lineage-specific direct reprogramming, and the like (PTL 1 and NPLs 1 to 9) have been reported.

As described above, a variety of methods for inducing differentiation into the heart has made it possible to produce specific types of cardiac cells from pluripotent stem cells. Nevertheless, presumably due to the structural complexity of the heart described above, the production of a functional three-dimensional heart in which different cell groups are delicately and elaborately arranged has not yet been achieved.

In addition, not only the heart but also organs having such a functional three-dimensional structure (such as so-called organoids) are useful in various applications such as regenerative medicine, drug discovery research, and safety testing. For example, in regenerative medicine, it is possible to restore the lost function by transplanting an organ itself that has been induced to differentiate from pluripotent stem cells or the like. In addition, in drug discovery research, analysis and screening of an organ that has been induced to differentiate from patient-derived disease-specific pluripotent stem cells and the like greatly contribute to the development of a new drug for the disease. In addition, the safety testing is usually performed on animal cells. Since the response of a living body to a drug is caused by the interaction of various cells, there is a possibility that the safety of a drug can be analyzed with high accuracy by targeting the organ rather than evaluating the cell alone.

For the above reasons, the method for three dimensionally culturing pluripotent stem cells or adult stem cells has been energetically advanced recently, making it possible to induce in-vitro differentiation into endodermal and ectodermal tissues such as the brain, the stomach, and the intestinal tissues by mimicking organ formation in a living body (NPLs 10 and 11).

However, as described above, a method for inducing differentiation of a functional heart or the like having a three-dimensional structure has not yet been developed.

CITATION LIST

Patent Literature

[PTL 1] International Publication No. WO2016/043168

Non Patent Literature

[NPL 1] Kattman, S. J. et al., Dev Cell 11, 723-732, doi: 10.1016/j.devcel.2006.10.002 (2006).
[NPL 2] Kattman, S. J. et al., Cell Stem Cell 8, 228-240, doi: 10.1016/j.stem.2010.12.008 (2011).
[NPL 3] Moretti, A. et al., Cell 127, 1151-1165, doi: 10.1016/j.cell.2006.10.029 (2006).
[NPL 4] Mauritz, C. et al., Circulation 118, 507-517, doi: 10.1161/CIRCULATIONAHA.108.778795 (2008).
[NPL 5] Kouskoff, V. et al., Proc Natl Acad Sci USA 102, 13170-13175, doi: 10.1073/pnas.0501672102 (2005).
[NPL 6] Fehling, H. J. et al., Development 130, 4217-4227, doi: 10.1242/dev.00589 (2003).
[NPL 7] Narazaki, G. et al., Circulation 118, 498-506, doi: 10.1161/CIRCULATIONAHA.108.769562 (2008).
[NPL 8] Yamashita, J. K. et al., FASEB J 19, 1534-1536, doi: 10.1096/fj.04-3540fje (2005).
[NPL 9] Zhang J. et al., Circ Res. 111 (9), 1125-36.doi: 10.1161/CIRCRESAHA.112.273144 (2012).
[NPL 10] Huch, M. & Koo, B. K. Development 142, 3113-3125, doi: 10.1242/dev.118570 (2015).
[NPL 11] Noguchi, T. K. et al., Nat Cell Biol 17, 984-993, doi: 10.1038/ncb3200 (2015).

SUMMARY OF INVENTION

Technical Problem

The present invention has been made in view of the above-described problems of the related art, and aims to provide a functional organoid such as a heart organoid having a three-dimensional structure, and a method for producing the same.

Solution to Problem

The present inventors have made earnest studies to achieve the above object, and have made it clear as a result that a heart organoid having a three-dimensional structure is formed by culturing an embryoid body derived from mouse ES cells in the presence of fibroblast growth factor (FGF) on the surface of a complex composed of laminin or laminin and entactin constituting an extracellular matrix.

In addition, the present inventors have also made it clear that that the obtained heart organoid exhibits various types of cell markers in a region-specific manner, such as platelet/endothelial cell adhesion molecule-1 (PECAM)/CD31 which is a marker of vascular endothelial cells, α-smooth muscle actin (αSMA) and smooth muscle myosin heavy chain (SM-MHC) which are markers of smooth muscle, and Nkx2-5 and cardiac troponin I which are markers of cardiac muscle. Moreover, in heart organoids, expression of Mlc2v, which is a marker of mature ventricles, was also observed with regionality.

In addition, the present inventors have made it clear by calcium kinetic analysis that self-beating-like calcium influx, which indicates myocardial contraction indicative of the functioning of the heart, occurs in the obtained heart organoids.

The present inventors have further clarified that the above method makes it possible to produce heart organoids from human iPS cells via embryoid body formation. What is more, the present inventors have found that the method makes it possible to produce not only heart organoids but also lung organoids. Thus, the present invention has been completed.

Specifically, the present invention relates to a method for producing heart organoids and/or lung organoids, and to heart organoids, lung organoids, or fragments or cells of these organoids produced by the method. The present invention also relates to a kit used for the production method. Moreover, the present invention relates to a method for evaluating the toxicity of a compound to the organ using the heart organoids or the lung organoids, and a method for evaluating a therapeutic activity of a compound on a disease relating to the organ. More specifically, the present invention provides the following.

<1> A method for producing a heart organoid and/or a lung organoid, comprising the step of: culturing an embryoid body in the presence of an FGF protein on a surface of a gel containing an extracellular matrix constituent protein.

<2> The production method according to <1>, further comprising, after the step of culturing in the presence of the FGF protein, culturing in the presence of an FGF protein, a BMP, and an LIP.

<3> The production method according to <1>, further comprising, after the step of culturing in the presence of the FGP protein, culturing in the presence of an FGF protein, a BMP, an LIF, and a GSK-3 inhibitor.

<4> The production method according to <1>, wherein the culturing the embryoid body is culturing the embryoid body on the surface of the gel in the presence of an FGF protein and an Rho-binding kinase inhibitor.

<5> The production method according to any one of <1> to <4>, wherein the extracellular matrix constituent protein is a protein containing at least one selected from the group consisting of laminin and entactin.

<6> The production method according to any one of <1> to <5>, wherein the extracellular matrix constituent protein is a protein containing no collagen or proteoglycan.

<7> The production method according to any one of <1> to <6>, wherein the embryoid body is a cell mass obtained by suspension culture of pluripotent stem cells in the 6 absence of an LIF.

<8> A kit for producing a heart organoid and/or a lung organoid, comprising: a solution or gel containing an extracellular matrix constituent protein; an FGF protein; and a medium for culturing an embryoid body.

<9> The kit according to <8>, further comprising at least one selected from the group consisting of a BMP, a GSK-3 inhibitor, an LIP, and an Rho-binding kinase inhibitor.

<10> The kit according to <8> or <9>, wherein the extracellular matrix constituent protein is a protein containing at least one selected from the group consisting of laminin and entactin.

<11> The kit according to any one of <8> to <10>, wherein the extracellular matrix constituent protein is a protein containing no collagen or proteoglycan.

<12> The kit according to any one of <8> to <11>, further comprising an LIF-free medium for transforming pluripotent stem cells into embryoid bodies by suspension culture.

<13> A heart organoid, a lung organoid, or a fragment or cell of these organoids, obtained by culturing an embryoid body in the presence of an FGF protein on a surface of a gel containing an extracellular matrix constituent protein.

<14> The heart organoid, the lung organoid, or the fragment or cell of these organoids according to <13>, used for transplantation into a living body.

<15> The heart organoid, the lung organoid, or the fragment or cell of these organoids according to <13> or <14>, obtained by, after the step of culturing in the presence of the FGF protein, culturing in the presence of an FGF protein, a BMP, and an LIF.

<16> The heart organoid, the lung organoid, or the fragment or cell of these organoids according to <13> or <14>, obtained by, after the step of culturing in the presence of the FGF protein, culturing in the presence of an FGF protein, a BMP, an LIF, and a GSK-3 inhibitor.

<17> The heart organoid, the lung organoid, or the fragment or cell of these organoids according to <13> or <14>, obtained by culturing the embryoid body on the surface of the gel in the presence of an FGF protein and an Rho-binding kinase inhibitor.

<18> The heart organoid, the lung organoid, or the fragment or cell of these organoids according to any one of <13> to <17>, wherein the extracellular matrix constituent protein is a protein containing at least one selected from the group consisting of laminin and entactin.

<19> The heart organoid, the lung organoid, or the fragment or cell of these organoids according to any one of <13> to <18>, wherein the extracellular matrix constituent protein is a protein containing no collagen or proteoglycan.

<20> The heart organoid, the lung organoid, or the fragment or cell of these organoids according to any one of <13> to <18>, wherein the embryoid body is a cell mass obtained by suspension culture of pluripotent stem cells in the absence of an LIF.

<21> The heart organoid, the lung organoid, or the fragment or cell of these organoids according to <20>, wherein the pluripotent stem cells are pluripotent stem cells derived from a patient suffering from a heart disease or a lung disease.

<22> A method for evaluating toxicity of a compound to a heart, comprising the steps of:
  bringing the heart organoid according to any one of <13> to <21> into contact with a test compound to detect a condition of the heart organoid; and
  judging that the test compound is a compound having toxicity to the heart if deterioration is observed in the condition detected in the previous step.
<23> A method for evaluating therapeutic activity of a compound on a heart disease, comprising the steps of:
  bringing the heart organoid according to any one of <13> to <21> exhibiting a heart disease into contact with a test compound to detect a condition of the heart organoid; and
  judging that the test compound is a compound having therapeutic activity on the heart disease if a therapeutic effect on the heart disease is observed in the condition detected in the previous step.
<24> A method for evaluating toxicity of a compound to a lung, comprising the steps of:
  bringing the lung organoid according to any one of <13> to <21> into contact with a test compound to detect a condition of the lung organoid; and
  judging that the test compound is a compound having toxicity to the lung if deterioration is observed in the condition detected in the previous step.
<25> A method for evaluating therapeutic activity of a compound on a lung disease, comprising the steps of:
  bringing the lung organoid according to any one of <13> to <21> exhibiting a lung disease into contact with a test compound to detect a condition of the lung organoid; and
  judging that the test compound is a compound having therapeutic activity on the lung disease if a therapeutic effect on the lung disease is observed in the condition detected in the previous step.

Advantageous Effects of Invention

The present invention makes it possible to provide a functional heart organoid and lung organoid having a three-dimensional structure. In particular, a heart organoid and a lung organoid can be produced without requiring a complicated differentiation induction method adapted to each of the various types of cells constituting these organs (in the heart, endothelial cells, cardiomyocytes, smooth muscle cells, and the like, and in the lung, alveoli cells and the like).

Moreover, in the heart organoid of the present invention, the regionality of various cells faithfully reproduces that in a living body, and also exerts functions such as myocardial contraction. In addition, the lung organoid of the present invention also has alveoli, which are an important structure for exerting its function. Therefore, the use of the organoids of the present invention makes it possible to evaluate the toxicity of a compound to the corresponding organs and the therapeutic activity of a compound on diseases related to the organs.

Figure 14:
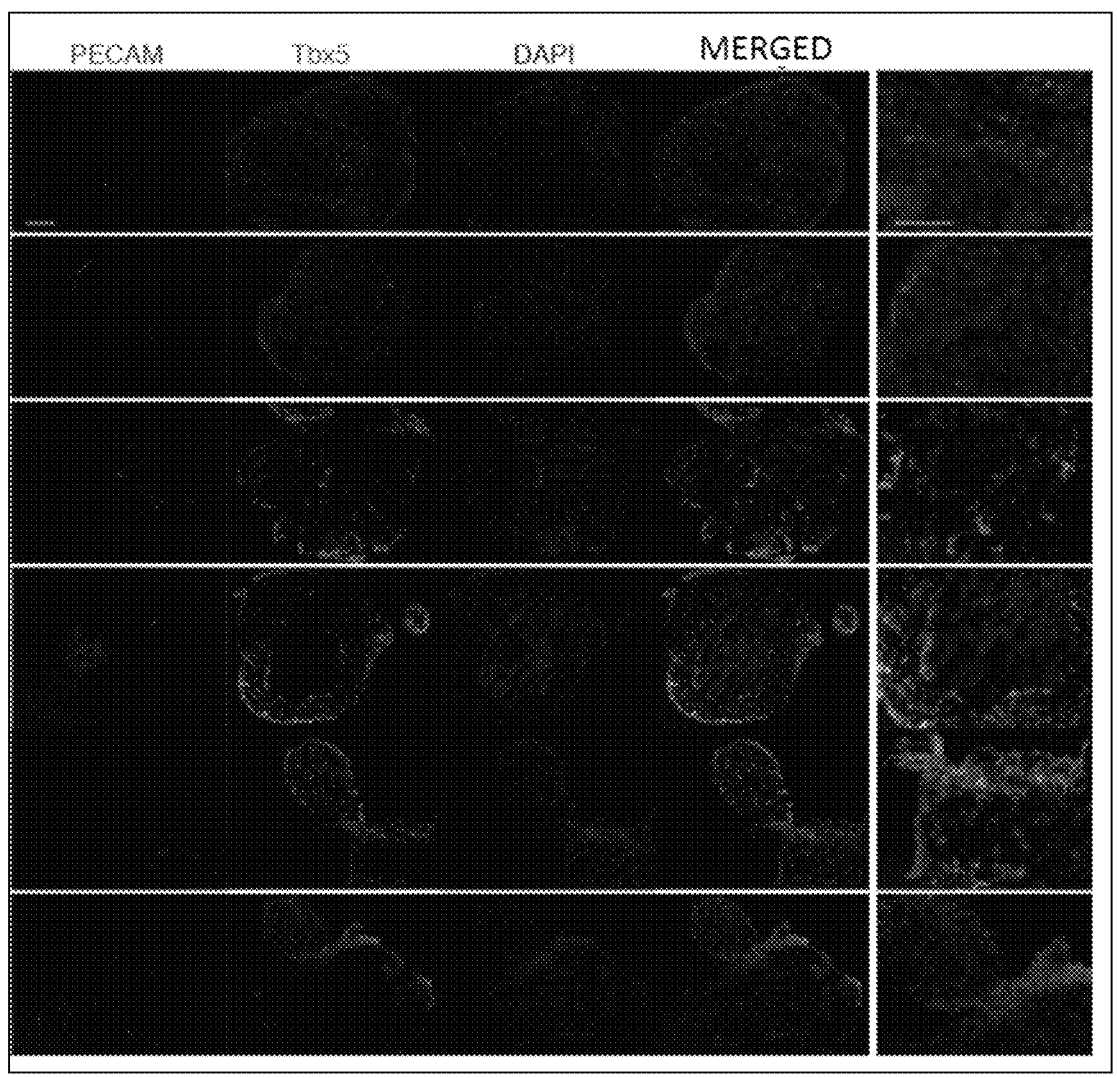

FIG. 14 is a photomicrograph showing the results of detecting the expression of PECAM and Tbx5 in the mouse ES cell-derived heart organoid of the present invention by immunofluorescent staining. In the figure, the expression of Tbx5 is shown in green, and the expression of PECAM is shown in red. In addition, the result of counterstaining with DAPI is shown in blue. In addition, the scale bar represents 100 μm.

Figure 15:
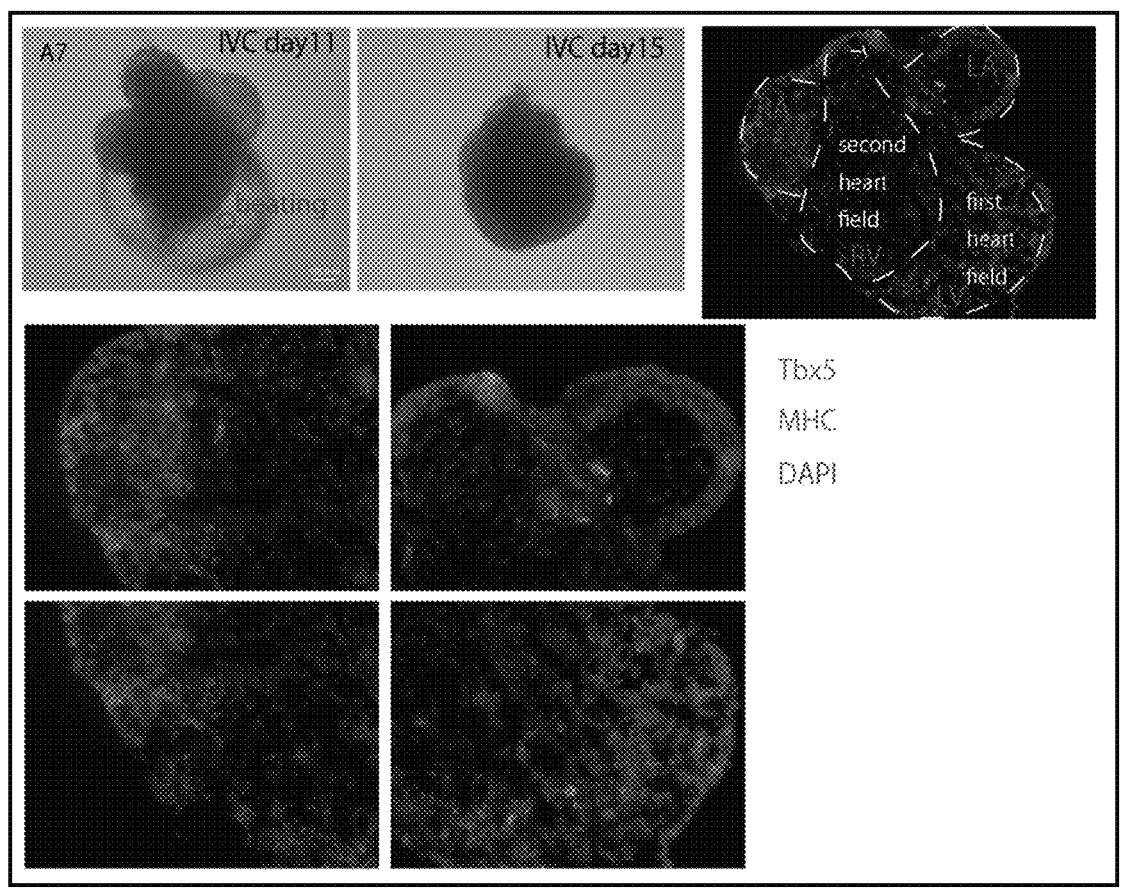

FIG. 15 is a photomicrograph showing the results of detecting the expression of MHC and Tbx5 in the mouse ES cell-derived heart organoid of the present invention by immunofluorescent staining. In the figure, the expression of Tbx5 is shown in green, and the expression of MHC is shown in pink. In addition, the result of counterstaining with DAPI is shown in blue. The scale bar represents 100 μm. In addition, in the figure, the "first heart field" and the "second heart field" indicate the first heart field and the second heart field, respectively, and "RA," "RV," "LA," and "LV" indicate the right atrium, the right ventricle, the left atrium, and the left ventricle, respectively.

Figure 16:
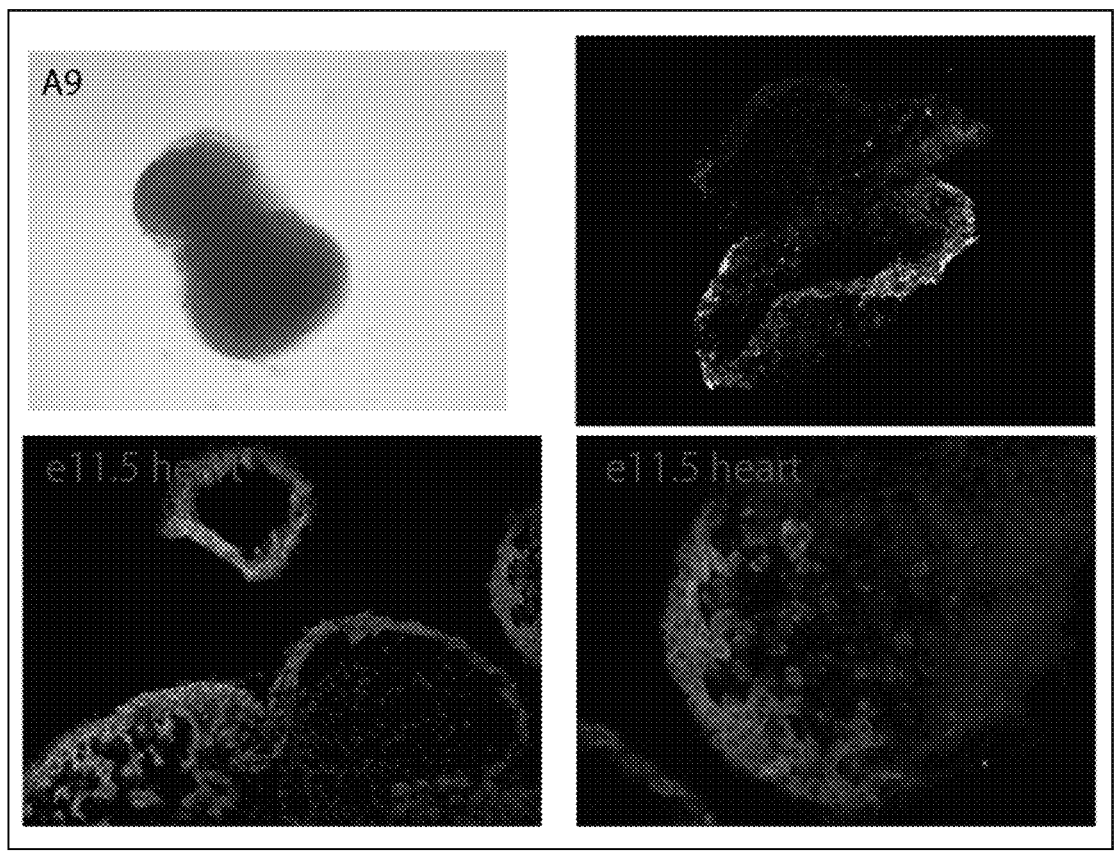

FIG. 16 is a photomicrograph showing the results of detecting the expression of MHC and Tbx5 in the mouse ES cell-derived heart organoid of the present invention and a mouse embryonic heart (embryonic day 11.5) by immunofluorescent staining. In the figure, the upper left photograph shows the result of observing a heart organoid with a microscope in a bright field, the upper right photograph shows the result of observing a heart organoid with a fluorescence microscope, and the lower photographs show the results of observing a mouse embryonic heart with a fluorescence microscope. In addition, in these fluorescence micrographs, the expression of Tbx5 is shown in green, and the expression of MHC is shown in pink. In addition, the result of counterstaining with DAPI is shown in blue.

Figure 17:
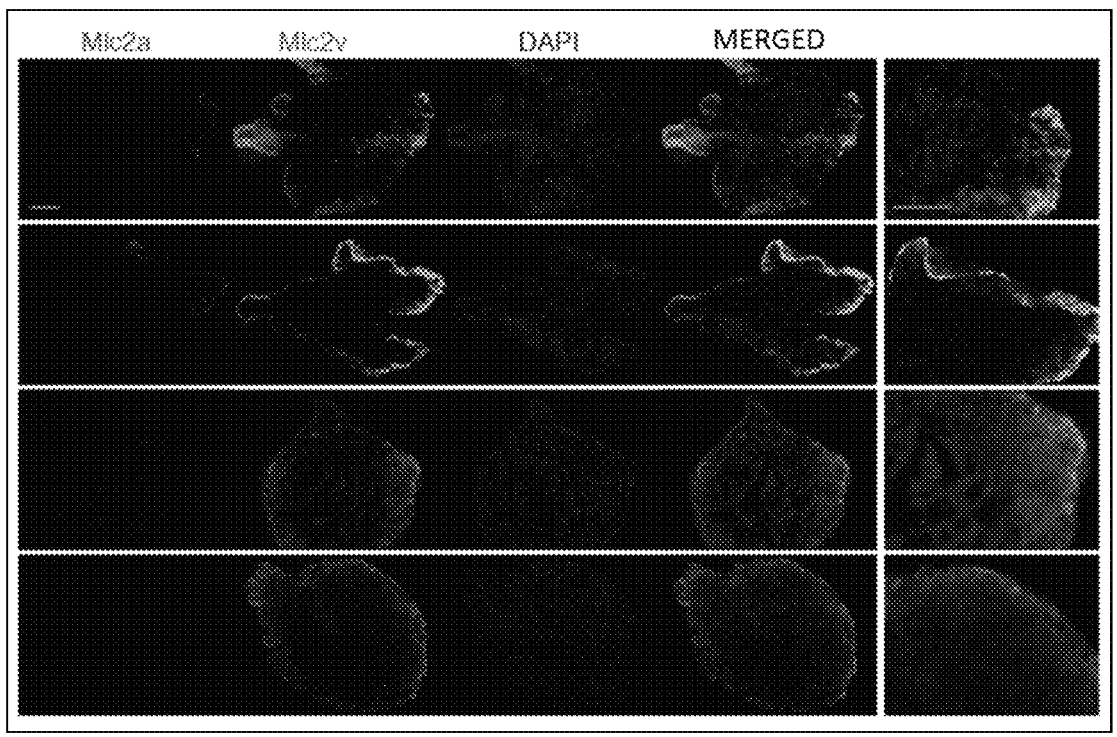

FIG. 17 is a photomicrograph showing the results of detecting the expression of Mlc2a and Mlc2v in the mouse ES cell-derived heart organoid of the present invention by immunofluorescent staining. In the figure, the expression of Mlc2a is shown in pink, and the expression of Mlc2v is shown in green. In addition, the result of counterstaining with DAPI is shown in blue. The scale bar represents 100 μm.

Figure 18:
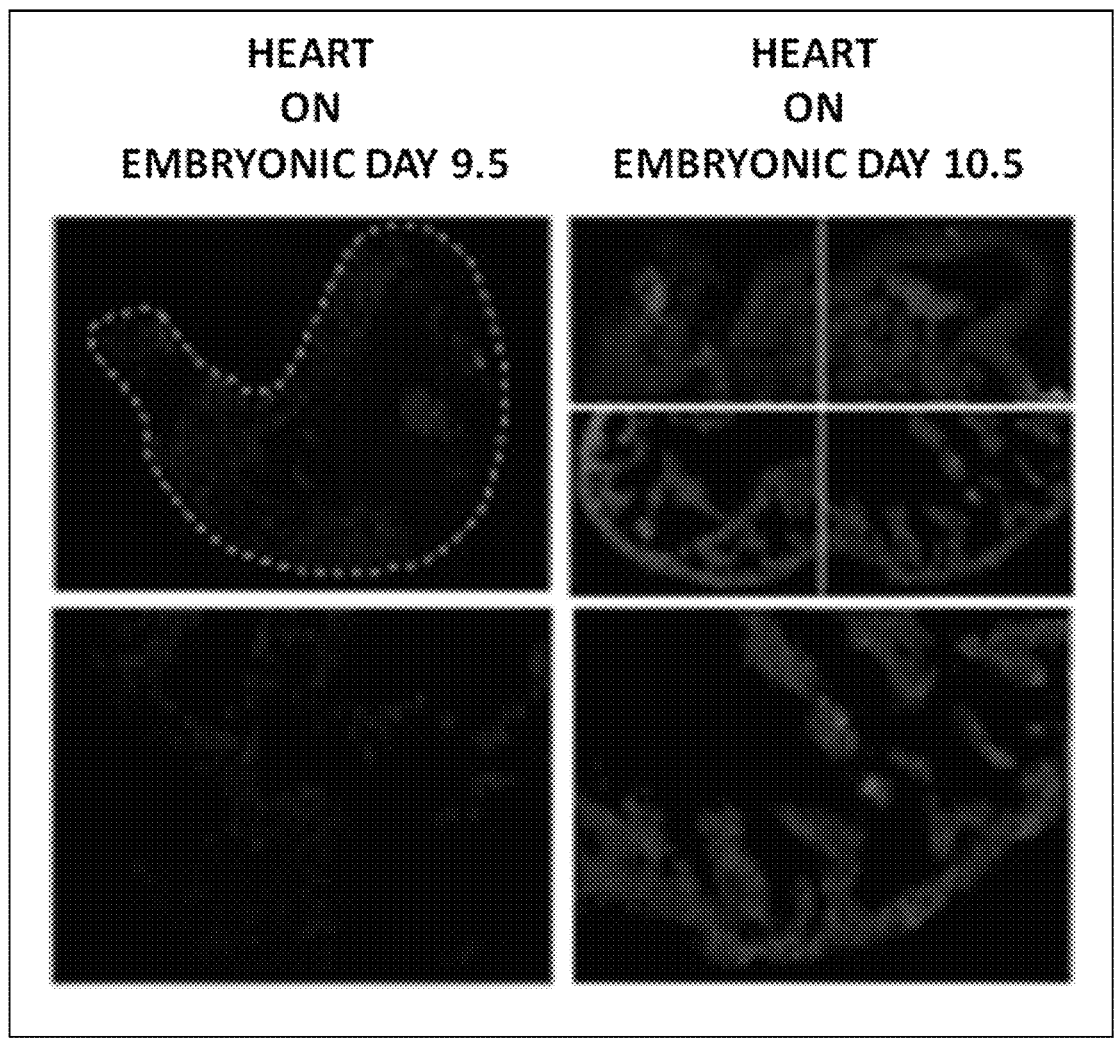

FIG. 18 is a photomicrograph showing the results of detecting the expression of Mlc2a and Mlc2v in mouse embryonic hearts (embryonic days 9.5 and 10.5) by immunofluorescent staining. In the figure, the expression of Mlc2a is shown in pink, and the expression of Mlc2v is shown in green. In addition, the result of counterstaining with DAPI is shown in blue.

Figure 19:
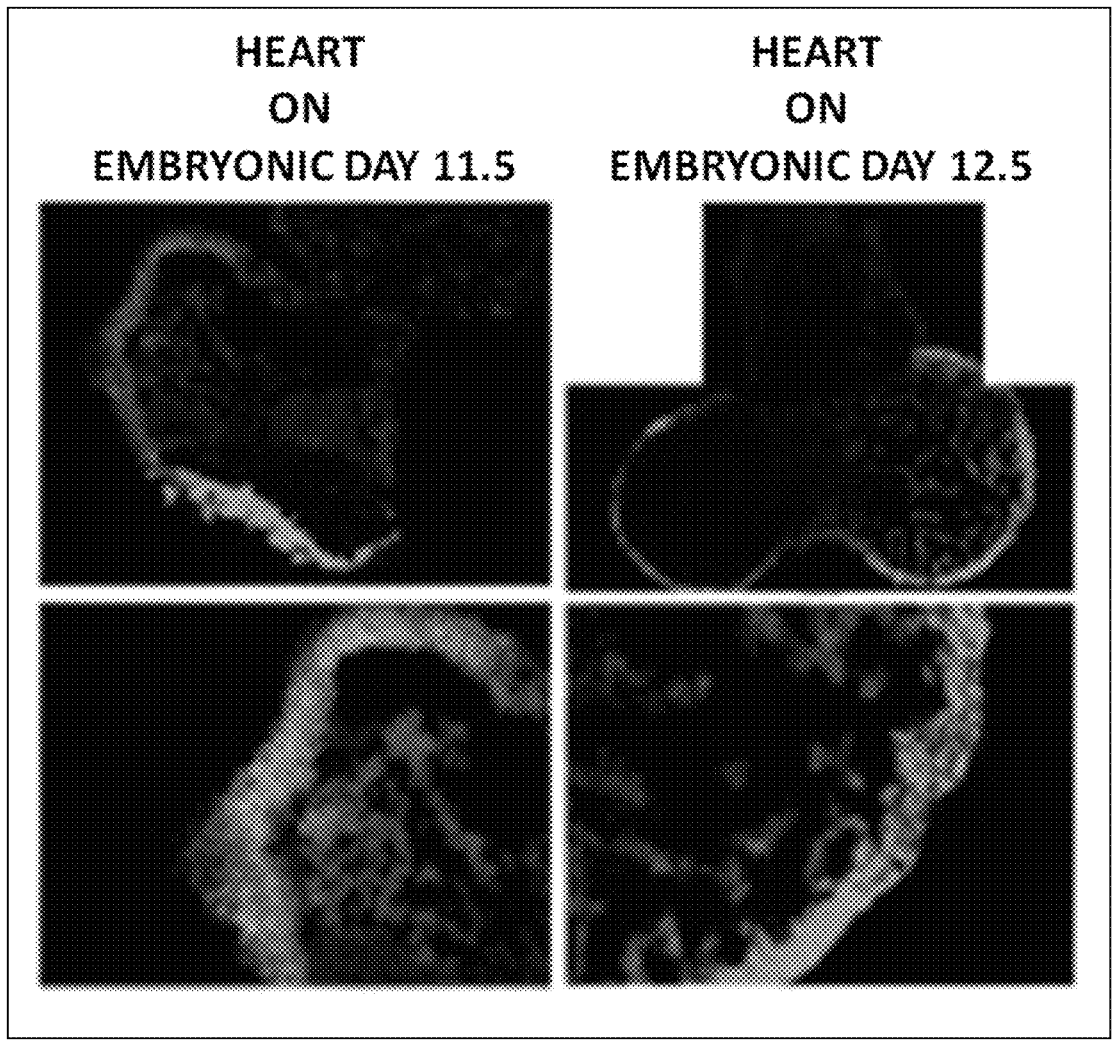

FIG. 19 is a photomicrograph showing the results of detecting the expression of Mlc2a and Mlc2v in mouse embryonic hearts (embryonic days 11.5 and 12.5) by immunofluorescent staining. In the figure, the expression of Mlc2a is shown in pink, and the expression of Mlc2v is shown in green. In addition, the result of counterstaining with DAPI is shown in blue.

Figure 20:
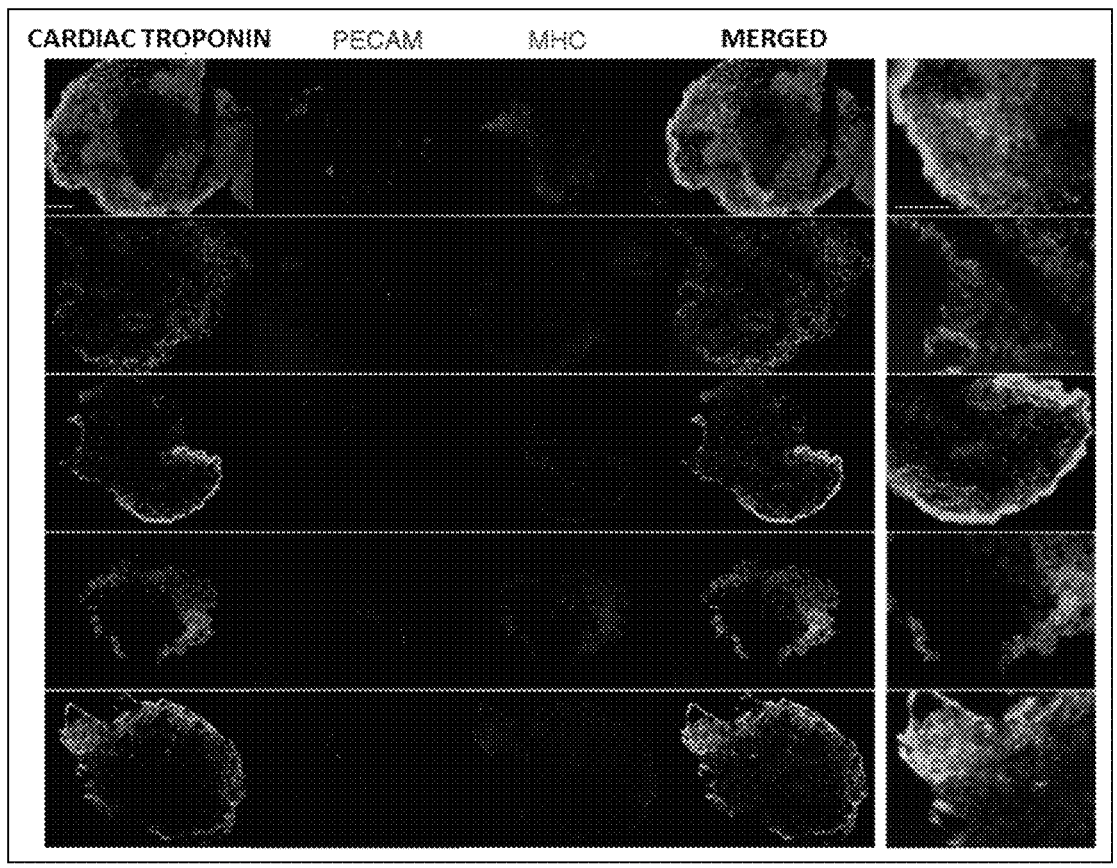

FIG. 20 is a photomicrograph showing the results of detecting the expression of cardiac troponin I, PECAM, and MHC in the mouse ES cell-derived heart organoid of the present invention by immunofluorescent staining. In the figure, the expression of cardiac troponin I is shown in green, the expression of PECAM is shown in red, and the expression of MHC is shown in pink. In addition, the result of counterstaining with DAPI is shown in blue.

Figure 21:
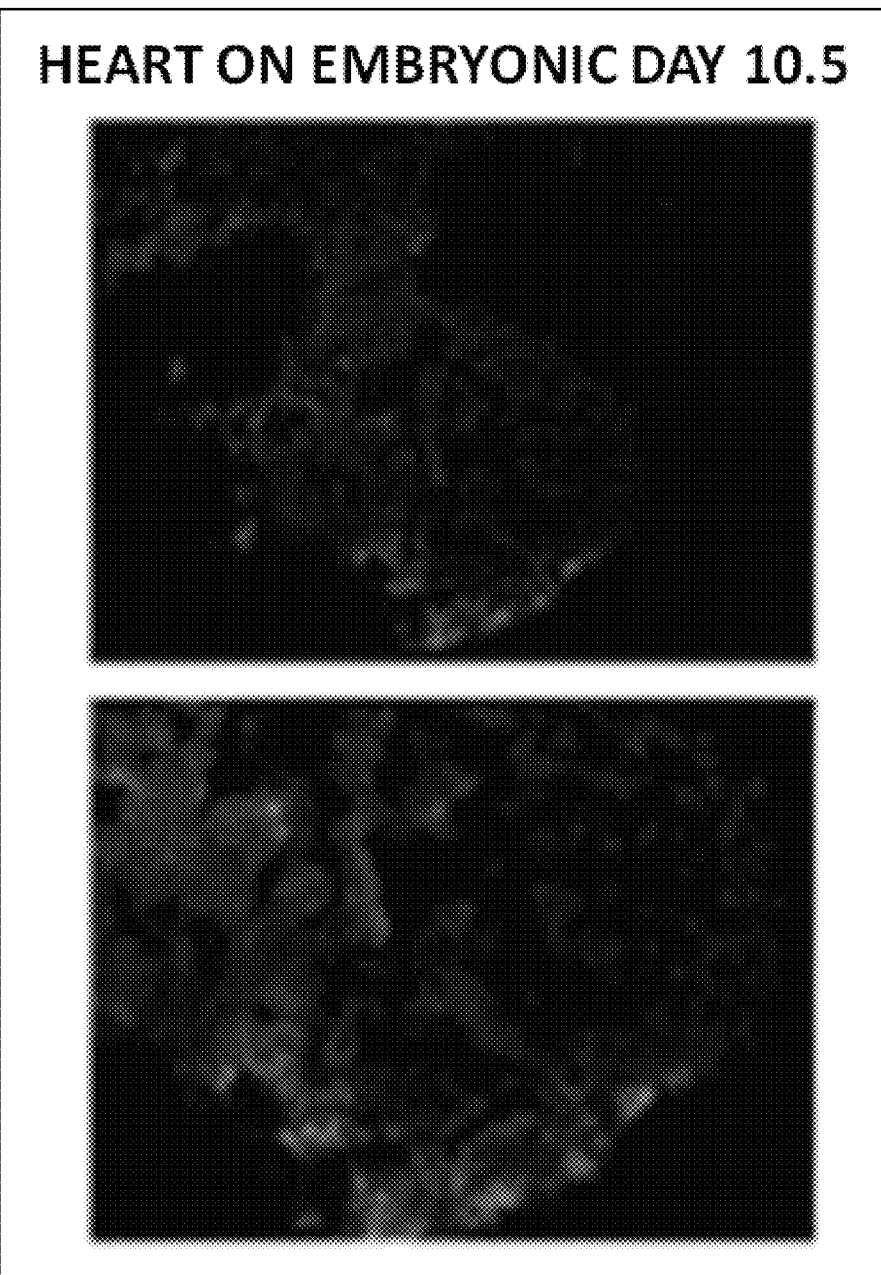

FIG. 21 is a photomicrograph showing the results of detecting the expression of cardiac troponin I, PECAM, and MHC in a mouse embryonic heart (embryonic day 10.5) by immunofluorescent staining. In the figure, the expression of cardiac troponin I is shown in green, the expression of PECAM is shown in red, and the expression of MHC is shown in pink. In addition, the result of counterstaining with DAPI is shown in blue.

Figure 22:
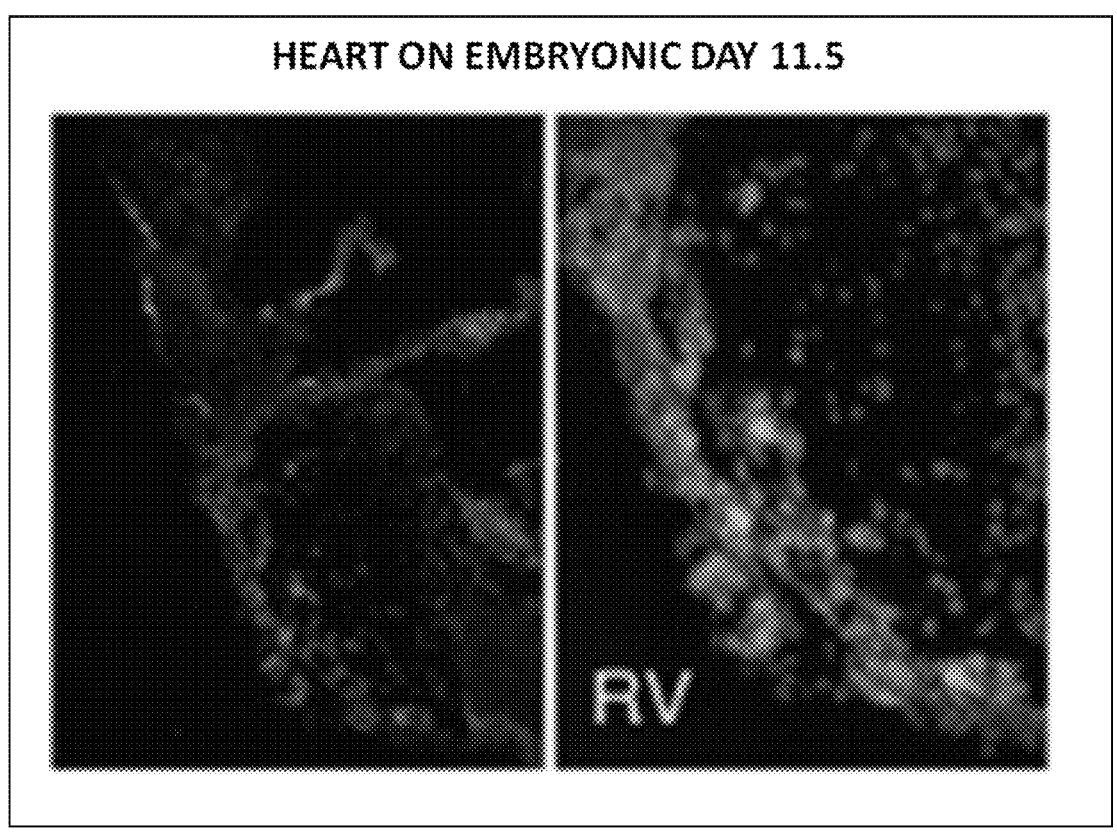

FIG. 22 is a photomicrograph showing the results of detecting the expression of cardiac troponin I, PECAM, and MHC in a mouse embryonic heart (embryonic day 11.5) by immunofluorescent staining. In the figure, the expression of cardiac troponin I is shown in green, the expression of PECAM is shown in red, and the expression of MHC is shown in pink. In addition, the result of counterstaining with DAPI is shown in blue. In the figure, "RV" indicates the right ventricle.

Figure 23:
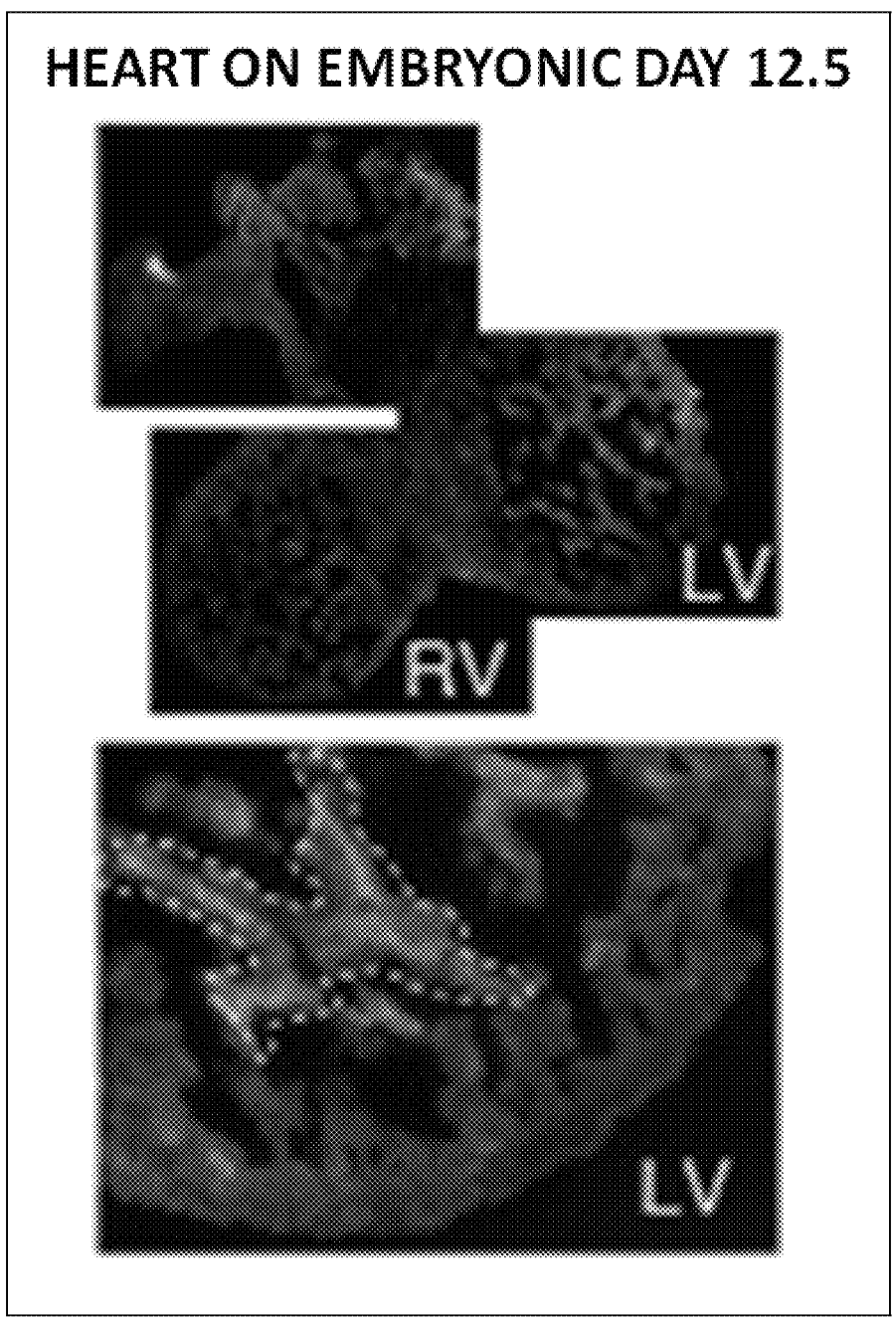

FIG. 23 is a photomicrograph showing the results of detecting the expression of cardiac troponin I, PECAM, and MHC in a mouse embryonic heart (embryonic day 12.5) by immunofluorescent staining. In the figure, the expression of cardiac troponin I is shown in green, the expression of PECAM is shown in red, and the expression of MHC is shown in pink. In addition, the result of counterstaining with DAPI is shown in blue. In the figure, "RV" and "LV" indicate the right ventricle and the left ventricle, respectively.

Figure 24:
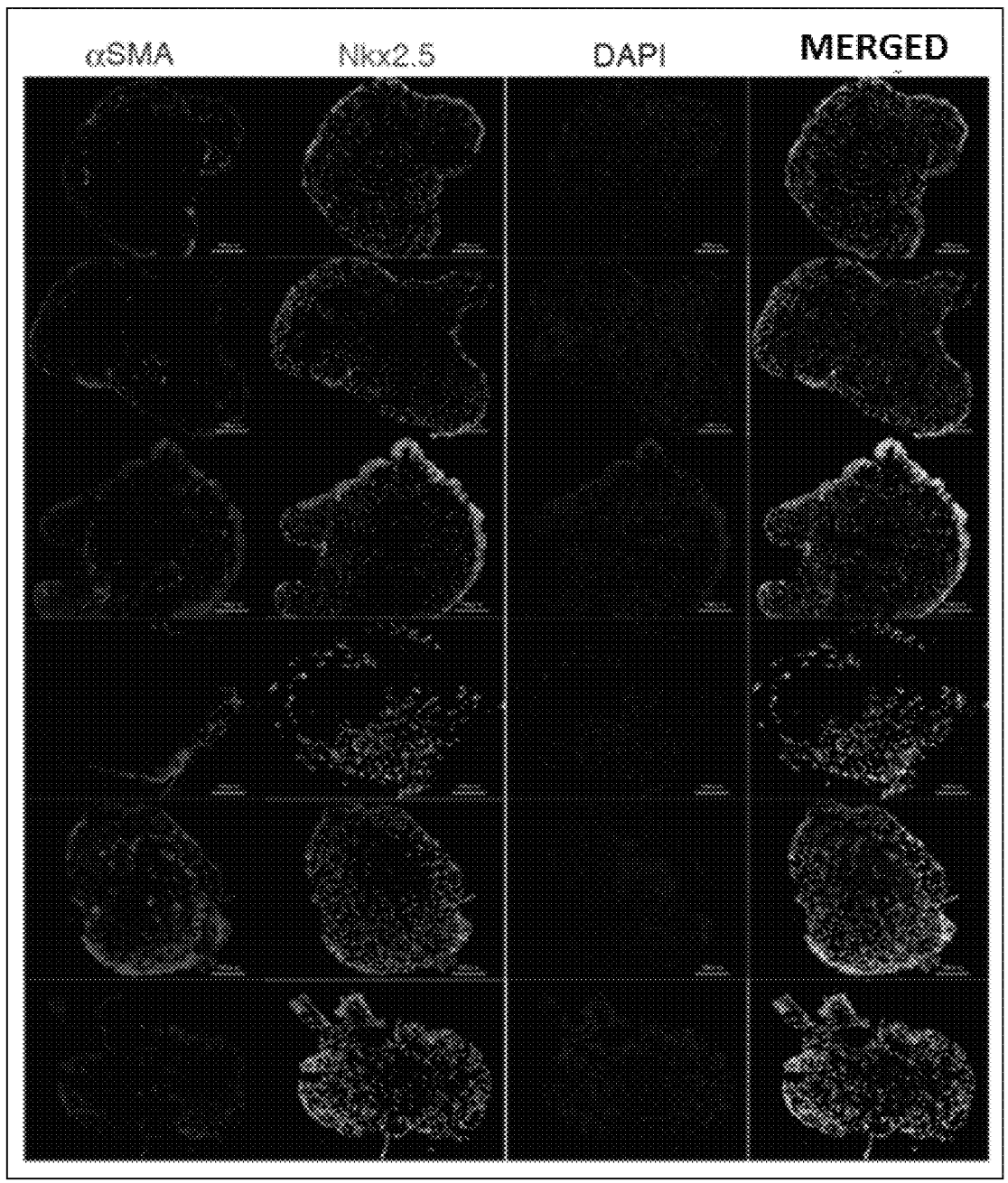

FIG. 24 is a photomicrograph showing the results of detecting the expression of αSMA and Nkx2-5 in the mouse ES cell-derived heart organoid of the present invention by immunofluorescent staining. In the figure, the expression of αSMA is shown in red, and the expression of Nkx2-5 is shown in green. In addition, the result of counterstaining with DAPI is shown in blue.

Figure 25:
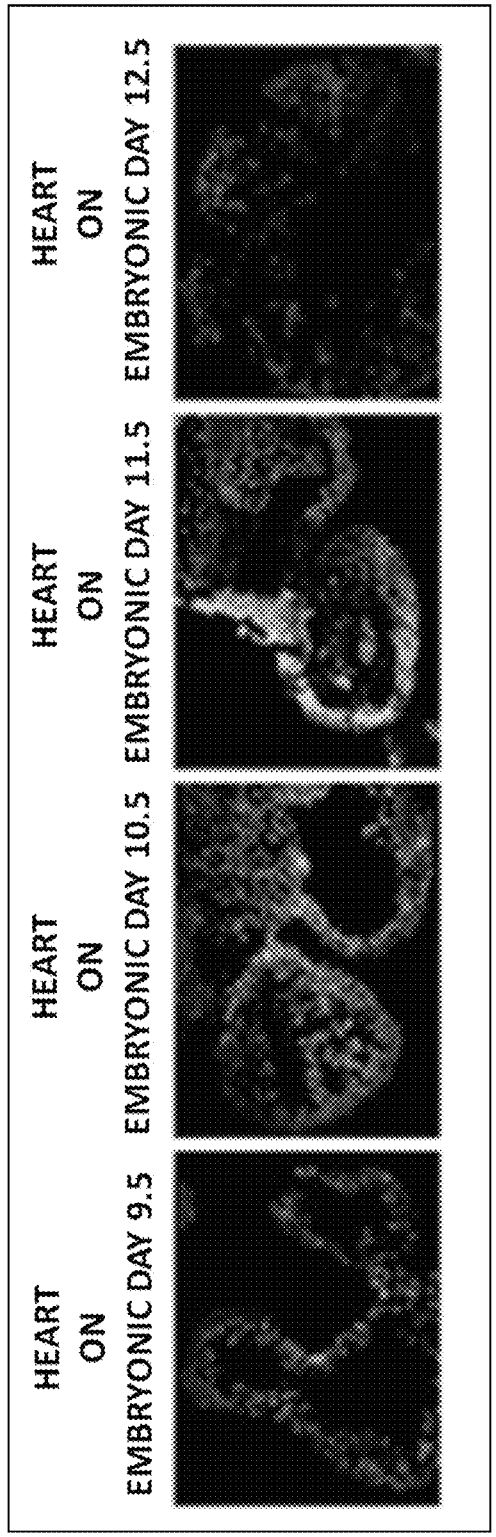

FIG. 25 is a photomicrograph showing the results of detecting the expression of USMA and Nkx2-5 in mouse embryonic hearts (embryonic days 9.5, 10.5, 11.5, and 12.5) by immunofluorescent staining. In the figure, the expression of αSMA is shown in red, and the expression of Nkx2-5 is shown in green. In addition, the result of counterstaining with DAPI is shown in blue.

Figure 26:
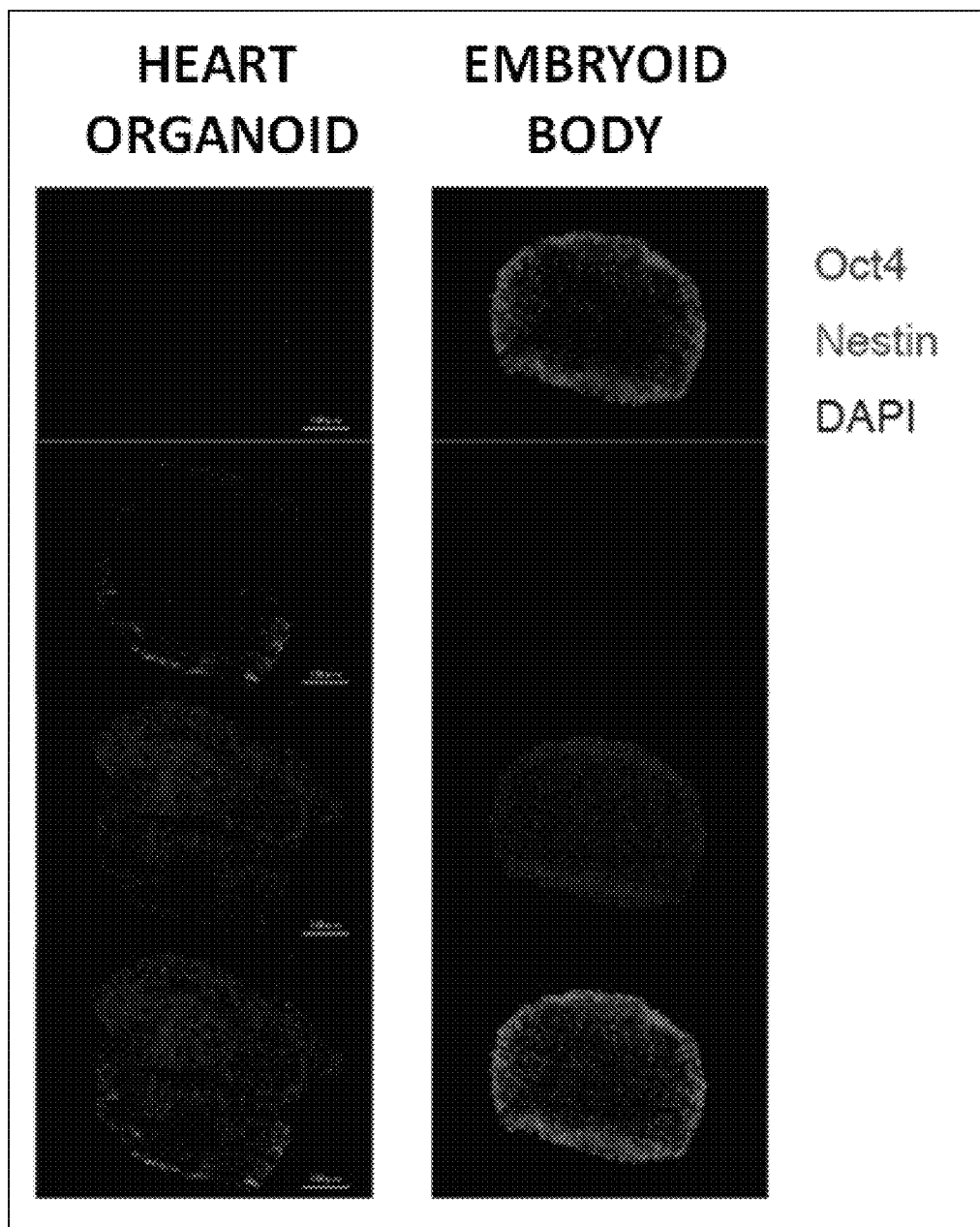

FIG. 26 is a photomicrograph showing the results of detecting the expression of Oct4 and nestin in the mouse ES cell-derived heart organoid of the present invention and an embryoid body by immunofluorescent staining. In the figure, the expression of Oct4 is shown in red, and the expression of nestin is shown in green. In addition, the result of counterstaining with DAPI is shown in blue.

Figure 27:
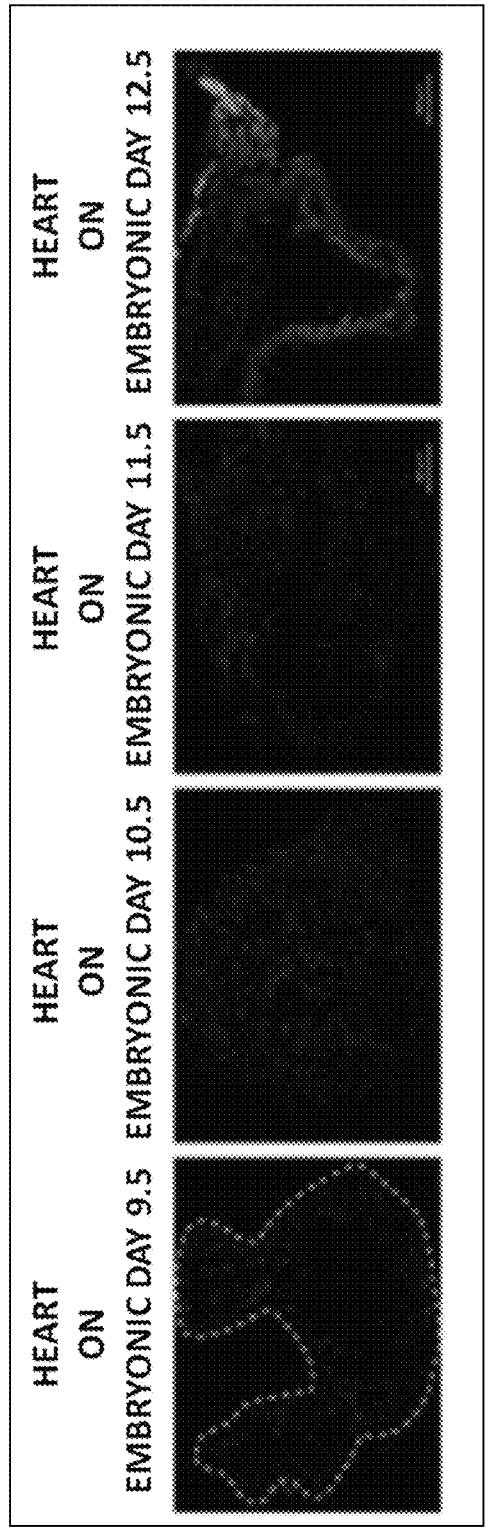

FIG. 27 is a photomicrograph showing the results of detecting the expression of Oct4 and nestin in mouse embryonic hearts (embryonic days 9.5, 10.5, 11.5, and 12.5) by immunofluorescent staining. In the figure, the expression of Oct4 is shown in red, and the expression of nestin is shown in green. In addition, the result of counterstaining with DAPI is shown in blue.

Figure 28:
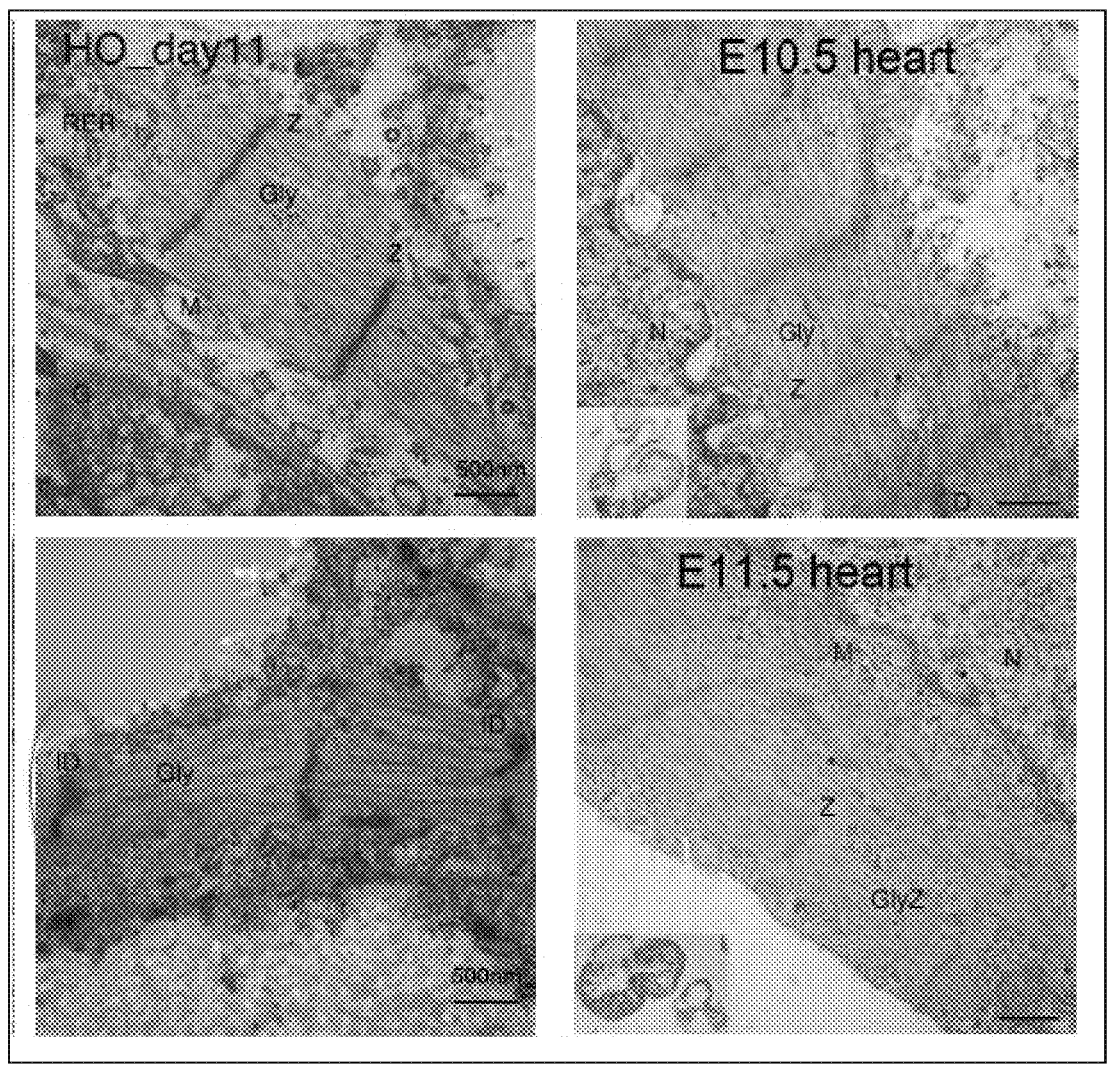

FIG. 28 is a photograph showing the results of analyzing the microstructure of the mouse ES cell-derived heart organoid of the present invention and a mouse embryonic heart using a transmission electron microscope. In the figure, "HO day11" and the photograph below it together indicate the results of analyzing a heart organoid (day 11 of culture), and "E10.5 heart" and "E11.5 heart" indicate the results of analyzing a mouse embryonic heart (embryonic day 10.5) and a mouse embryonic heart (embryonic day 11.5), respectively. In addition, in these photographs of embryonic hearts, the blue inset photograph at each lower left corner is a photograph showing the result of toluidine blue staining of a section of each heart for electron microscopy and photographing the whole. In each electron micrograph, "Z" indicates a sarcomere structure including the Z line, "ID" indicates an intercalated disc that is a cardiomyocyte-specific structure, "Gly" indicates glycogen, "RER" indicates rough endoplasmic reticulum, "M" indicates mitochondria, "D" indicates desmosome, and "LD" indicates lipid droplet.

Figure 29:
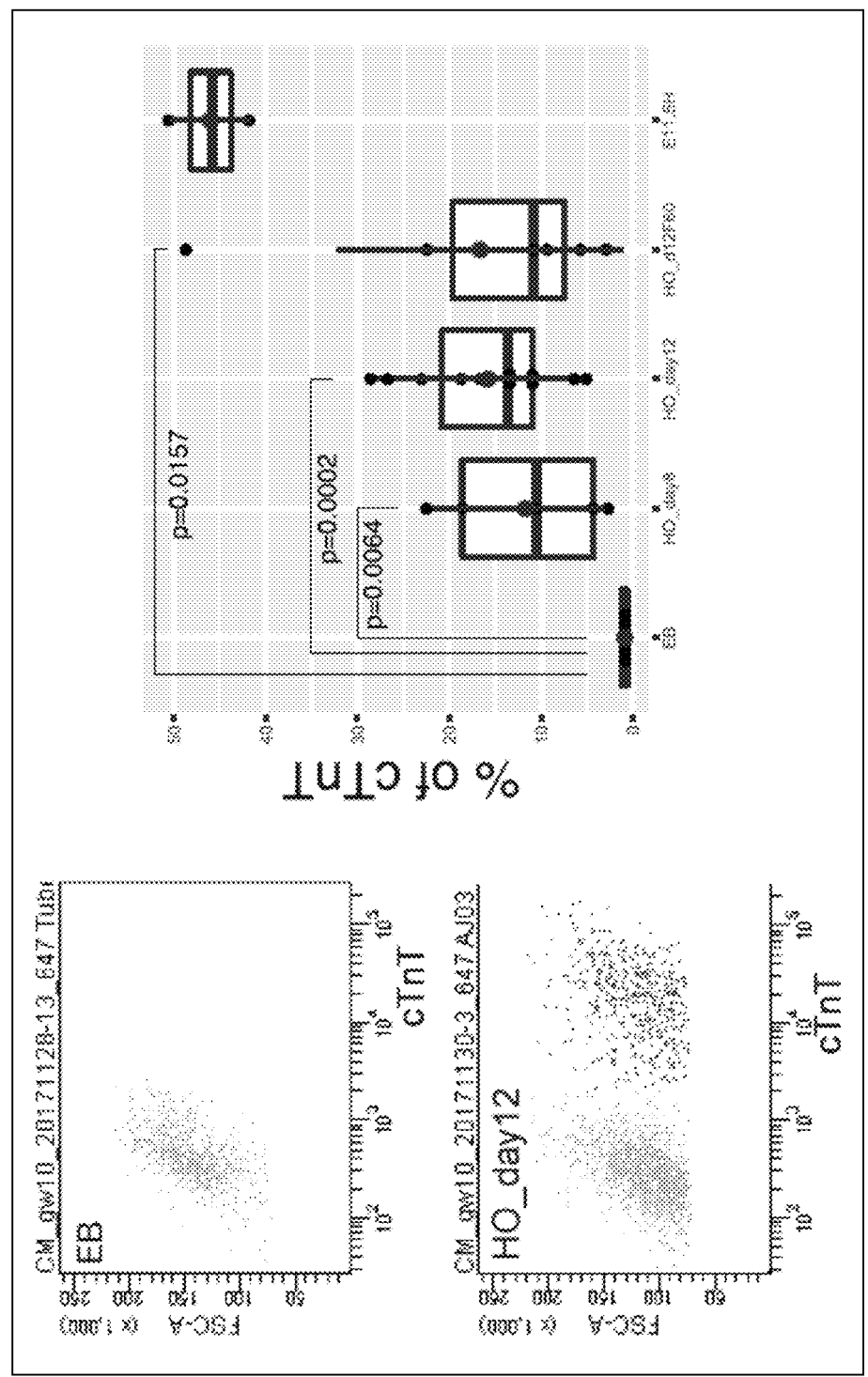

FIG. 29 is a diagram showing the results of analyzing cardiomyocytes in an embryoid body, the mouse ES cell-derived heart organoid of the present invention, and a mouse embryonic heart (embryonic day 11.5) by flow cytometry after cardiac troponin T antibody staining. In the figure, the left panels show representative dot plots of the embryoid body (EB) and the heart organoid on day 12 of culture (HO_day12). The right panels are dot box plots showing the percentage of cTnT positive cells in an embryoid body (EB), a heart organoid on day 8 of culture in the presence of 30 ng/mL FGF4 (HO_day8), a heart organoid on day 12 of culture in the presence of 30 ng/mL FGF4 (HO_day12), a heart organoid on day 12 of culture in the presence of 60 ng/mL FGF4 (HO_day12F60), and an mouse embryonic heart on embryonic day 11.5 (E11.5H). The P-values in the figure are values obtained by T-TEST.

Figure 30:
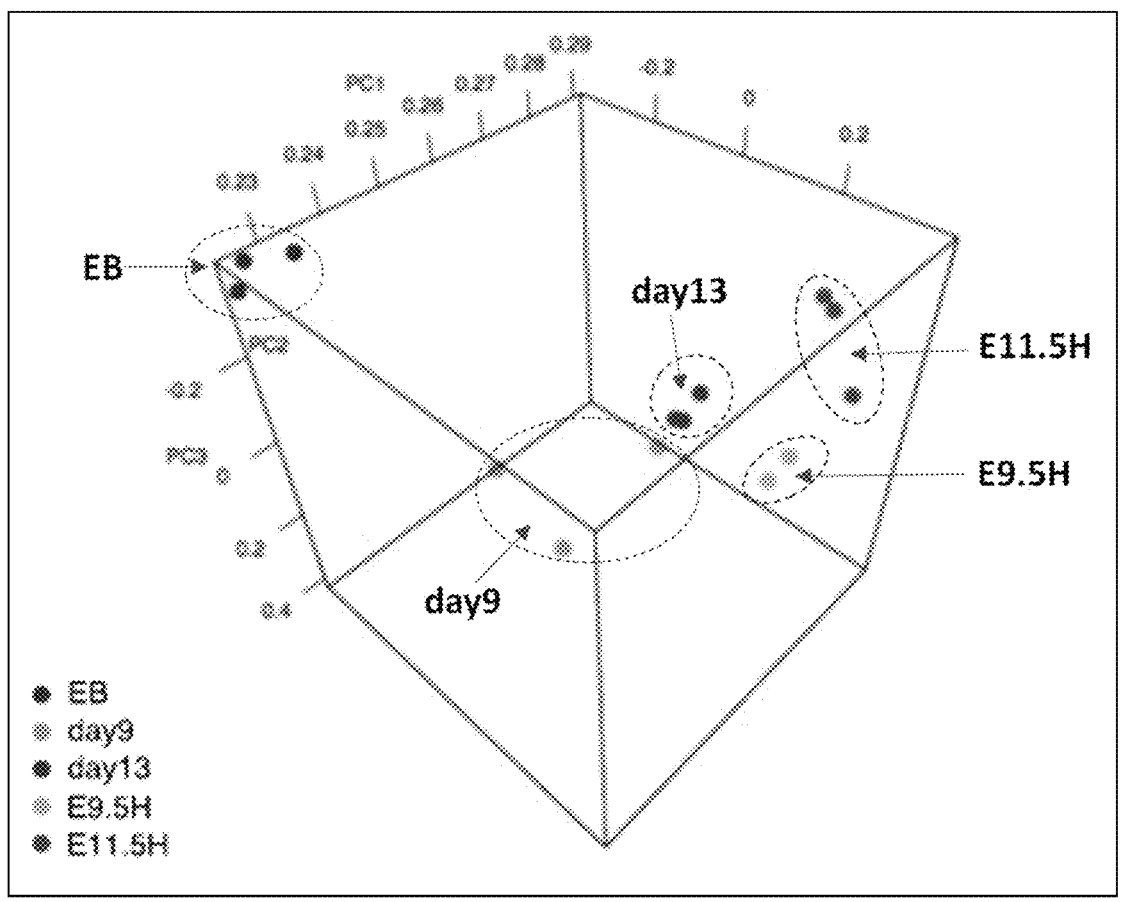

FIG. 30 is a diagram showing the analysis results of principal component analysis (PCA) using RNA-seq data. In the figure, the blue, yellow-green, green, yellow, and red dots indicate the results of analyzing an embryoid body, the mouse ES cell-derived heart organoid of the present invention on day 9 of culture, the mouse ES cell-derived heart organoid of the present invention on day 13 of culture, a heart on embryonic day 9.5, and a heart on embryonic day 11.5, respectively.

Figure 31:
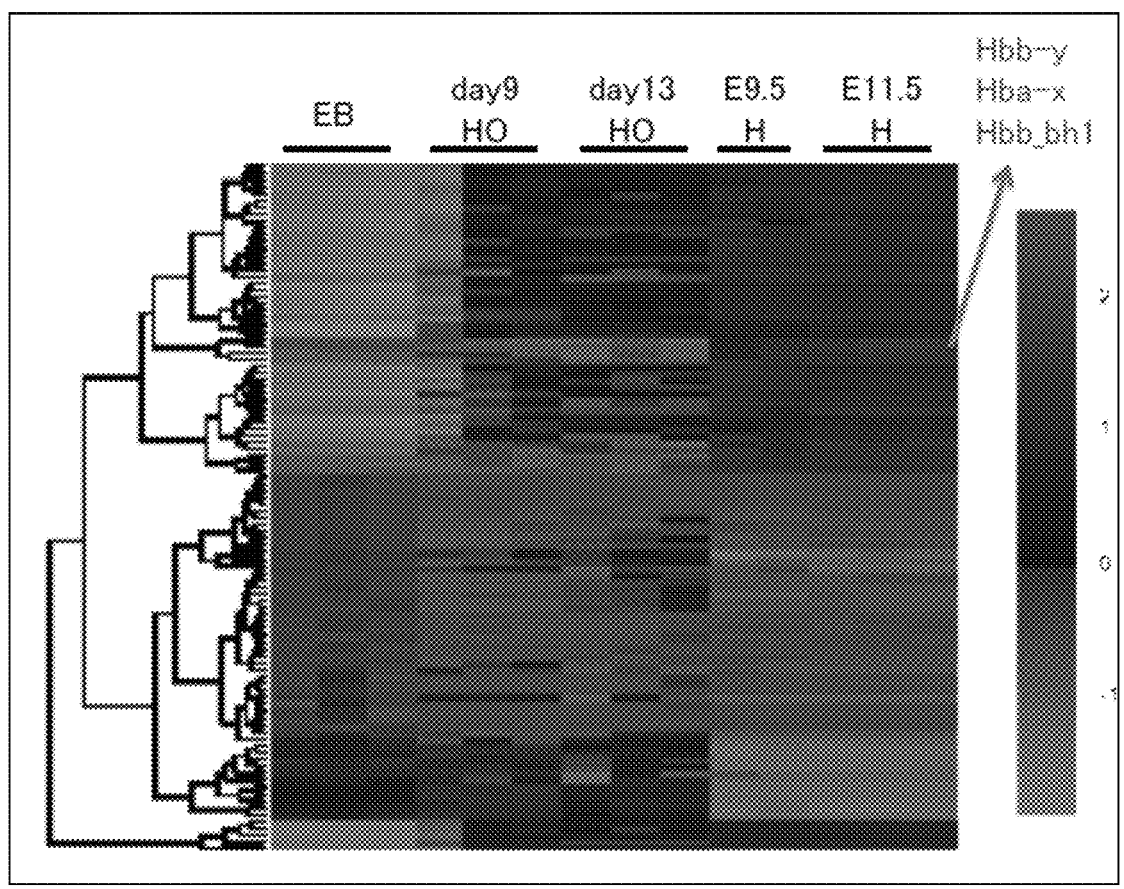

FIG. 31 is a heat map and hierarchical clustering showing the results of analyzing gene expression in an embryoid body (EB), the mouse ES cell-derived heart organoid of the present invention on day 9 of culture (day9 HO), the mouse ES cell-derived heart organoid of the present invention on day 13 of culture (day13 HO), a heart on embryonic day 9.5 (E9.5 H), and a heart on embryonic day 11.5 (E11.5 H).

Figure 32:
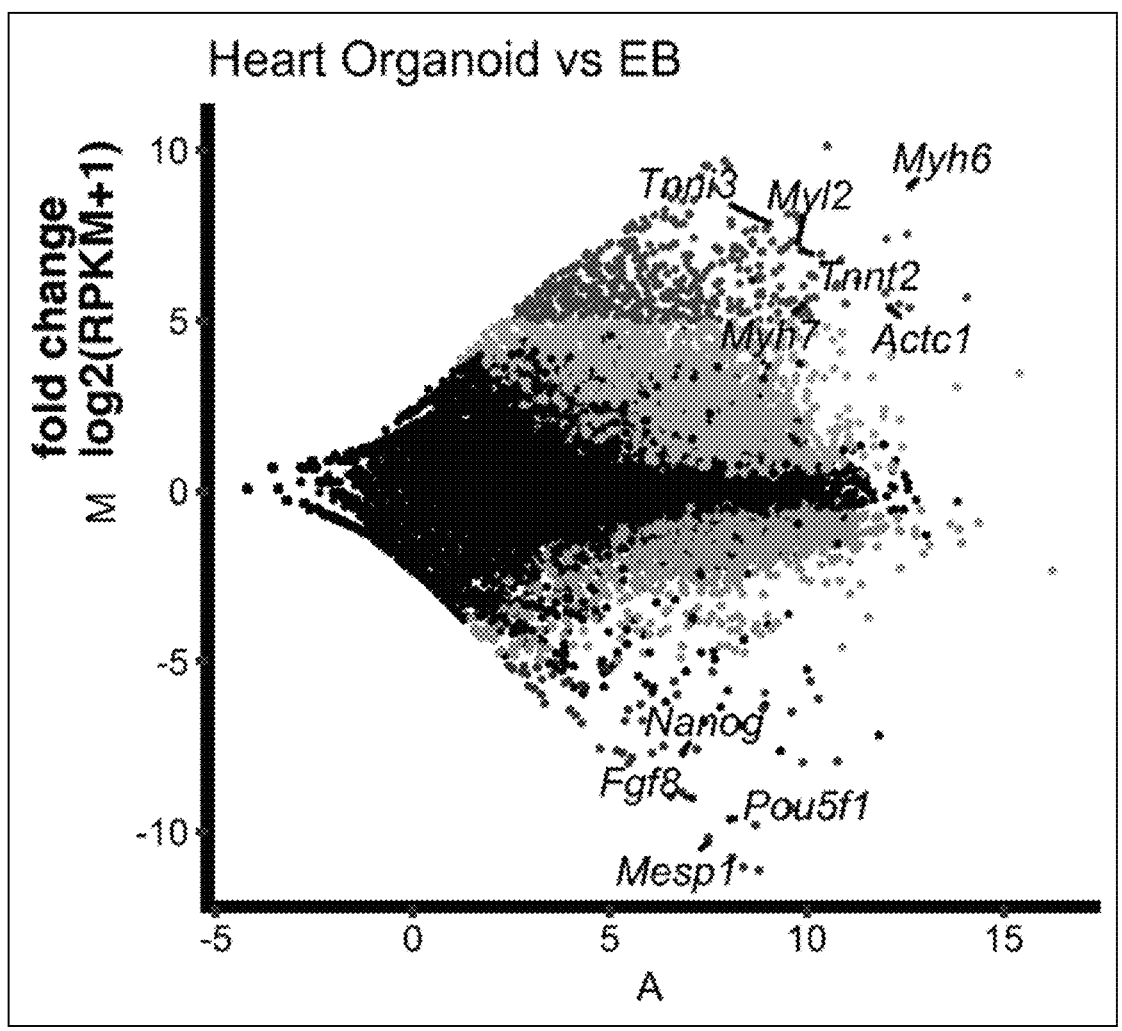

FIG. 32 is an MA plot showing genes having a difference in expression between the mouse ES cell-derived heart organoid of the present invention (Heart Organoid) and an embryoid body (EB). In the figure, genes with regulated P-values<0.01 are shown in color. Specifically, genes with log 2FoldChange>5 are shown in red (396 genes), and genes with log 2FoldChange<−5 are shown in blue (55 genes).

Figure 33:

FIG. 33 is a diagram showing the results of GO (gene ontology) analysis of 39 genes highly expressed in the mouse ES cell-derived heart organoid of the present invention (regulated P-value<0.01, log 2FoldChange>5).

Figure 34:
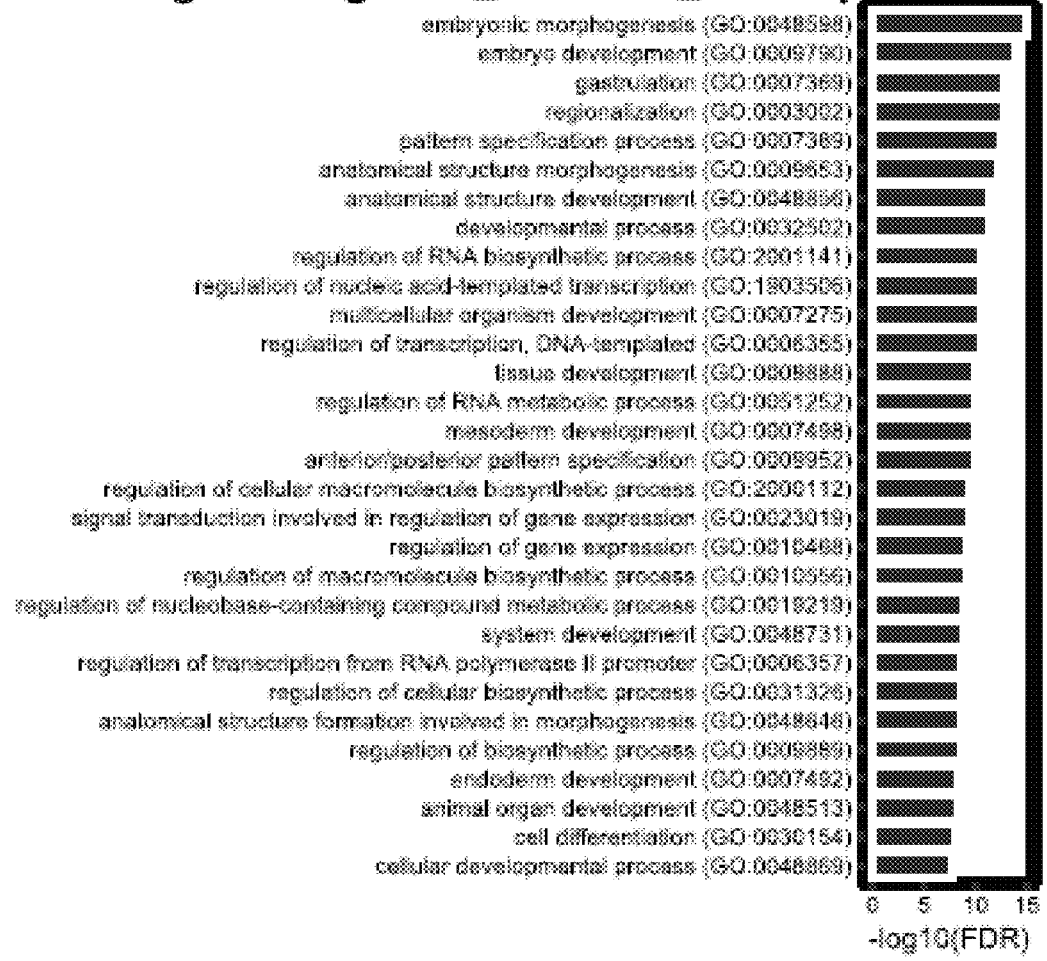

FIG. 34 is a diagram showing the results of GO (gene ontology) analysis of 55 genes lowly expressed in the mouse ES cell-derived heart organoid of the present invention (regulated P-value 0.01, log 2FoldChange<−5).

Figure 35:
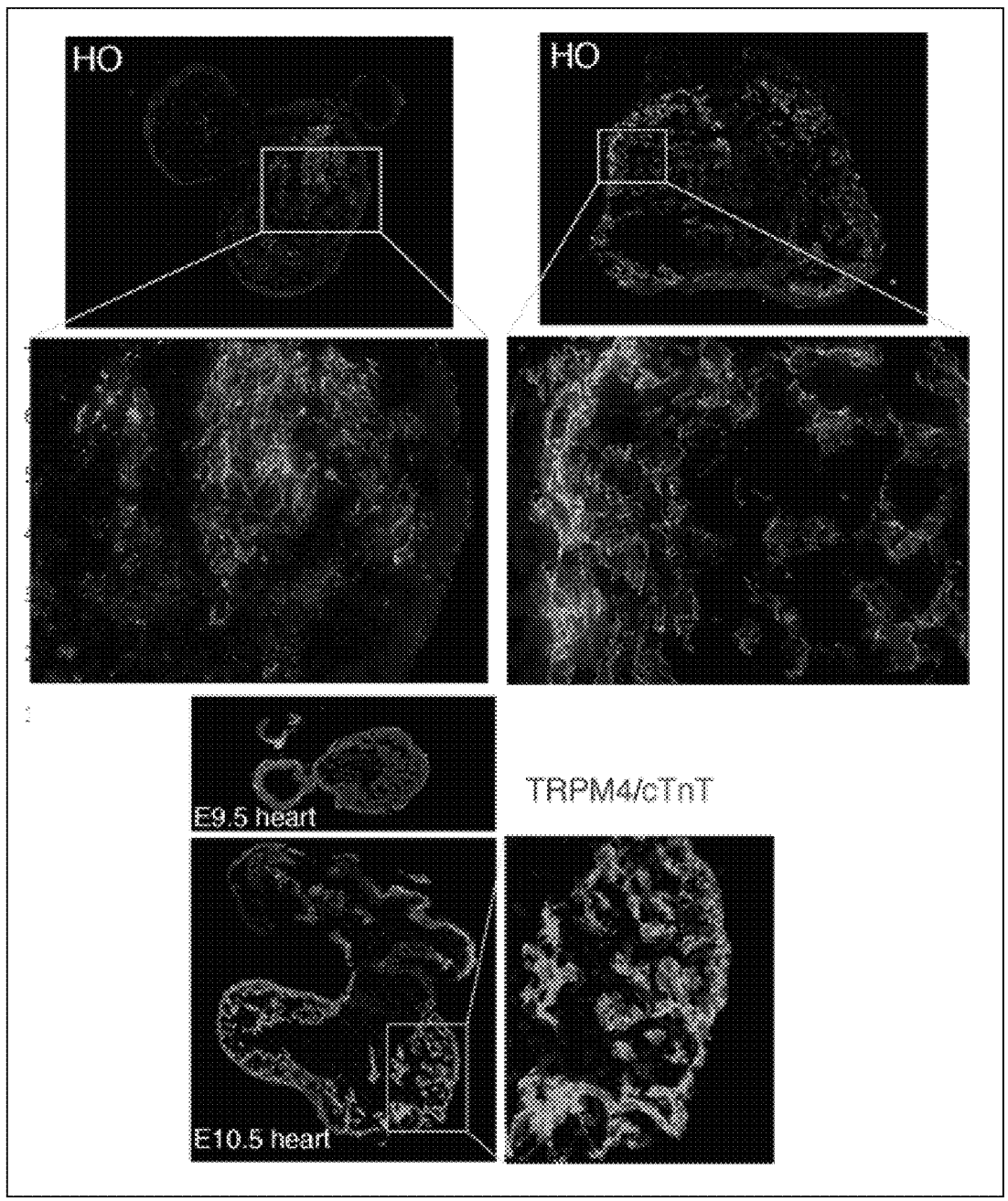

FIG. 35 is a photomicrograph showing the results of detecting the expression of cardiac troponin T (whose expression is shown in green in the figure) and TRPM4 expressed with Purkinje fiber (whose expression is shown in red in the figure) by immunofluorescent staining in the mouse ES cell-derived heart organoid of the present invention ("HO" in the figure) and mouse hearts on embryonic days 9.5 and 10.5 ("E9.5 heart" and "E10.5 heart" in the figure).

Figure 36:
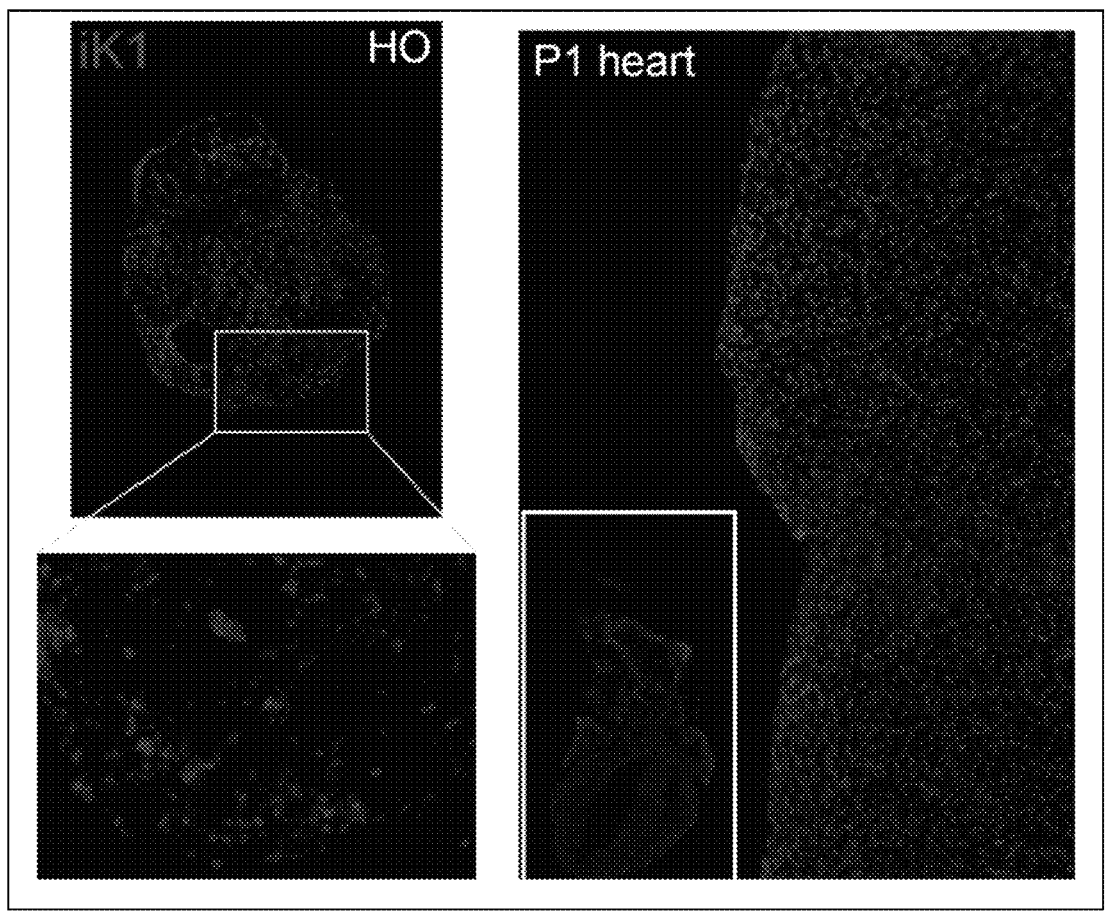

FIG. 36 is a photomicrograph showing the results of detecting the expression of iK1 (whose expression is shown in red in the figure) by immunofluorescent staining in the mouse ES cell-derived heart organoid of the present invention (two photographs on the left in the figure) and a mouse heart on day 1 after birth (photograph on the right in the figure). Note that, in the figure, the photograph at the lower left corner in the photograph on the right (P1 heart) is a photomicrograph showing the entire tissue section of the mouse heart on day 1 after birth.

Figure 37:
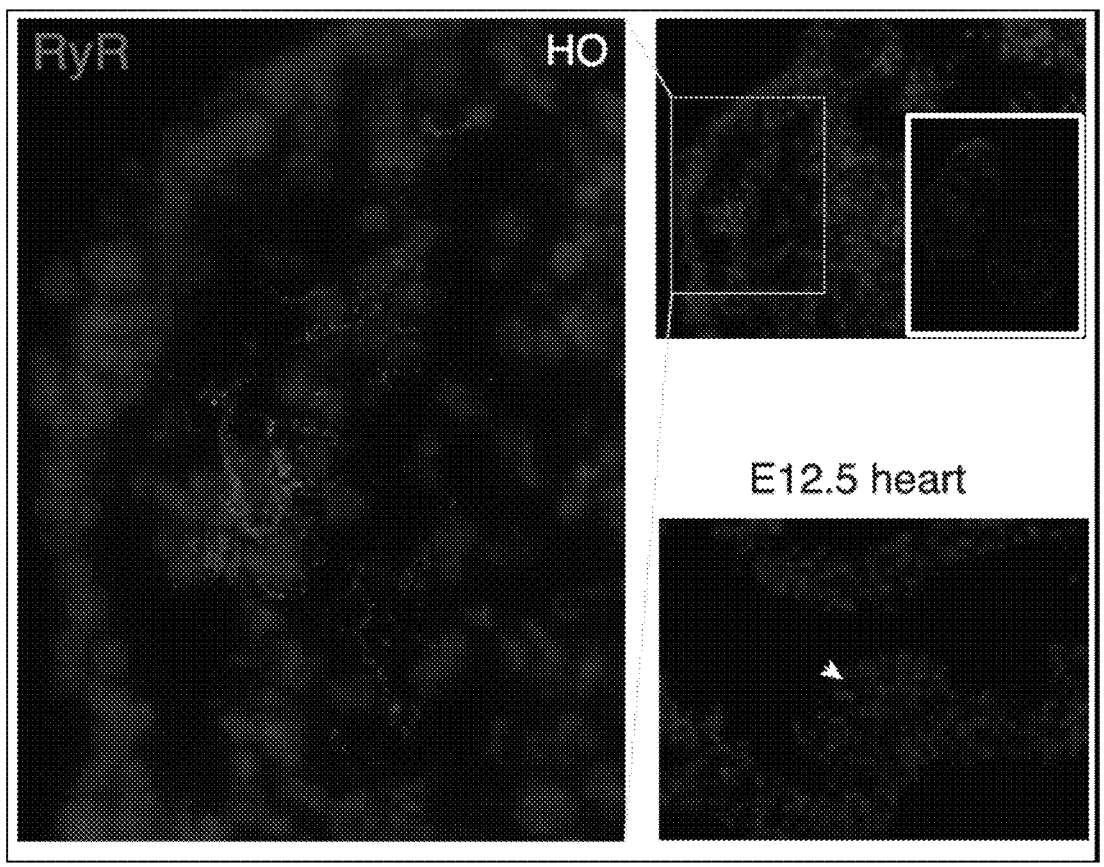

FIG. 37 is a photomicrograph showing the results of detecting the expression of RyR (whose expression is shown in green in the figure) by immunofluorescent staining in the mouse ES cell-derived heart organoid of the present invention ("HO" in the figure) and a mouse heart on embryonic day 12.5. Note that, in the figure, the photograph at the lower right corner in the photograph on the upper right is a photomicrograph showing the entire tissue section of the heart organoid.

Figure 38:
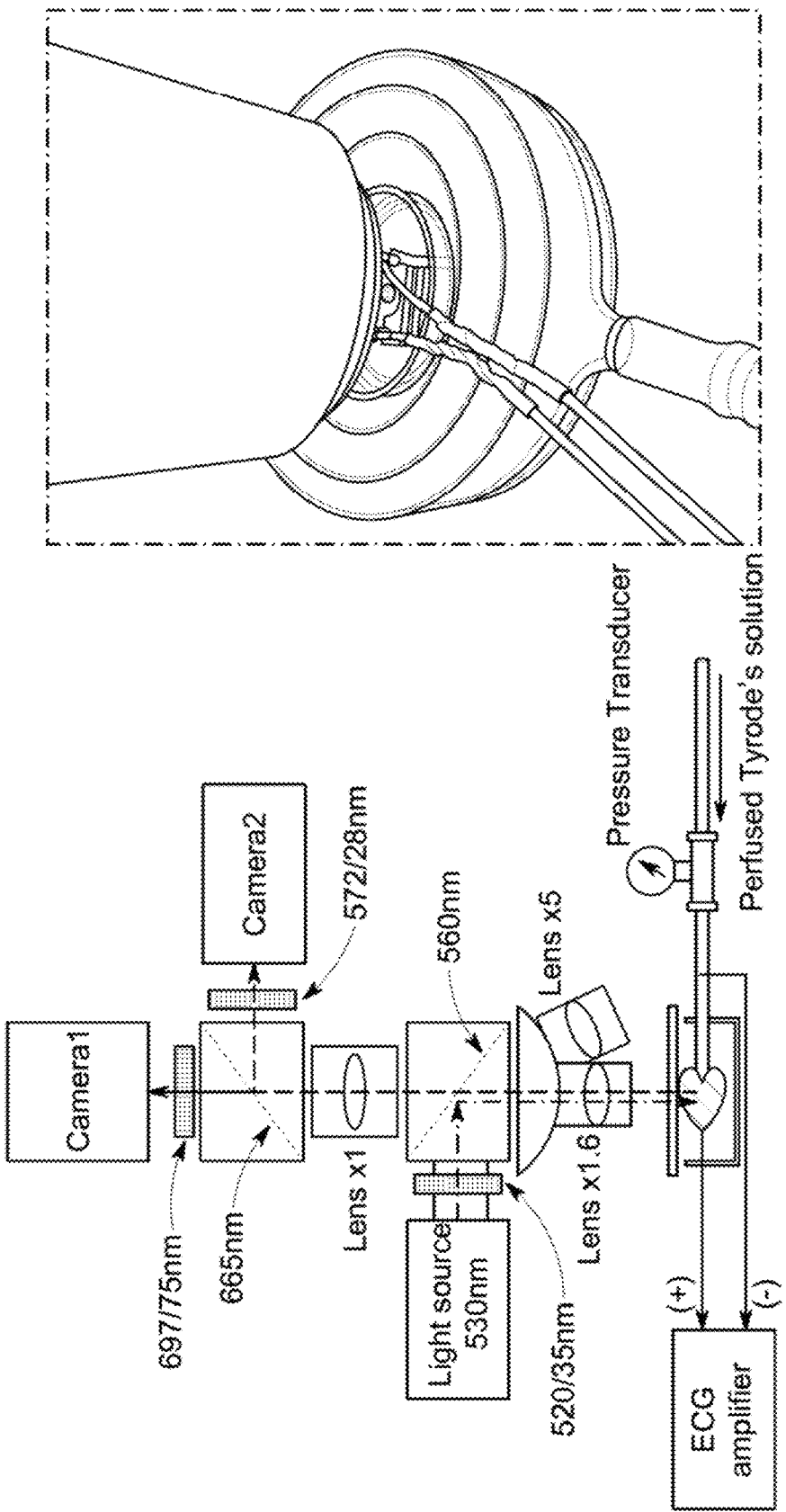

FIG. 38 is an optical path diagram and a photograph (Ihara et al. (J Vis Exp. 2018; (132): 56478)) showing the overview of an optical mapping system. Note that Examples to be described later used only camera 1 shown in the optical path diagram. In addition, in the photograph, the green circle visible in the center is a measurement point (approximately 3 mm in diameter, the recording area is 2×2 mm therein), and the tips of the green codes are stimulating electrodes for field pulse.

Figure 39:
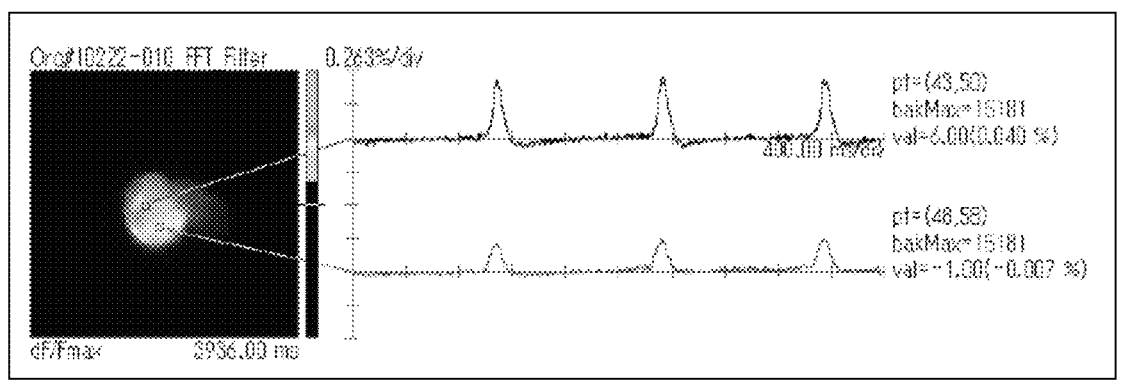

FIG. 39 is a diagram showing the results of electrophysiological analysis of the mouse ES cell-derived heart organoid of the present invention by optical mapping.

Figure 40:
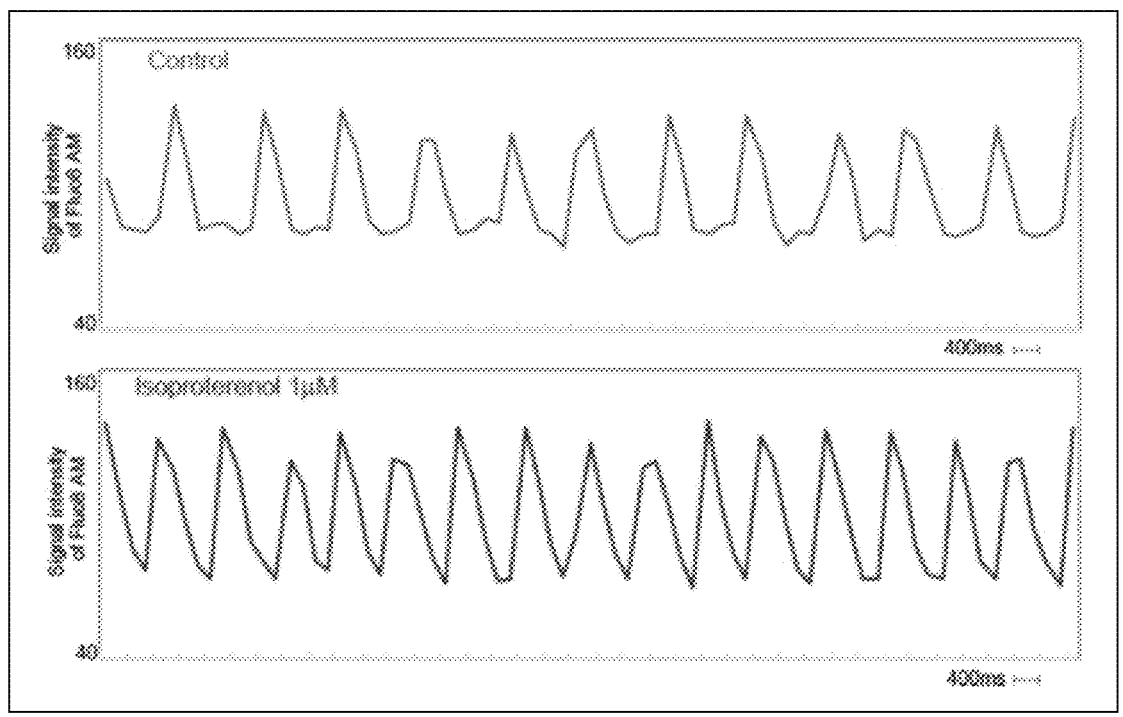

FIG. 40 is a diagram showing the change over time of Ca signal in the mouse ES cell-derived heart organoid of the present invention. In the figure, the upper part shows the results of analyzing a heart organoid in the absence of isoproterenol (Control), and the lower part shows the results of analyzing a heart organoid in the presence of 1 μM isoproterenol.

Figure 41:
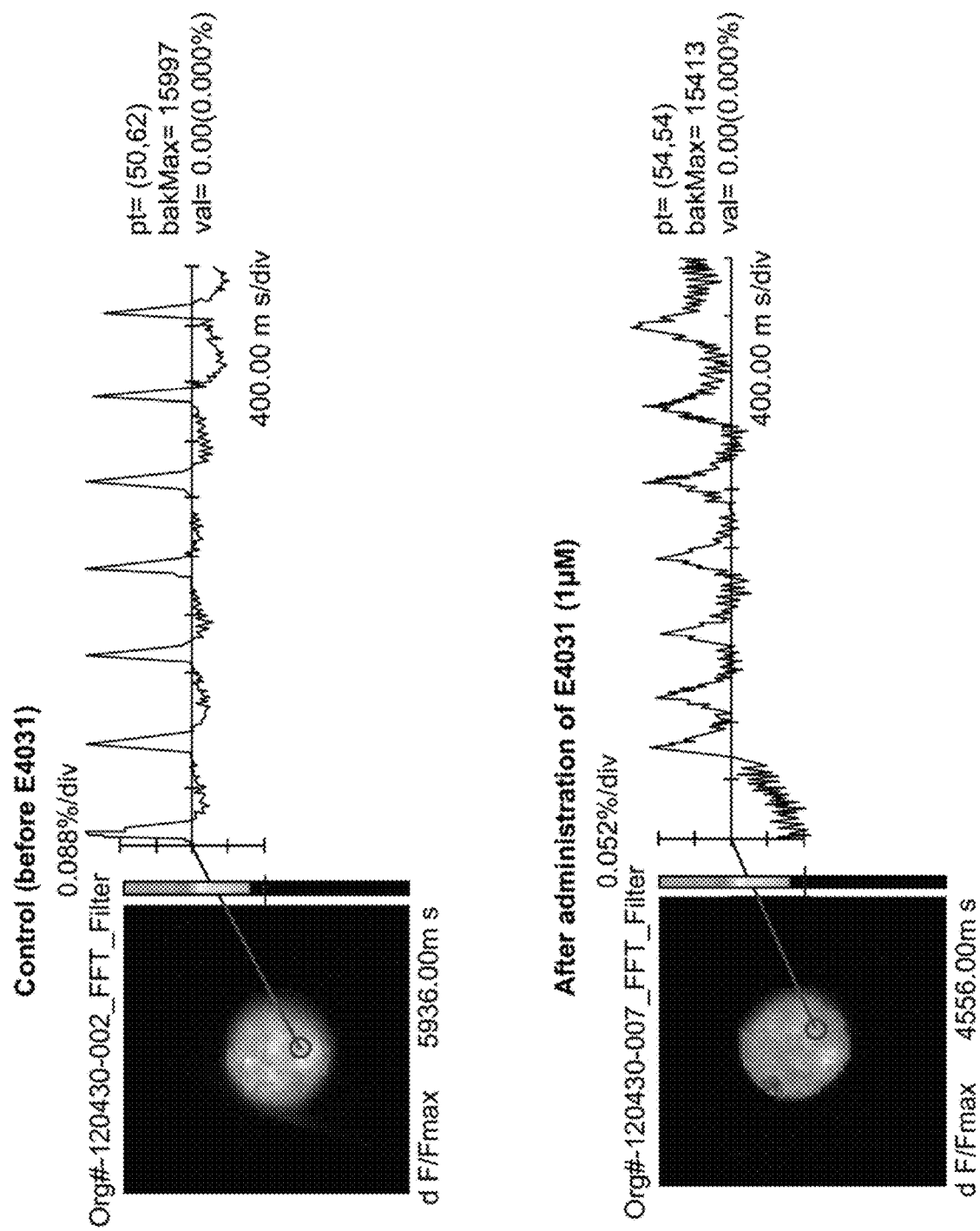

FIG. 41 is a diagram showing the results of electrophysiological analysis of the mouse ES cell-derived heart organoid of the present invention by optical mapping. In the figure, the upper part shows the results of analyzing a heart organoid before addition of E4031 (Control), which is an IKr blocker, and the lower part shows the results of analyzing a heart organoid after addition of 1 μM E4031.

Figure 42:
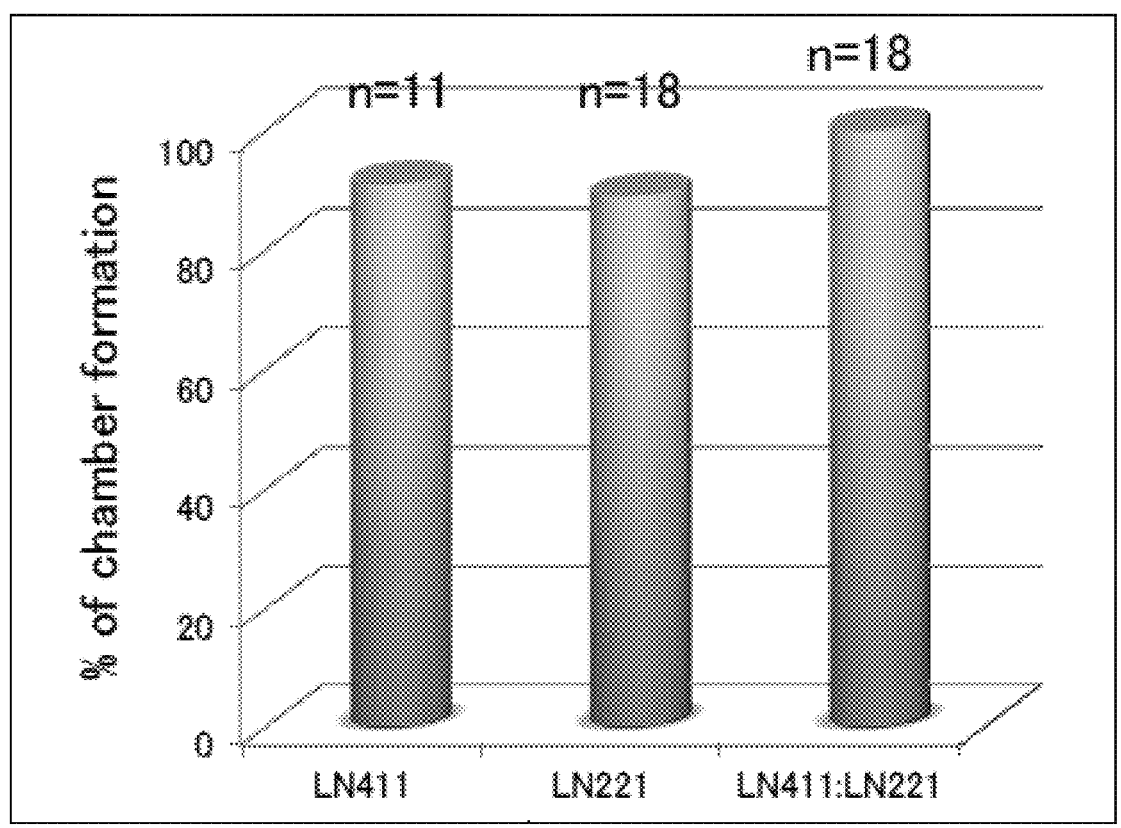

FIG. 42 is a graph showing the percentage of individuals observed to form a cardiac chamber in the mouse ES cell-derived heart organoids of the present invention cultured on the surface of laminin 411 (LN411), laminin 221 (LN221), and a mixture of laminins 221 and 411 in equal amounts (LN411:LN221).

Figure 43:
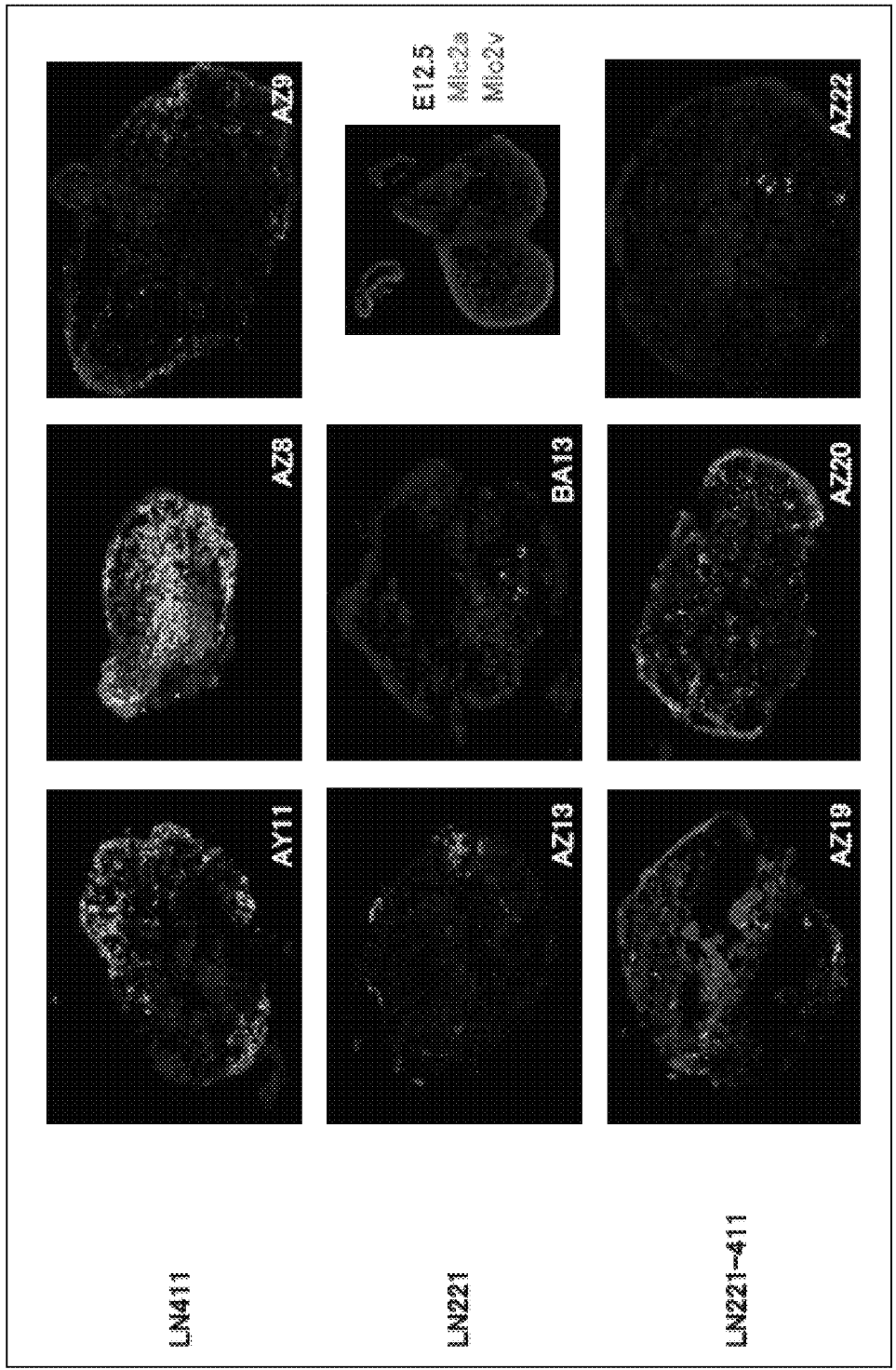

FIG. 43 is a photomicrograph showing the results of detecting the expression of Mlc2a expressed in atrial type myocardium (whose expression is shown in green in the figure) and Mlc2v expressed in ventricular type myocardium (whose expression is shown in red in the figure) in the mouse ES cell-derived heart organoids of the present invention cultured on the surface of laminin 411 (LN411), laminin 221 (LN221), and a mixture of laminins 221 and 411 in equal amounts (LN221-LN411) by immunofluorescent staining. Note that, in the figure, the photograph at the right middle (E12.5) shows the results of analyzing a mouse heart (embryonic day 12.5) by the immunofluorescent staining described above. In addition, the notation at the lower right of each photograph (such as AY11) indicates a sample number optionally assigned to the corresponding heart organoid.

Figure 44:
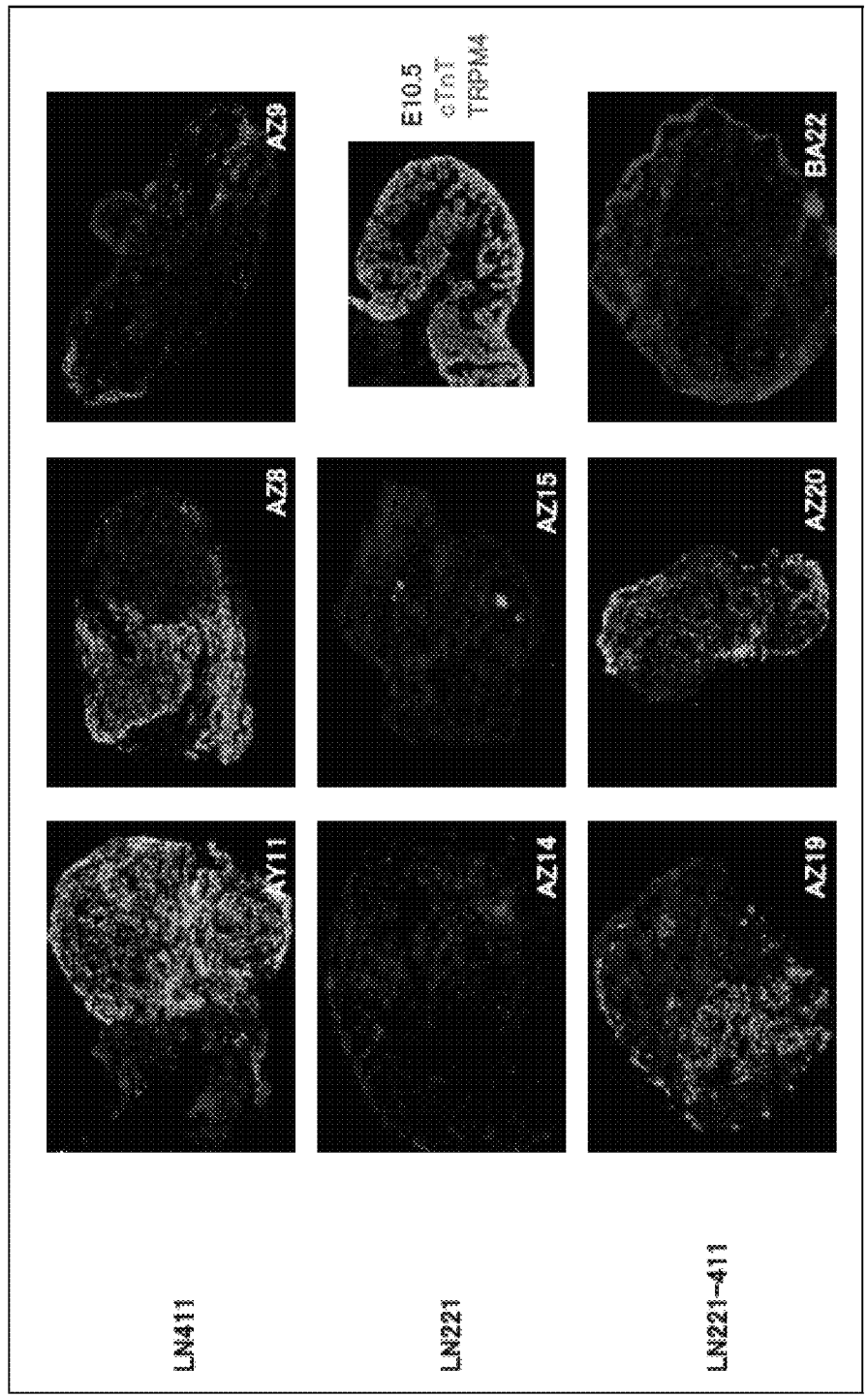

FIG. 44 is a photomicrograph showing the results of detecting the expression of cardiac troponin T (whose expression is shown in green in the figure) and TRPM4 expressed with Purkinje fiber (whose expression is shown in red in the figure) by immunofluorescent staining in the mouse ES cell-derived heart organoid of the present invention cultured on the surface of laminin 411 (LN411), laminin 221 (LN221), and a mixture of laminins 221 and 411 in equal amounts (LN221-LN411). Note that, in the figure, the photograph at the right middle (E10.5) shows the results of analyzing a mouse heart (embryonic day 10.5) by the immunofluorescent staining described above.

Figure 45:
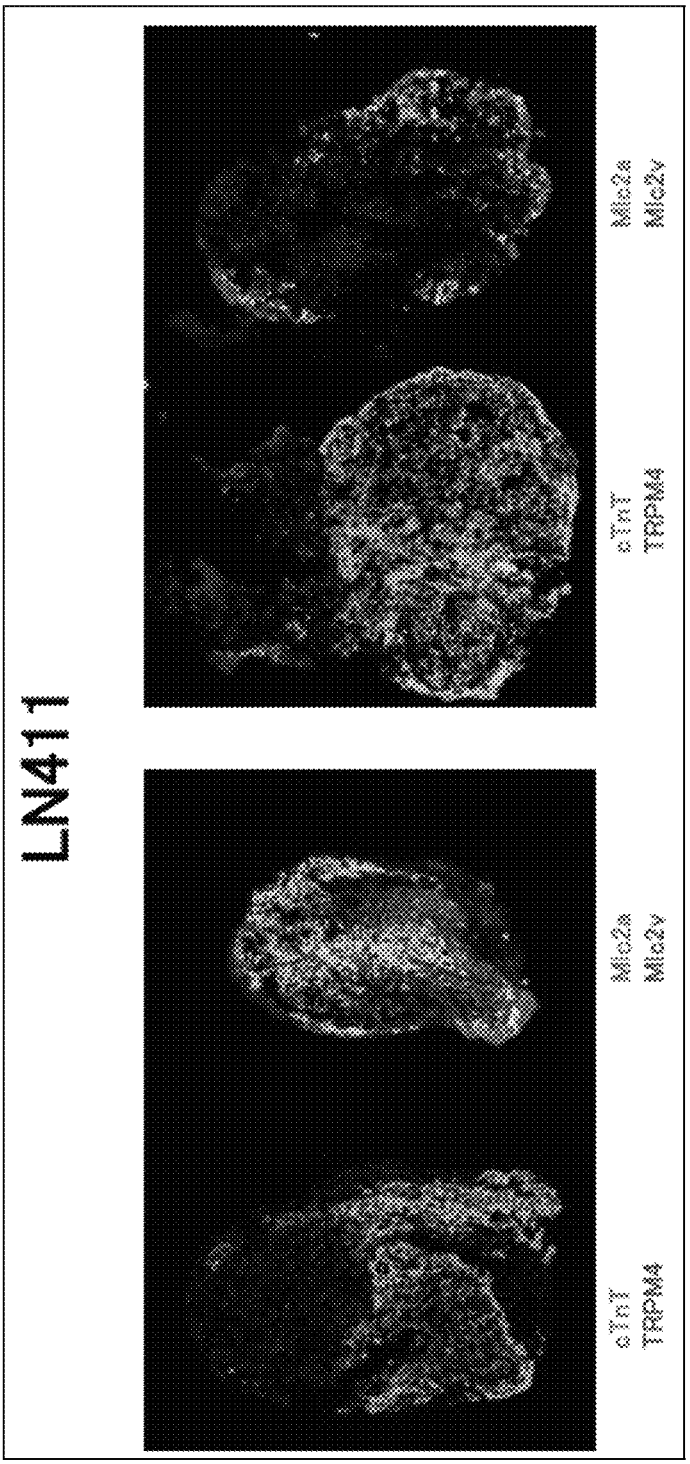

FIG. 45 is a diagram showing photomicrographs of the heart organoid "AZ8" in FIGS. 43 and 44 (two photographs on the left in FIG. 45), and photomicrographs of the heart organoid "AY11" in FIGS. 43 and 44 (two photographs on the right in FIG. 45).

Figure 46:
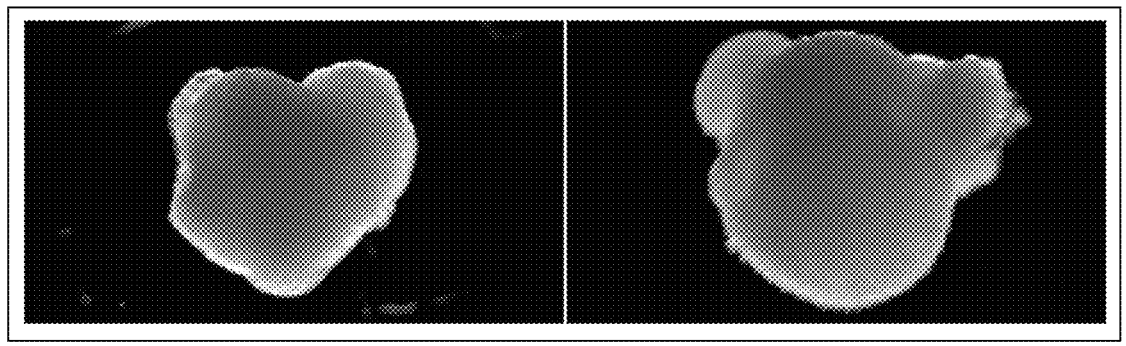

FIG. 46 provides photomicrographs showing the results of observing heart organoids obtained by culturing embryoid bodies on the surface of laminin 11-entactin (LN/ET complex) in the presence of FGF4 for 10 days and then culturing them on laminin 411 or a mixture of laminin 411 and laminin 111 until day 21 in the present invention. The two photographs in the figure show the results of observing two independently obtained heart organoid samples.

Figure 47:
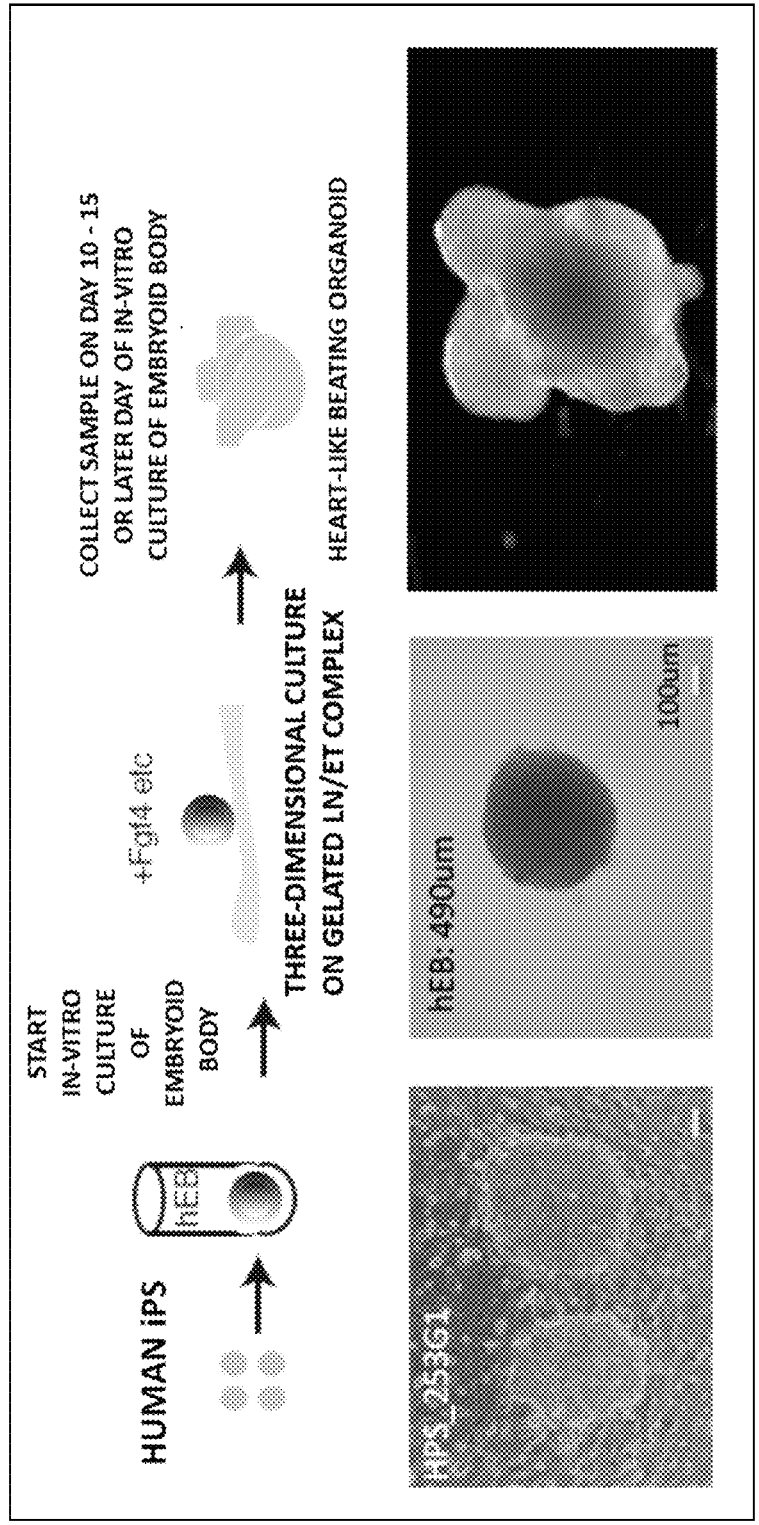

FIG. 47 is a diagram showing an overview of the process of producing a heart organoid from human iPS cells of the present invention (upper stage), and photomicrographs of the organoids and the like observed in the steps (lower stage).

Figure 48:
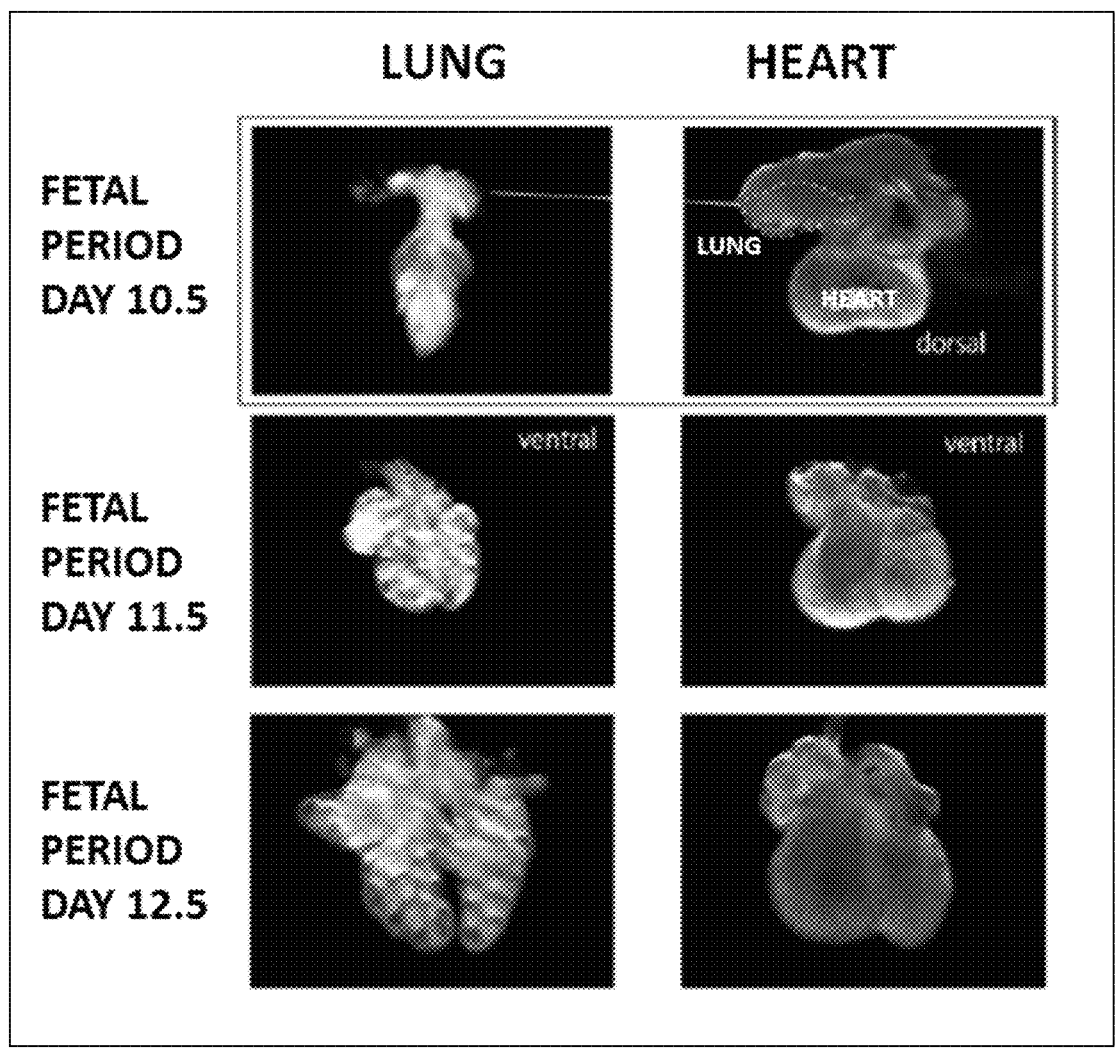

FIG. 48 provides photomicrographs showing the results of observing the developmental stages of the lung and heart of a mouse fetus (fetal period (embryonic), 10.5 to 12.5 days).

Figure 49:
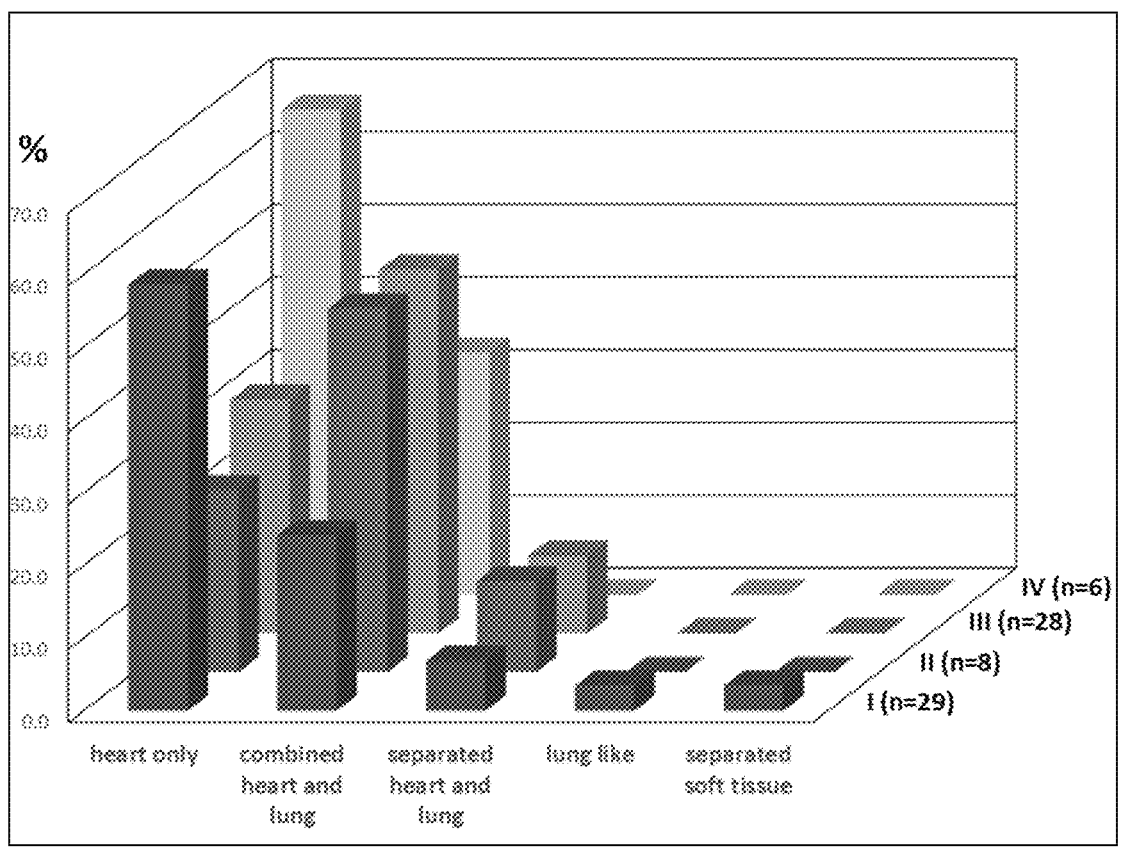

FIG. 49 is a graph showing the types and percentages of organoids obtained by induction from human iPS cells under conditions I to IV. See Table 1 for the conditions "I, II, III, IV" shown in the figure. In addition, "heart only" indicates that only heart organoids were observed at the time of collection (day 13 of culture or later), and "combined heart and lung" indicates that, at the time of collection, organoids were observed with the heart portion connected to the lung portion (see the two photographs on the right of FIG. 50). "Separated heart and lung" indicates that organoids were observed in which the heart and the lung were connected to each other during culture, but the heart and the lung were separated by the time of collection (see the two photographs on the left of FIG. 50). The "lung like" indicates that, at the time of collection, it was not clear whether the organoids were all lung organoids or ones with morphologically connected heart and lung. "Separated soft tissue" indicates that, at the time of collection, the binding force between cells was weak and cells were soft enough to easily cause collapse.

Figure 50:
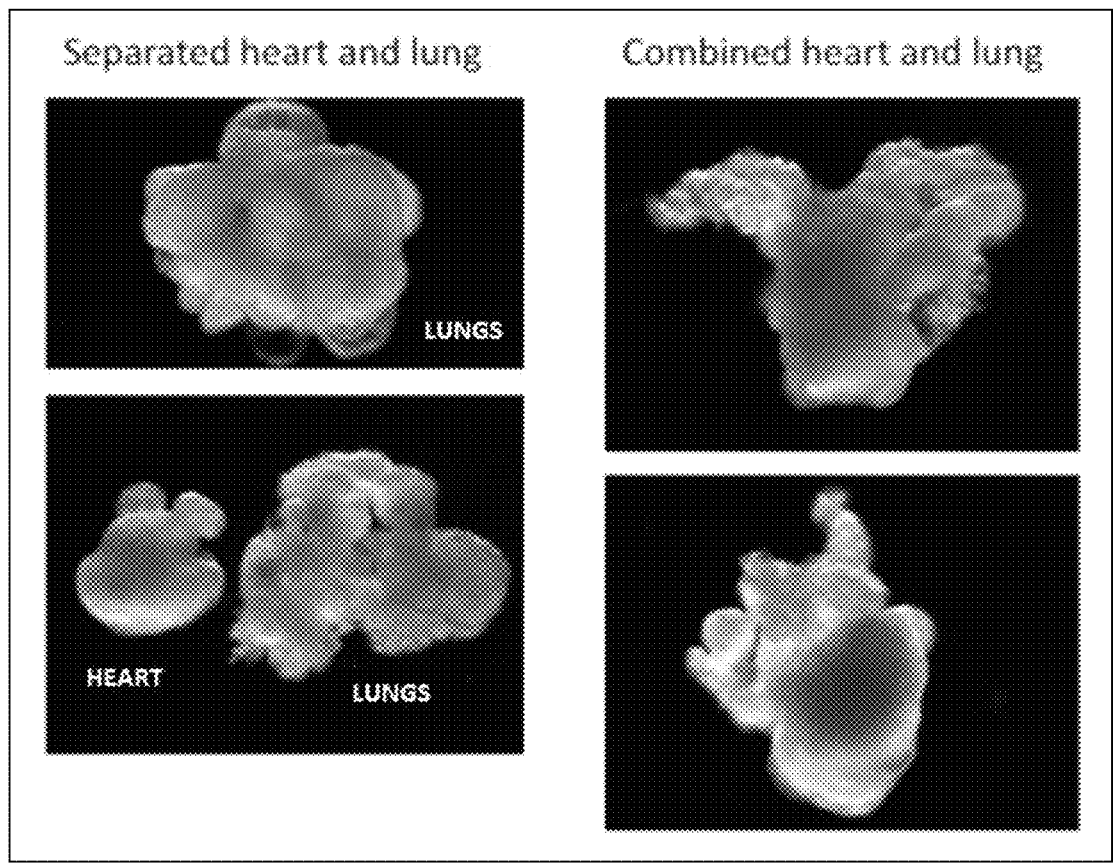

FIG. 50 provides photomicrographs showing the results of observing organoids derived from human iPS cells. In the figure, the two photographs on the left with "Separated heart and lung" show a heart organoid and a lung organoid obtained by separation. Note that the upper photograph shows the results of observing only the lung organoid among the separated organoids. The two photographs on the right with "combined heart and lung" show organoids with the heart portion connected to the lung portion.

Figure 51:
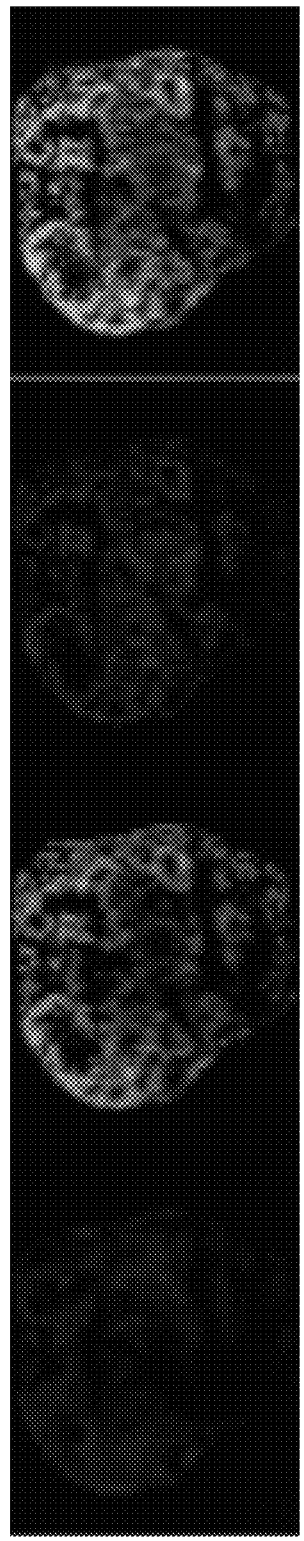

FIG. 51 is a photomicrograph showing the results of detecting the expression of Tbx5 and Nkx2-5 in the human iPS cell-derived heart organoid of the present invention by immunofluorescent staining. In the figure, the expression of Tbx5 is shown in red (the leftmost photograph in the figure), the expression of Nkx2-S is shown in green (the second photograph from the left in the figure), the result of counterstaining with DAPI is shown in blue (the second photo-graph from the right in the figure), and their superposition is shown as the rightmost photograph in the figure.

Figure 52:
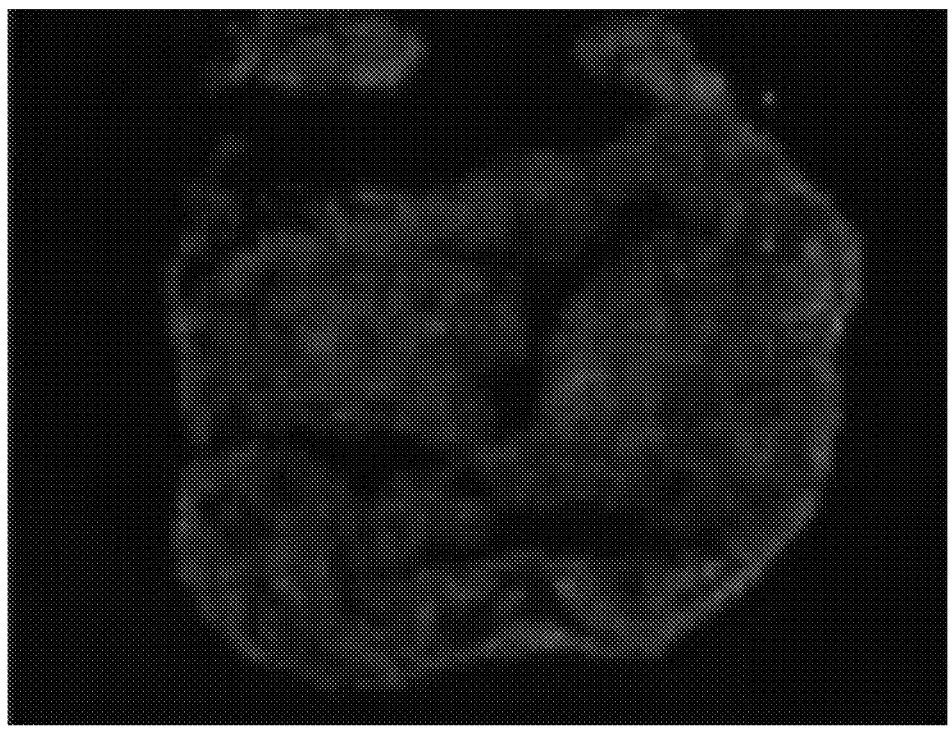

FIG. 52 is a photomicrograph showing the results of detecting the expression of Mlc-2v and Mlc-2a in the human iPS cell-derived heart organoid of the present invention by immunofluorescent staining. In the figure, the expression of Mlc-2v is shown in green, the expression of Mlc-2a is shown in pink, and the result of counterstaining with DAPI is shown in blue.

Figure 53:
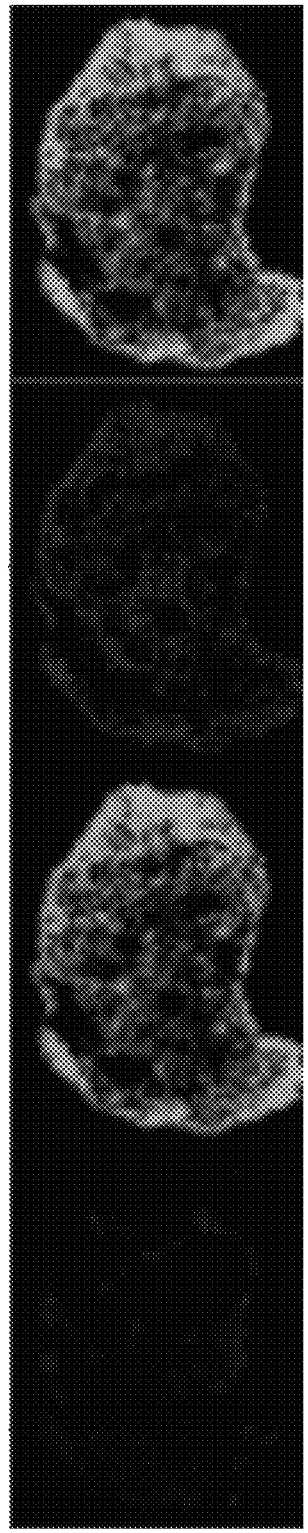

FIG. 53 is a photomicrograph showing the results of detecting the expression of PECAM and cardiac troponin I in the human iPS cell-derived heart organoid of the present invention by immunofluorescent staining. In the figure, the expression of PECAM is shown in red (the leftmost photograph in the figure), the expression of cardiac troponin I is shown in green (the second photograph from the left in the figure), the result of counterstaining with DAPI is shown in blue (the second photograph from the right in the figure), and their superposition is shown as the rightmost photograph in the figure.

Figure 54:
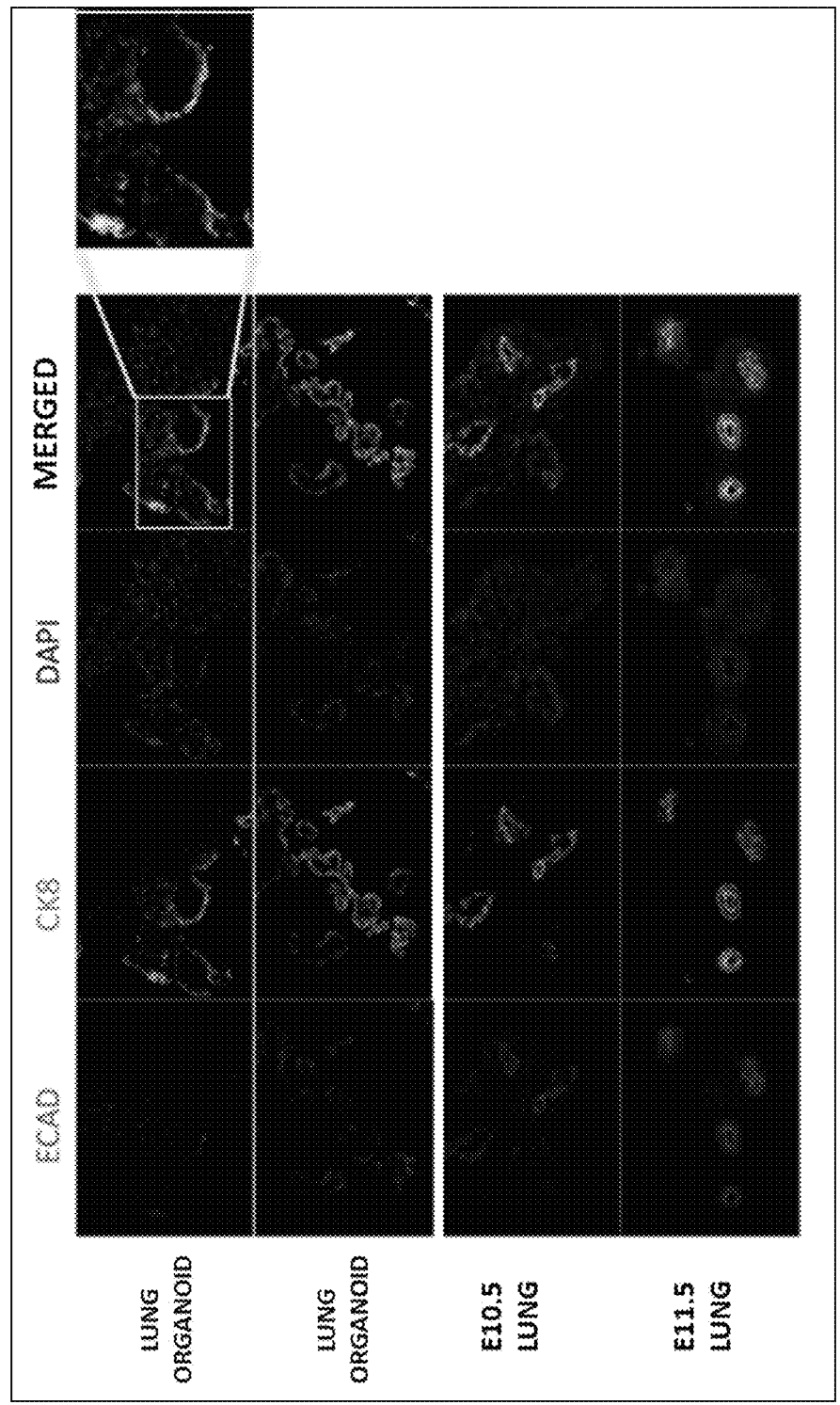

FIG. 54 provides fluorescence photomicrographs showing the results of detecting the expression of tracheal epithelial marker ECAD (whose expression is shown in red in the figure) and Cytokeratin 8 (CK8) (whose expression is shown in green in the figure) by immunofluorescent staining in human iPS cell-derived lung organoids of the present invention and mouse lungs (embryonic day 10.5 and embryonic day 11.5).

DESCRIPTION OF EMBODIMENTS

<Method for Producing Heart Organoids and/or Lung Organoids>

The method for producing heart organoids and/or lung organoids of the present invention (hereinafter also referred to as "cardiac and other organoids") is characterized in that it comprises culturing an embryoid body in the presence of an FGF protein on a surface of a gel containing an extracellular matrix constituent protein.

In the present invention, the "organoid" means an organ-like structure produced in vitro. More specifically, the "heart organoid" means a heart-like structure produced in vitro, having at least one ventricle and one atrium, and capable of performing rhythmic contractions. The "lung organoid" means a lung-like structure having an alveolar structure produced in vitro.

In the present invention, the gel for culturing the later-described embryoid body on the surface thereof may be any gel containing an extracellular matrix constituent protein, and examples thereof include a gel obtained by dissolving an extracellular matrix constituent protein in a buffer solution. The concentration of extracellular matrix constituent protein in the buffer solution is not particularly limited as long as a gel can be formed. However, the adhesiveness and elasticity of the gel can hinder cell migration, proper patterning, and self-organization that occur during the process of differentiation from embryoid bodies to cardiac and other organoids. Therefore, from the viewpoint of suppressing the hindrance, the concentration of extracellular matrix constituent protein in the buffer solution is preferably 0.5 to 20 mg/mL, more preferably 1 to 10 mg/mL, further preferably 2 to 6 mg/mL, and particularly preferably 3 to 4 mg/mL. In addition, the buffer solution is not particularly limited, and a buffer solution having a pH of 6 to 8 (preferably a buffer solution having a pH of 7 to 7.5) is usually used. Moreover, examples of the pH-adjusted buffer solution include a phosphate buffer solution, a Tris buffer solution, and a HEPES buffer solution.

The protein contained in the gel of the present invention may be any protein constituting the extracellular matrix, and its origin is not particularly limited. The protein may be derived from human cells, or may be derived from cells of a non-human animal (such as rodents such as mice and rats, mammals such as cattle, horses, pigs, sheep, monkeys, dogs, and cats, and birds such as chickens). From the viewpoint that a large amount of extracellular matrix constituent proteins can be synthesized, a secretory product from a mouse Engelbreth-Holm-Swarm (EHS) tumor is preferably used. In addition, from the viewpoint of applying the cardiac and other organoids of the present invention to regenerative medicine in humans, it is preferable to use xeno-free extracellular matrix constituent proteins.

Examples of the "extracellular matrix constituent protein" include laminin, entactin (nidogen 1), fibronectin, collagen, proteoglycan, vitronectin, elastin, fibrillin, and tenascin. The gel of the present invention may contain at least one kind of such protein, but may contain two or more kinds thereof. Moreover, when two or more kinds are contained, these different extracellular matrix constituent proteins may be contained in the gel in the form of a hetero complex. In addition, the gel of the present invention may be in a form containing no collagen or proteoglycan. Furthermore, among these extracellular matrix constituent proteins, from the viewpoint that the efficiency of differentiation induction into cardiac and other organoids is more likely to increase, a protein containing laminin and/or entactin is preferable, and a complex composed of laminin and entactin is more preferable. In that case, the content ratio of laminin and entactin in the gel is not particularly limited, but in a molar ratio, laminin:entactin is preferably 30 to 70:70 to 30, more preferably 40 to 60:60 to 40, and particularly preferably 50:50.

Laminin is a heterotrimeric molecule having three subunit chains (α-chain, β-chain, and γ-chain) associated with one another, and moreover, the α-chain is classified into α1- to 5-subunits, the β-chain is classified into β1- to 3-subunits, and the γ-chain is classified into γ1- to 3-subunits. The "laminin" of the present invention is not particularly limited as long as it is a heterotrimeric molecule composed of the subunits or a partial fragment thereof, and examples thereof include laminin 111 (α1-chain, β1-chain, and γ1-chain), laminin 211 (α2-chain, β-chain, and γ1-chain), laminin 121 (α1-chain, β2-chain, and γ1-chain), laminin 221 (α2-chain, β2-chain, and γ1-chain), laminin 332 (α3-chain, β3-chain, and γ2-chain), laminin 311 (α3-chain, β1-chain, and γ1-chain), laminin 321 (α3-chain, β2-chain, and γ1-chain), laminin 411 (α4-chain, β1-chain, and γ1-chain), laminin 421 (α4-chain, β2-chain, and γ1-chain), laminin 511 (α5-chain, β1-chain, and γ1-chain), laminin 521 (α5-chain, β2-chain, and γ1-chain), laminin 213 (α2-chain, β1-chain, and γ3-chain), laminin 423 (α4-chain, β2-chain, and γ3-chain), laminin 523 (α5-chain, β2-chain, and γ3-chain), laminin 333 (α3-chain, β3-chain, and γ3-chain), and a partial fragment thereof. The laminin according to the present invention may be a mixture of these heterotrimeric molecules (for example, a mixture of laminin 411 and laminin 221). In addition, the gel of the present invention preferably contains laminin 111, laminin 411, or a partial fragment thereof from the viewpoint that the efficiency of differentiation induction into cardiac and other organoids is more likely to increase, and more preferably contains laminin 411 or a partial fragment thereof and further preferably the E8 fragment of laminin 411 (the binding site of laminin 411 to integrin α6β1 protein) from the viewpoint that self-organization with normal regionality acquired is more likely to occur in heart organoid formation.

In the present invention, the embryoid body is cultured on the surface of the above-described gel. Specifically, in the present invention, the embryoid body is cultured while a part thereof is brought into contact with the surface of the gel without being completely embedded (enclosed) or dispersed in the gel. The culturing is usually achieved by mounting and culturing the embryoid body on the surface of an incubator covered with the gel of the present invention. The incubator coated with the gel of the present invention is not particularly limited as long as it is a cell culturing incubator capable of culturing embryoid bodies, and can be appropriately selected depending on the purpose. Examples thereof include slides, multiplates, microwell plates, Petri dishes, flasks, and dishes. The concentration of the gel of the present invention on the surface of the incubator may be appropriately adjusted depending on the type of the gel used, and is not particularly limited, but is preferably 0.1 to 100 μg/cm$^2$.

In the production of cardiac and other organoids, the culture of embryoid bodies on the gel surface is performed in the presence of an FGF protein. The "FGF protein" in the present invention may be any FGF protein that can bind to FGFR1 (IIIc) and FGFR2 (IIIc), and examples thereof include fibroblast growth factor 4 (FGF4) and fibroblast growth factor 2 (FGF2, bFGF). Since FGF4 (206 amino acids) is larger than bFGF (164 amino acids), FGF4 is preferable from the viewpoint that the dimer formation of FGFR is easily induced, and further that the downstream signal transduction is more easily activated.

In addition, the origin of the FGF protein is not particularly limited, and may be derived from humans or non-human animals. Moreover, a partial fragment thereof may be used as long as the embryoid body can be induced to differentiate into cardiac and other organoids. The culture in the presence of an FGF protein is usually achieved by adding an FGF protein to the medium. The concentration of the FGF protein added to the medium may be any concentration that can induce differentiation of embryoid bodies into cardiac and other organoids, and the lower limit thereof is preferably 1 ng/mL or more, more preferably 3 ng/mL or more, and further preferably 10 ng/mL or more (for example, 20 ng/mL or more, 30 ng/mL or more, 40 ng/mL or more, 50 ng/mL or more, and 60 ng/mL or more). In addition, the upper limit thereof is preferably 300 ng/mL or less, more preferably 100 ng/mL or less, and further preferably 80 ng/mL or less (for example, 70 ng/mL or less, 60 ng/mL or less, 50 ng/mL or less, and 40 ng/mL or less). Preferred examples of the range of concentration of the FGF protein added to the medium include 1 to 100 ng/mL, more preferably 10 to 80 ng/mL, and further preferably 20 to 70 ng/mL. In addition, from the viewpoint that heart organoids and lung organoids are easily induced simultaneously, the concentration of the FGF protein added to the medium is preferably 10 to 50 ng/mL, and more preferably 20 to 40 ng/mL.

In addition, as described above, the culture method for inducing differentiation of embryoid bodies into cardiac and other organoids in the present invention may be culture on the surface of a gel containing an extracellular matrix constituent protein in the presence of an FGF protein, and other culture conditions can be used by those skilled in the art by appropriately selecting a known embryoid body culture method.

For example, the medium used in culture for inducing differentiation of embryoid bodies into cardiac and other organoids (hereinafter also referred to as the "medium for inducing differentiation into cardiac and other organoids") can be prepared based on a known basal medium for culturing embryoid bodies. Examples of the known basal medium include DMEM medium, Ham's F12 medium, KSOM medium, Eagle's MEM medium, Glasgow MEM medium, αMEM medium, Ham medium, RPMI 1640 medium, Fisher's medium, BME medium, BGJb medium, CMRL 1066 medium, MEM Zinc optional improvement medium, IMDM medium, Medium 199 medium, and any mixed medium thereof.

The medium for inducing differentiation into cardiac and other organoids may be a serum-containing medium or a serum-free medium. The serum-free medium refers to a medium that does not contain unprepared or unpurified serum, and includes a medium containing purified blood-derived components and animal tissue-derived components (for example, growth factors). In addition, the medium for inducing differentiation into cardiac and other organoids may contain a serum replacement. Examples of the serum replacement include commercially available products such as KnockOut Serum Replacement (KSR manufactured by Invitrogen), Chemically Defined Lipid Concentrate (manufactured by Gibco), and GlutaMAX (manufactured by Gibco).

In addition, the medium for inducing differentiation into cardiac and other organoids may contain the FGF protein described above as well as amino acids (such as L-glutamine and non-essential amino acids), hormones (such as progesterone and β-estradiol), growth factors (such as insulin, transferrin, selenite, and ITS), reducing agents (such as β-mercaptoethanol), antibiotics (such as penicillin and streptomycin), organic acids (such as pyruvic acid, sodium pyruvate, and lactic acid), fatty acids or lipids, saccharides, vitamins, cytokines, antioxidants, buffer agents, inorganic salts, and the like.

In addition, depending on the differentiation stage, the medium for inducing differentiation into cardiac and other organoids may be further added with at least one substance selected from the group consisting of growth factors (GSK-3 inhibitors such as BIO (6' bromoindirubin 3' oxime) and Wnt activators such as Wnt1, Wnt3, Wnt3a, Wnt4, Wnt7a, BMP4, BMP2, BMP6, and BMP7), ROCK (Rho-binding kinase) inhibitors (Y-27632), and leukemia inhibitory factors (LIF). In addition, from the viewpoint that heart organoids and lung organoids are easily induced simultaneously, it is preferable to further add an Rho-binding kinase inhibitor (Y-27632).

For example, in the production of heart organoids using human iPS cell-derived embryoid bodies, 3 to 300 ng/mL and preferably 30 ng/mL or more of FGF protein (for example, FGF4), and 1 to 100 μM and preferably 5 to 15 μM (for example, 10 μM) of Y27632 (Rho-binding kinase inhibitor) can be contained in the medium for inducing differentiation into cardiac and other organoids.

In addition, for example, in the production of heart organoids and lung organoids using human iPS cell-derived embryoid bodies, 1 to 100 ng/mL and preferably 20 to 40 ng/mL of FGF protein (for example, FGF4) or 3 to 300 ng/mL and preferably 40 to 80 ng/mL of FGF protein (for example, FGF4) and 1 to 100 μM and preferably 5 to 15 μM (for example, 10 μM) of Y27632 (Rho-binding kinase inhibitor) can be contained in the medium for inducing differentiation into cardiac and other organoids.

In addition, for example, in the production of heart organoids using mouse cell-derived embryoid bodies, 3 to 300 ng/mL and preferably 20 to 70 ng/mL (for example, 30 ng/mL) of FGP protein (for example, FGF4 or bFGF), 5 to 500 ng/mL and preferably 10 to 100 ng/mL (for example, 50 ng/mL) of BMP protein (for example, BMP4), and 100 to 10000 u/mL and preferably 500 to 5000 u/mL (for example, 1000 u/mL) of LIF can be contained in the medium for inducing differentiation into cardiac and other organoids. Moreover, the medium may contain 0.25 to 25 μM, and preferably 1 to 5 μM (for example, 2.5 μM) of GSK-3 inhibitor (for example, BIO (Wnt activator)).

In addition, the culture period for inducing differentiation of embryoid bodies into cardiac and other organoids is not particularly limited, and can be appropriately adjusted by those skilled in the art according to the origin of the embryoid body used and the like. However, from the viewpoint that it is easier to obtain a heart organoid having a cardiac chamber formed therein and a lung organoid having alveoli, the period is preferably 5 to 30 days, more preferably 7 to 20 days, and further preferably 9 to 15 days.

Note that, preferably, the embryoid bodies are cultured on a gel containing laminin 111 and entactin for 8 to 12 days, and thereafter cultured on a gel containing laminin 411 from the viewpoint that production and long-term culture of mature heart organoids become easier, as presented in Examples described later.

Moreover, other conditions for inducing differentiation of embryoid bodies into cardiac and other organoids can be appropriately selected and adjusted by those skilled in the art according to known culture conditions for embryoid bodies. For example, the culture temperature is not particularly limited, but is usually about 30 to 40° C., and preferably about 37° C. The concentration of $CO_2$ is usually about 1 to 10%, and preferably about 2 to 5%. The oxygen concentration is usually 1 to 10%.

In the present invention, the "embryoid body" subjected to the above-described culture means an aggregate formed of differentiated cells and undifferentiated cells obtained by suspension culture of pluripotent stem cells or overgrowth in monolayer culture.

In the present invention, the "pluripotent stem cells" used for forming embryoid bodies may be any cells having a pluripotent differentiation self-renewal ability, and examples thereof include cells that can be collected from a living body, such as embryonic stem cells (ES cells), epiblast stem cells (EpiS cells), embryonal carcinoma cells (EC cells), embryonic germ cells (EG cells), multipotent germline stem cells (mGS cells), and MUSE cells (see Kuroda Y. et al., Proc. Natl. Acad. Sci. U.S.A., 2010, Volume 107, Issue 19, pages 8639 to 8643). Moreover, the "pluripotent stem cells" also include cells artificially induced to have pluripotency and the like from somatic cells collected from a living body, such as induced pluripotent stem cells (iPS cells and the like).

In addition, the origin of these cells is not particularly limited, and includes humans and non-human animals. Moreover, if the origin of the cells is a patient suffering from a heart disease, the present invention makes it possible to obtain a heart organoid useful as a heart disease model. As the heart disease, there is a hereditary heart disease, and examples thereof include congenital long QT syndrome (LOTS), Brugada syndrome, familial bradycardia syndrome (sick sinus syndrome, atrioventricular block), catecholaminergic polymorphic ventricular tachycardia (CPVT), short QT syndrome (SQTS), hypertrophic cardiomyopathy, and dilated cardiomyopathy.

In addition, the present invention also makes it possible to obtain a heart organoid useful as a non-hereditary heart disease model. Examples of the non-hereditary heart disease include coronary artery diseases (myocardial infarction), congenital heart diseases (ventricular septal defect, atrial septal defect, tetralogy of Fallot), and hypertension. Those skilled in the art can reproduce these non-hereditary heart diseases by appropriately preparing (adding or excluding)

components to be added to the culture system (medium) of heart organoids (compounds such as myocardial infarction inducers, inhibitors, hormones, and nutrients), or by changing the physical conditions of the culture system (such as temperature and salt concentration).

In addition, the present invention makes it possible to obtain a lung organoid useful as a lung disease model by defining the origin of the cells as a patient suffering from a lung disease. Examples of the lung disease include hereditary interstitial lung disease such as familial interstitial pneumonia, congenital pulmonary alveolar albinism, and childhood-onset interstitial pneumonia. In addition, examples of non-hereditary lung diseases include idiopathic interstitial pneumonia (Designated Intractable Disease 85). Interstitial pneumonia is characterized by the fact that the walls of the originally thin alveolar wall become thick and hard (fibrosis) and gas exchange is not successful. Therefore, it is considered that addition of an agent that or the like induces pulmonary fibrosis to the lung organoid in the present invention enables the in-vitro reproduction of interstitial pneumonia.

In addition, the "pluripotent stem cells" of the present invention may be cells that have been genetically modified (genetically modified cells), such as αMHC-GFP ES cells used in Examples to be described later. The genetically modified cells may be cells exogenously introduced with a gene encoding a protein to be expressed such as GFP in the αMHC-GFP ES cells, may be cells in which the function of a specific gene is suppressed by genome editing, knockout method, RNA method, antisense method, or the like, or may be cells in which the function of a gene is randomly suppressed or activated. Examples of the cells in which the function of a gene is randomly suppressed or activated include cells treated with a chemical mutagen such as EMU, EMS, NMU, and NTG, cells introduced with a DNA-cleaving enzyme such as zinc finger nuclease or TALEN, cells irradiated with fast neutrons, gamma rays, or ion beams, and cells in which transposons are randomly inserted into genomic DNA. Moreover, the genetic modification may be performed after the cells are established, or may be performed before establishment, for example, at the individual stage of collecting the unfertilized egg or the sperm. In addition, a gene mutation causing the disease may be introduced by genetic modification.

In the present invention, the number of pluripotent stem cells provided for forming an embryoid body is not particularly limited as long as the embryoid body can be formed, and can be appropriately adjusted by those skilled in the art according to the type and origin of the pluripotent stem cells, and usually 50 to 50000. However, from the viewpoint that the later morphogenetic steps (formation of a looping heart tube and a cardiac chamber) are reached, and a heart organoid having rhythmic contractile ability is more easily obtained, the number of pluripotent stem cells for forming one embryoid body is preferably 100 to 10000, more preferably 500 to 7000, and more preferably 1000 to 5000.

The method for culturing pluripotent stem cells is not particularly limited as long as embryoid bodies can be formed, and may be adhesion culture or non-adhesion culture (for example, suspension culture such as coagulation suspension culture and suspension culture on a carrier). Those skilled in the art can appropriately select a known embryoid body culturing method, but from the viewpoint of forming the embryoid body into a spherical shape, suspension culture is preferable.

In addition, the medium used in such culture can be prepared based on a known basal medium for culturing pluripotent stem cells. Examples of the known basal medium include DMEM medium, KSOM medium, Eagle's MEM medium, Glasgow MEM medium, aMEM medium, Ham medium, RPMI 1640 medium, Fisher's medium, BME medium, BGJb medium, CMRL 1066 medium, MEM Zinc optional improvement medium, IMDM medium, Medium 199 medium, and any mixed medium thereof. In addition, a commercially available culture medium for culturing ES cells or iPS cells is also preferably used.

The medium for forming an embryoid body may be a serum-containing medium or a serum-free medium, or may contain a serum replacement. In addition, it is possible to contain amino acids (such as L-glutamine and non-essential amino acids), reducing agents (such as β-mercaptoethanol), antibiotics (such as penicillin and streptomycin), hormones, growth factors, organic acids, fatty acids or lipids, saccharides, nucleosides, vitamins, cytokines, antioxidants, buffer agents, inorganic salts, and the like.

Note that, although LIF is usually added to the above-described medium during the maintenance culture of pluripotent stem cells, it is preferable not to add LIP in the present invention from the viewpoint that culture for forming embryoid bodies requires differentiation induction, not maintenance of pluripotency.

As the incubator used for culture to form embryoid bodies, known ones used for culturing pluripotent stem cells and the like can be appropriately used, and in order to perform suspension cells, a non-adhesive (low-adsorption) incubator is preferable. Examples of the incubator include multiplates, microwell plates, petri dishes, flasks, and dishes coated with a hydrophilic compound or a water-soluble resin.

In addition, the culture period for forming embryoid bodies is not particularly limited, and can be appropriately adjusted by those skilled in the art according to the type and origin of the pluripotent stem cells to be used, and is usually 1 to 14 days, preferably 2 to 7 days, and more preferably 3 to 5 days.

Moreover, other conditions for forming embryoid bodies can be appropriately selected and adjusted by those skilled in the art according to known culture conditions. For example, the culture temperature is not particularly limited, but is usually about 30 to 40° C., and preferably about 37° C. The concentration of $CO_2$ is usually about 1 to 10%, and preferably about 2 to 5%. The oxygen concentration is usually 5 to 21%.

<Kit for Producing Cardiac and Other Organoids>

In addition, the present invention also provides a kit used for producing the above-described cardiac and other organoids. The kit of the present invention comprises at least the above-described gel containing an extracellular matrix constituent protein, the above-described medium for culturing an embryoid body (medium for inducing differentiation into cardiac and other organoids), and an PGF protein to be added to the medium. In addition, the kit of the present invention may include a solution containing an extracellular matrix constituent protein before gelation instead of or in combination with the gel.

In addition, the kit of the present invention may further include LIP, BMP, and the like to be added to the medium, and may further include the embryoid body described above. Moreover, in order to enable the production of cardiac and other organoids from pluripotent stem cells through embryoid bodies, the kit of the present invention may include the above-described medium for forming an embryoid body from pluripotent stem cells, and the pluripotent stem cells.

In addition, the kit of the present invention can also include materials for producing the cardiac and other organoids as well as a reagent for confirming that the produced structures are the cardiac and other organoids. Examples of the reagent include an antibody that recognizes a cell-specific marker constituting an organ, and a labeled secondary antibody that recognizes the antibody. In addition, in the case of a heart organoid, an intracellular calcium indicator that emits green fluorescence may be used, as in Examples to be described later. Moreover, the kit of the present invention can include instructions for using the kit.

<Cardiac and Other Organoids>

As shown in Examples to be described later, the heart organoid and the lung organoid produced by the above-described method reproduce the structure responsible for their functions in vivo. In particular, in the heart organoid, the regionality of various cells faithfully reproduces that in a living body, and also exerts functions such as myocardial contraction. Then, as described later, use of that organoid enables screening of a compound for treating, ameliorating, or preventing a disease relating to the corresponding organ or a compound having toxicity to the organ, and further enables regenerative medicine for diseases and the like related to the organ.

Therefore, the present invention also provides heart organoids, lung organoids, or fragments or cells of these organoids obtained by culturing an embryoid body on the surface of a gel containing an extracellular matrix constituent protein at least in the presence of an FGF protein. In addition, in some aspects, the organoids, fragments, or cells thereof may be for use in transplantation into a living body.

In the present invention, the "organoid fragments" may be any part of the organoid. In a heart organoid, examples thereof include ventricles and atria, and in a lung organoid, examples thereof include alveoli. In addition, the "organoid cells" may be any cells that constitute an organoid. In a heart organoid, examples thereof include vascular endothelial cells, cardiomyocytes, and smooth muscle cells, and in a lung organoid, examples thereof include alveoli cells.

Note that, unlike a normal heart, the heart organoid of the present invention is a structure in which the blood inlet and outlet are closed. In addition, the size of the heart organoid of the present invention is not particularly limited and can be appropriately adjusted according to the size of the embryoid body subjected to the production method of the present invention, the number of pluripotent stem cells subjected to the formation of the embryoid body, and the like. Therefore, in the present invention, it is possible to provide a heart organoid having a size of 400 to 1200 μm (for example, 600 to 1000 μm, 700 to 900 μm), for example. In the present invention, the size of the heart organoid means the longest diameter.

In addition, the lung organoid of the present invention has a structure similar to an alveolus or an alveolar duct formed by connecting two or more alveoli. In the present invention, it is possible to provide a lung organoid having a size of 1 mm or more (for example, 1 to 1.6 mm), for example. Note that the size of the lung organoid is not particularly limited as in the case of the heart organoid described above, and can be appropriately adjusted.

Further, as shown in Examples to be described later, the present invention makes it possible to obtain a heart organoid and a lung organoid in a connected form. Therefore, the present invention also provides a conjugate of a heart organoid and a lung organoid.

<Evaluation Method Using Cardiac and Other Organoids>

As shown in Examples to be described later, the heart organoid of the present invention faithfully reproduces the structure and function of the heart in a living body. In addition, the lung organoid of the present invention has alveoli, which are an important structure for exerting its function. Therefore, these organoids are useful for evaluating the toxic activity of a compound on the corresponding organ. Particularly with respect to the heart, these organoids may be useful because prolonged QT by drugs is also associated with sudden death. In addition, with respect to lung organoid, it is also effective in evaluating whether a newly developed drug (particularly anticancer drug) has side effects of drug-induced pneumonia or pulmonary fibrosis (evaluation of pulmonary toxicity).

Therefore, the present invention provides a method for evaluating toxicity of a compound to a heart, comprising the steps of: bringing the heart organoid of the present invention into contact with a test compound to detect a condition of the heart organoid; and judging that the test compound is a compound having toxicity to the heart if deterioration is observed in the condition detected in the previous step.

Moreover, the present invention provides a method for evaluating toxicity of a compound to a lung, comprising the steps of: bringing the lung organoid of the present invention into contact with a test compound to detect a condition of the lung organoid; and judging that the test compound is a compound having toxicity to the lung if deterioration is observed in the condition detected in the previous step.

In addition, as described above, if the origin of the cardiac and other organoids of the present invention is a patient suffering from diseases relating to the corresponding organs, and further if the content components and/or physical conditions of the culture system of the cardiac and other organoids are adjusted, it is possible to use the organoids as a model for the diseases.

Therefore, the present invention provides a method for evaluating therapeutic activity of a compound on a heart disease, comprising the steps of: bringing the heart organoid of the present invention exhibiting a heart disease into contact with a test compound to detect a condition of the heart organoid; and judging that the test compound is a compound having therapeutic activity on the heart disease if a therapeutic effect on the heart disease is observed in the condition detected in the previous step.

Moreover, the present invention provides a method for evaluating therapeutic activity of a compound on a lung disease, comprising the steps of: bringing the lung organoid of the present invention exhibiting a lung disease into contact with a test compound to detect a condition of the lung organoid; and judging that the test compound is a compound having therapeutic activity on the lung disease if a therapeutic effect on the lung disease is observed in the condition detected in the previous step.

The "heart organoid" and "lung organoid" used in the evaluation method of the present invention are as described above, but the entirety of these organoids may be subjected to the evaluation method, or apart (fragment) of these organoids or a cell isolated from the organoids may be used.

The "test compound" to be brought into contact with the cardiac and other organoids of the present invention is not particularly limited, and a compound having toxicity to the corresponding organ or a compound having a therapeutic activity on a disease relating to the organ can be screened by using a synthetic low molecular compound library, an expression product of a gene library, a peptide library, an antibody, a bacterial release substance, a cell (microorganism, plant cell, animal cell) extract liquid and culture supernatant, a purified or partially purified polypeptide, an extract from marine organisms, plants, or animals, soil, or a random phage peptide display library.

In addition, the "contact" with cardiac and other organoids can be usually performed by adding a test compound to a medium for culturing (maintaining) the cardiac and other organoids. In addition, as the medium, the above-described medium for inducing differentiation into cardiac and other organoids is preferably used.

The "condition" of the cardiac and other organoids detected in the evaluation method of the present invention is not particularly limited, and examples thereof include the form (appearance and internal form) and functions (such as contraction force, contraction rhythm, and the rate of beats for the heart, and gas exchange for the lung) of the heart and the like. In the evaluation of toxicity, if an abnormality (deterioration) of the form or functions of the heart and the like is observed, the test compound can be judged as a compound having toxicity to the heart and the like. In addition, in the evaluation of therapeutic activity, if an improvement in the form or functions of the heart and the like (therapeutic effect) is observed, the test compound can be judged as a compound having a therapeutic activity on diseases of the heart and the like.

EXAMPLES

Hereinafter, the present invention is described more specifically based on Examples, but the present invention is not limited to the following Examples.
(Cell Culture)

Trypsin-treated ES cells derived from wild-type mice (three different cell lines) and αMHC-GFP ES cells were seeded in 0.2% gelatin-coated wells and incubated at 37° C. for 45 minutes. Next, the suspended ES cells were collected and subjected to a centrifugation treatment at 1000 rpm for 5 minutes.

For the purpose of forming embryoid bodies, 1000 to 5000 ES cells were seeded in one well of a 96-well U-bottom plate (SUMILON Prime Surface (registered trademark) 96 Well U), and cultured in LIF-free FBS-ES medium at 37° C. for 4 days. In addition, for the purpose of examining the minimum number of ES cells required for generating a heart organoid, embryoid bodies were formed using 500 ES cells.

For the purpose of forming heart organoids, the embryoid bodies were transferred onto a chamber slide (manufactured by Falcon, catalog number: 35418) coated with 85.7 µg/cm LN/ET gel (manufactured by BD, catalog number: 354259) together with 200 UL of a heart organoid differentiation induction medium.

Note that the heart organoid differentiation induction medium was DMEM/F12 (manufactured by Gibco, catalog number: 11320033) containing 30 ng/mL or 60 ng/mL FGF4, 50 µg/mL penicillin/streptomycin, 20% KSR, 1 mM sodium pyruvate, 100 µM β-mercaptoethanol, 2 mM L-glutamine, 60 ng/mL progesterone, 30 ng/mL 3-estradiol, 5 µg/mL insulin, 20 µg/mL transferrin, and 30 nM selenite. Note that the concentration of FGF4 added to the medium was 30 ng/mL unless otherwise specified.

Then, the embryoid bodies were cultured at 37° C. and 5% $CO_2$ for 10 to 15 days (medium exchange was performed on days 3, 5, 7, 9, 11, 13, 14, and 15). In addition, from day 9, 50 ng/ml BMP4, 2.5 µM BIO (6' bromoindirubin 3' oxime), and 1,000 units/mL LIF were added to the heart organoid differentiation induction medium and cultured. Moreover, after the culture, the heart organoids were collected for further analysis such as immunofluorescent staining and calcium ion measurement.
(Immunofluorescent Staining)

The heart organoids were collected after 10 to 15 days of culture, subjected to Tissue-Tek (registered trademark) OCT Compound embedment in a plastic tissue mold (CRYO DISH manufactured by SHOEI WORK'S CO., LTD.), and frozen. Frozen sections were prepared to a thickness of 5 to 7 µm using a cryostat at −16° C., and transferred onto a MAS-coated glass slide (manufactured by Matsunami Glass Ind., Ltd.) or a poly-L-lysine-coated slide (manufactured by Sigma-Aldrich). Embryoid bodies that were not subjected to induction of differentiation into heart organoids were also collected, cryo-embedded in OCT, and prepared into sections in the same manner as described above.

In addition, for the purpose of preparing and observing sections of mouse embryonic heart, pregnant female mice (C57BL/6, 9.5 to 13.5 days after sexual intercourse) were sacrificed, and the fetuses at various stages were dissected. Prior to freezing in OCT, the embryonic hearts were immersed in sucrose-PBS solutions (4%, 10%, 15% and 20%). The embryonic hearts frozen in OCT were prepared in cryostats into 7 µm thick sections.

The frozen sections were immersed in 4% paraformaldehyde-PBS at room temperature for 15 minutes and immobilized. The immobilized sections were washed three times in PBS for 5 minutes. Next, the sections were immersed in a blocking buffer (5% normal goat serum and 0.3% Triton-X100, or 5% bovine serum albumin (BSA) and 0.3% Triton-X100) for 1 hour at room temperature. The sections were incubated overnight at 4° C. with the primary antibody diluted in PBS containing 1% BSA and 0.3% Triton-X100. After washing with PBS, the sections were incubated with the secondary antibody for 1 to 2 hours at room temperature.

The slides were counterstained with DAPI (dilution ratio: 1:1000, manufactured by Dojindo Laboratories) and mounted on VECTASHIELD HardSet Anti-Fading Kit (manufactured by Vector Laboratories).

The following antibodies were used as primary antibodies for immunofluorescent staining. Tbx5 (manufactured by Abcam, ab137833), cardiac troponin I (manufactured by Abcam, ab47003), Nkx2-5 (manufactured by Abcam, ab91196), nestin (manufactured by Abcam, ab105389), Oct3/4 (manufactured by Santa Cruz Biotech), PECAM (manufactured by BD), Mlc2a (manufactured by Synaptic System, #311 011), Mlc2v (manufactured by Synaptic System, #310 003), SM-MHC (manufactured by Abcam and manufactured by R&D Systems) and αSMA (ab5694).

In addition, appropriate secondary antibodies (all manufactured by Invitrogen) were used in accordance with the respective primary antibodies.
($Ca^{2+}$ Measurement)

The heart organoids were washed twice with PBS and immersed in a 4 µM green fluorescent intracellular calcium indicator Fluo8 AM (acetoxymethyl) or Fluo8 AM/F127, freshly diluted with Tyrode's solution containing 1.8 mM $Ca^{2+}$, at 37° C. for 15 to 30 minutes. Thereafter, the heart organoids were washed twice with PBS, treated with 200 µL of Tyrode's solution, mounted, and observed with a fluorescence microscope (manufactured by Keyence Corporation).

Note that all animal experiments were approved by the animal experiment committee of Tokyo Medical and Dental University, and were performed according to the guidelines of the committee.

Example 1

\<Formation of Heart Organoid\>

Figure 1:
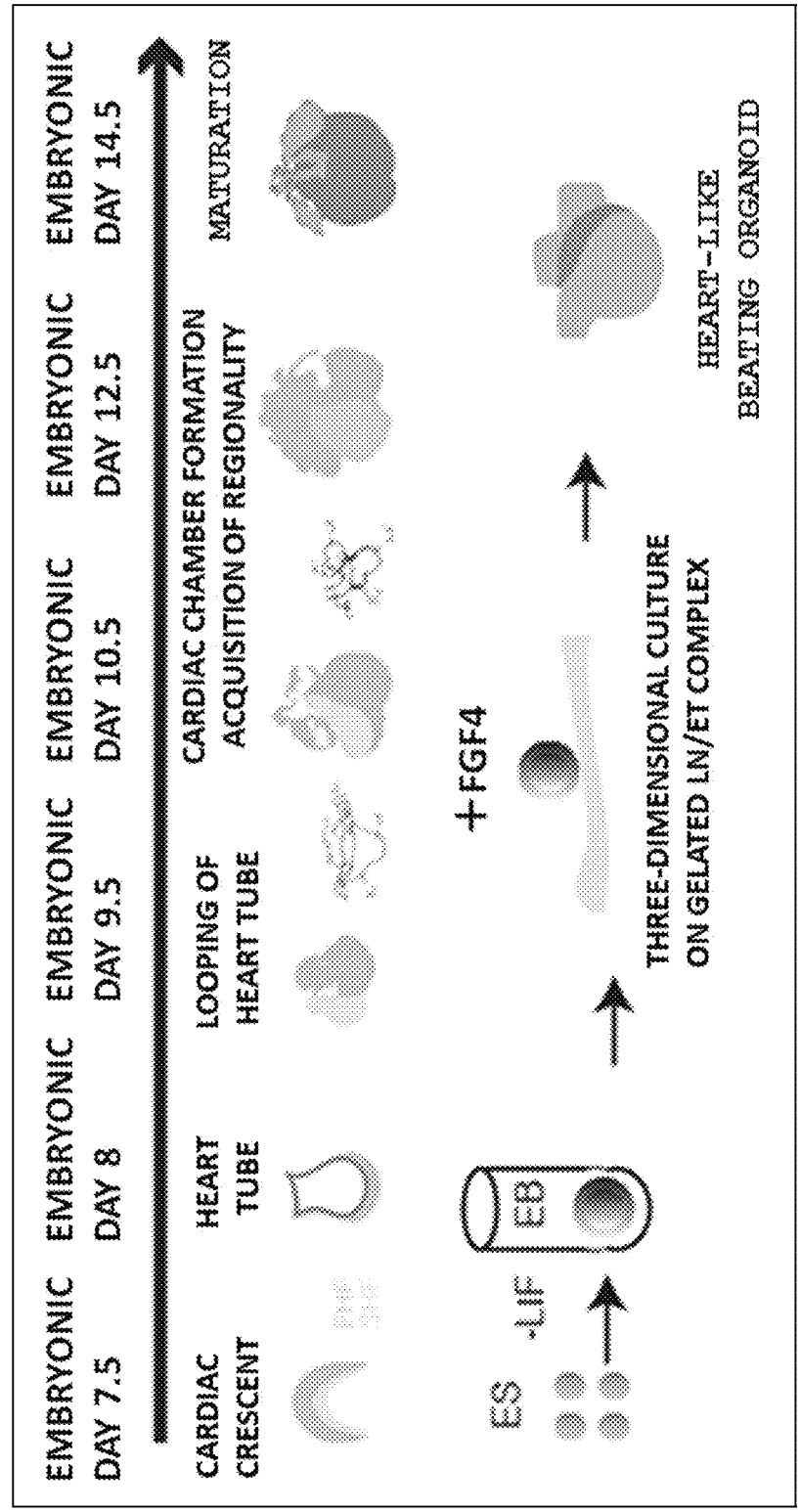
FIG. 1 is a schematic diagram showing the process of forming a heart during mouse embryonic development (upper stage) and the process of producing a heart organoid from mouse BS cells of the present invention (lower stage).

As shown in the upper stage of FIG. 1, during embryonic development, the formation of a heart shows a characteristic morphological change accompanied by differentiation into a wide variety of cells such as vascular endothelial cells, cardiomyocytes, and smooth muscle cells. First, on embryonic day 7.5, the formation of a cardiac crescent including a first heart field and a second heart field is characterized by the expression of cardiac mesoderm genes (Mesp1, Flk1, Pdgfra) induced by the expression of brachyury. Then, on embryonic day 8, a linear beating heart tube is formed. Moreover, on embryonic day 9.5, the heart tube in a tubular shape having vascular endothelial cells in the inner layer and cardiomyocytes in the outer layer loops by beating power or outflow tract (OFT). Then, four cardiac chambers (right atrium, left atrium, right ventricle, and left ventricle) are formed by embryonic day 10.5 and are mature by embryonic day 14.5.

For the purpose of attempting to mimic such a process of developing a heart in the living body, as shown in the lower stage of FIG. 1, first, mouse ES cells were cultured in a low-binding U-bottom 96-well plate in the absence of leukemia inhibitory factor (LIP) to obtain complete embryoid bodies (EB) (1000 to 5000 cells/embryoid body). Then, the resulting embryoid bodies were cultured in the presence of an exogenous FGF signal (FGF4) on the surface of a gelated LN/ET complex containing components of the extracellular matrix (ECM) in the connective tissue.

Note that, although not shown in the figure, the results of the reanalysis of microarray data previously reported by Li, X. et al. (GEO accession No. GDS5003, Li, X. et al., Physiol Genomics 46, 482-495, doi: 10.1152/physiolgenomics.00015.2014 (2014)) revealed dominant expression of Lama1, Lamb1, Lamc1, and Nid1 (entactin) in the embryonic heart. Therefore, it was hypothesized that an LN/ET complex containing laminin $\alpha 1\beta 1\gamma 1$ (laminin-111) derived from Engelbreth-Holm-Swarm tumor was able to provide an ECM environment suitable for cardiac development.

Figure 2:
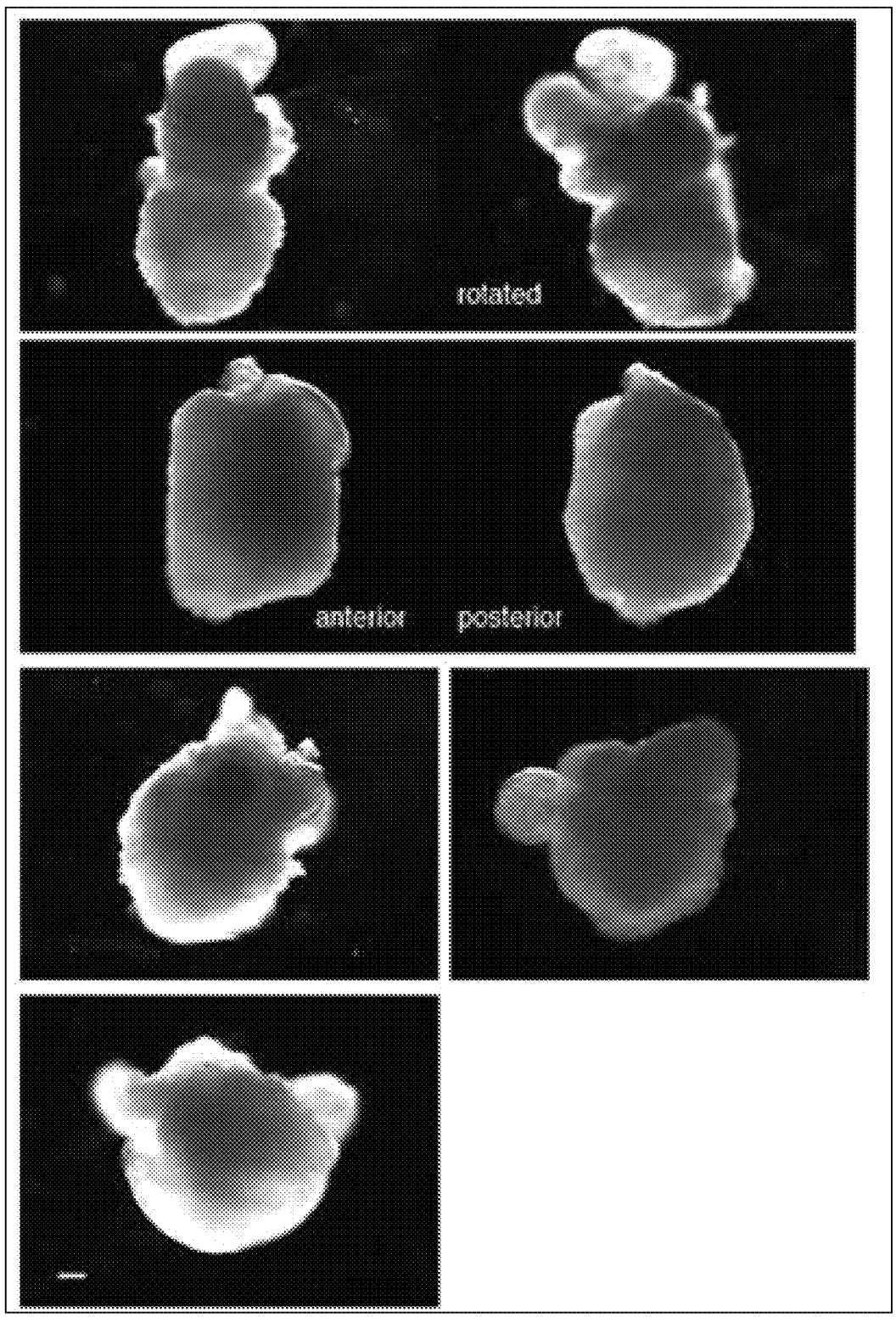
FIG. 2 is a photomicrograph showing a representative example of a mouse ES cell-derived heart organoid produced by the method of the present invention (heart organoid developed by culturing an embryoid body on a gelated laminin (LN)/entactin (ET) complex in the presence of FGF4 for 10 to 11 days). In the figure, the scale bar represents 100 μm.
Figure 3:
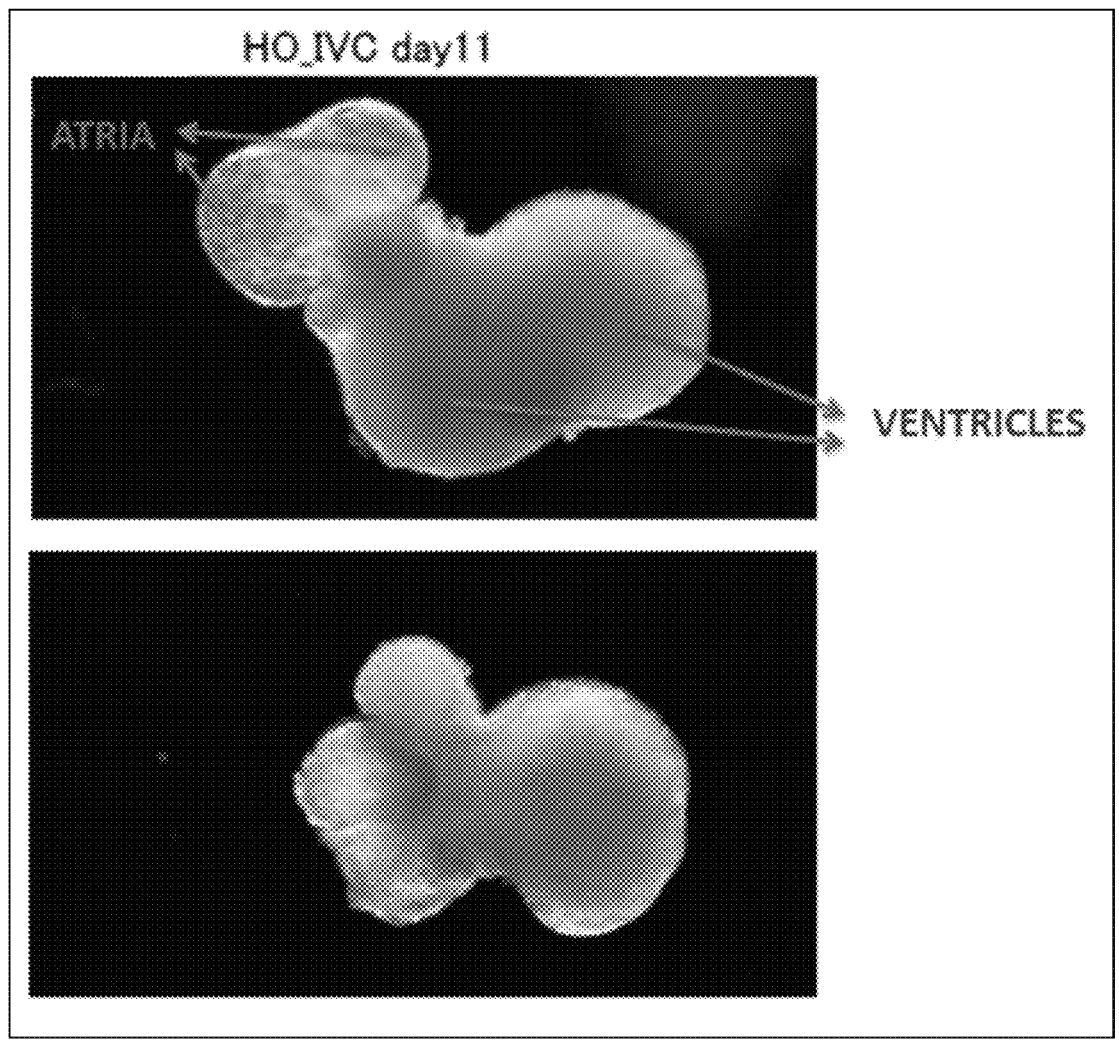
FIG. 3 is a photomicrograph showing a representative example of a mouse ES cell-derived heart organoid (day 11 of culture) produced by the method of the present invention.

The embryoid bodies were cultured in the presence of FGF4 for 8 days throughout, and from day 9, added with BIO (GSK-3 inhibitor, Wnt activator), BMP4, and LIF and cultured for 10 days or more. As a result, as shown in FIG. 2, a beating heart organoid having more than one cardiac chamber and resembling an embryonic heart was successfully produced. In addition, as shown in FIG. 3, it was also confirmed that the mouse ES cell-derived heart organoid produced in this manner had a morphologically two-atrial two-ventricular structure, not a spherical structure exhibiting a mere contractive action.

Note that, although not shown in the figure, culture in the presence of bFGF instead of FGF4 also successfully produced the same beating heart organoid as described above.

Figure 4:
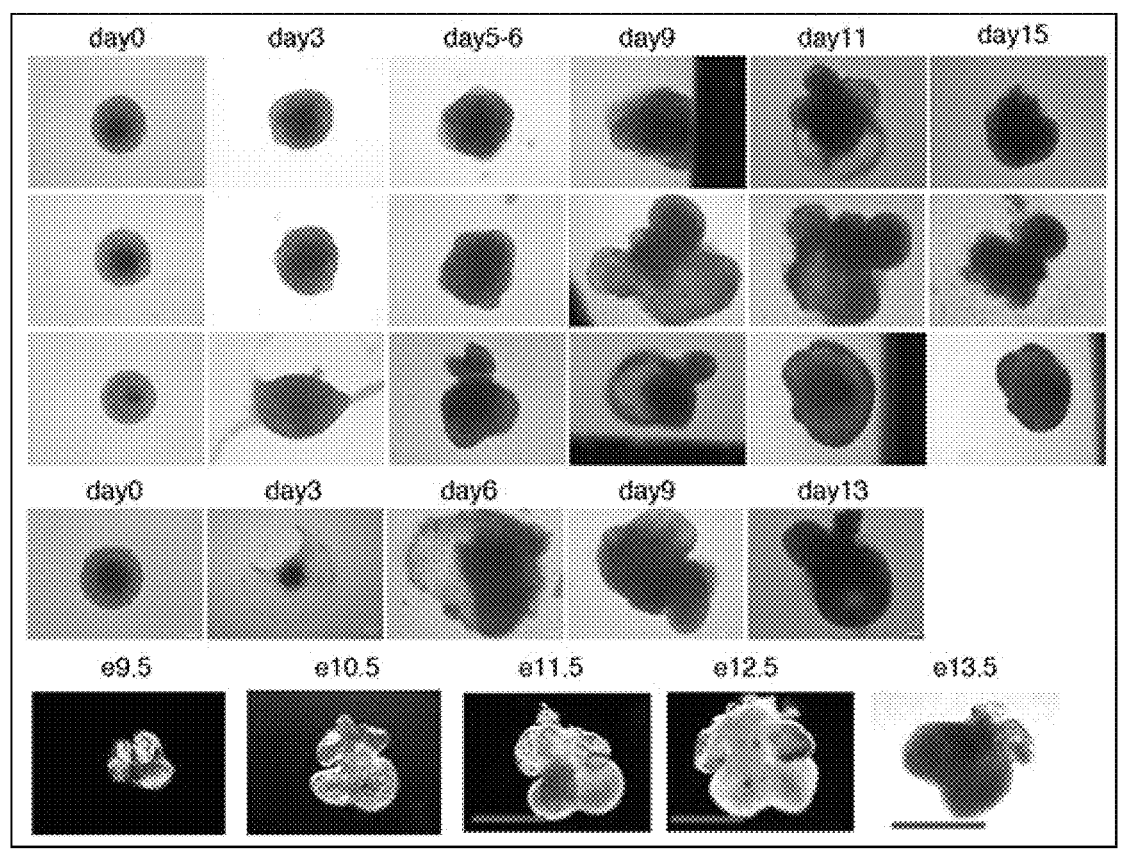
FIG. 4 is a photomicrograph showing the process of forming the mouse ES cell-derived heart organoid of the present invention (day 0 to 15 after culturing an embryoid body on a gelated LN/ET complex in the presence of FGF4), and the process of forming a heart during mouse embryonic development (embryonic days 9.5 to 13.5). In the figure, the scale bar (red) represents 1 mm, and the scale bar (yellow) represents 100 μm.
Figure 5:
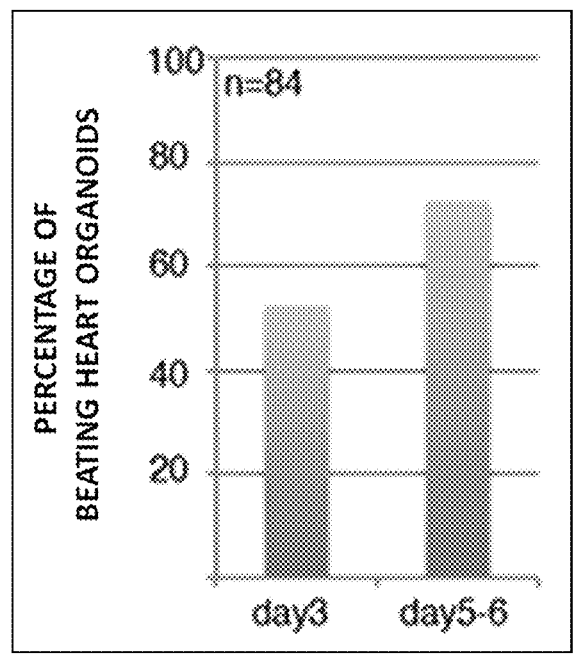
FIG. 5 is a graph showing the percentage of heart organoids exhibiting spontaneous beating (n=84, showing the results of six independent experiments).

In addition, as shown in FIG. 4, the cardiac crescent-like (CCL) structure, the heart tube, and the looping heart tube generated together with the formation of the cardiac chamber were formed in the same order as in the process of developing the embryonic heart. The only exception is the appearance of spheres with buds (Sb) showing some polarity. This may be due to the difference between the precursor structure of the cardiac crescent or heart tube in vivo and the artificial structure due to in-vitro embryoid body culture. In addition, by embryonic day 8 during embryonic development, cardiac progenitor cells move from the first heart field to the midline to form a beating linear heart tube having myocardium. This process, as shown in FIG. 5, is 6 consistent with the detection of naturally occurring beats primarily in heart organoids containing a cardiac crescent-like structure (52.4% on day 3 of culture, 72.6% on day 6 of culture).

Figure 6:
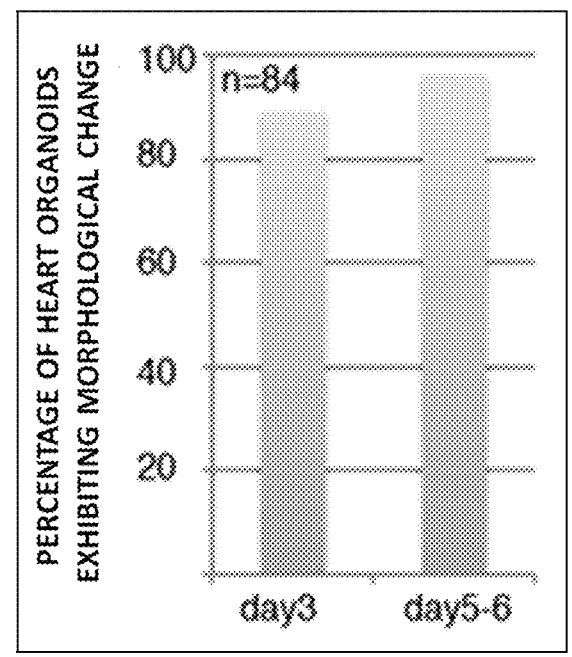
FIG. 6 is a graph showing the percentage of heart organoids exhibiting a morphological change from embryoid bodies (n=, 84, showing the results of six independent experiments).

In addition, as for morphogenesis, the first morphological change was observed on day 3 of culture in the embryoid bodies in a spherical shape (89.3%) as shown in FIG. 6, which mainly included cardiac crescent-like structures derived from the outgrowths of hatched embryoid bodies, resembling the outgrowth and patterning during limb bud formation by Fgf signals (see Powers, C. J. et al., Endocrine-Related Cancer 7, 165-197 (2000)). Further, by day 6 of culture, this change was complete in most embryoid bodies (96.4%).

Figure 7:
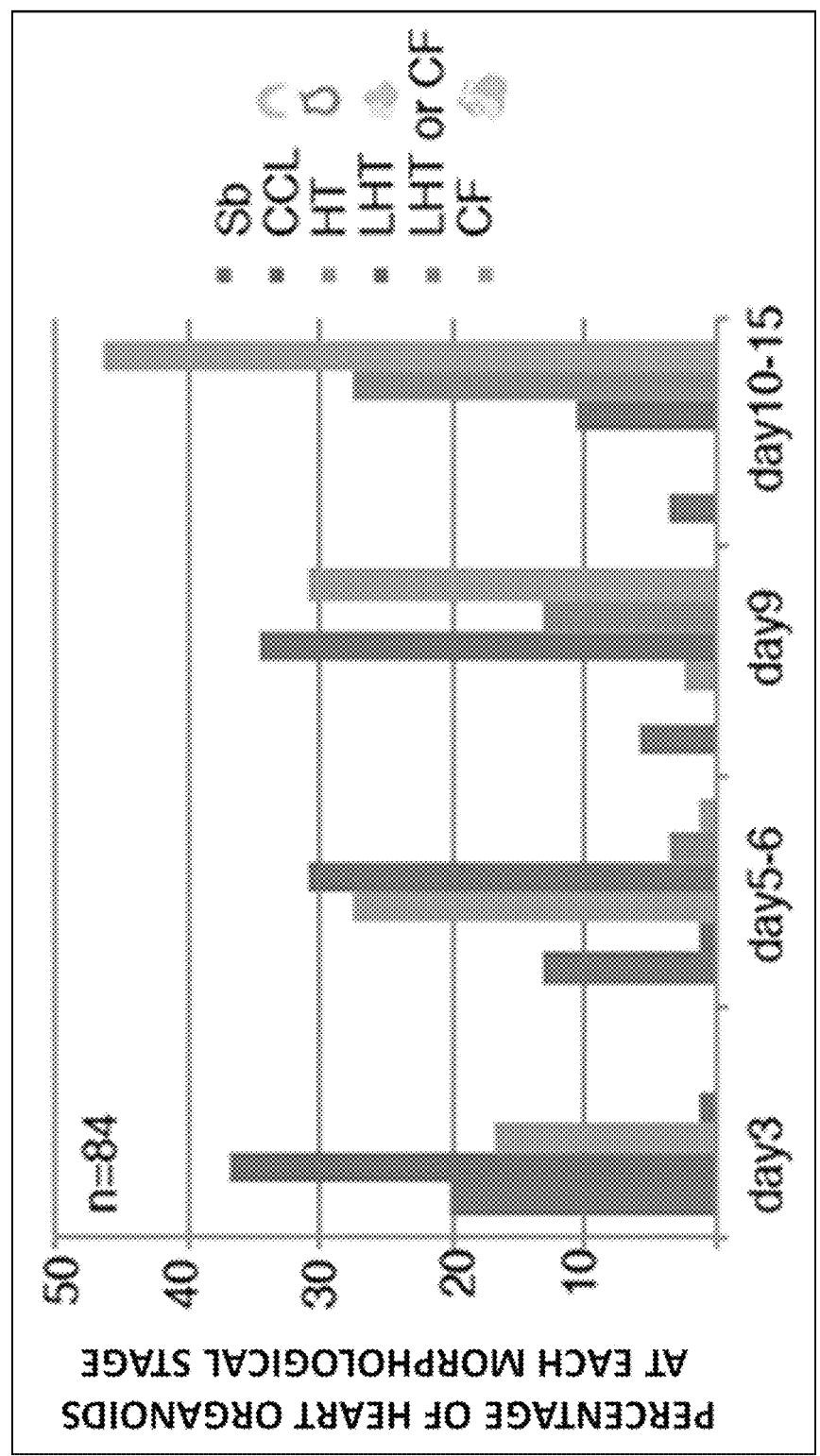
FIG. 7 is a graph showing the frequency of heart organoids with morphological features (n=84, showing the results of six independent experiments). In each of the culture periods (day 3 of culture, days 5 to 6 of culture, day 9 of culture, and days 10 to 15 of culture), the figure shows the percentages of Sb (spherical heart organoid precursors with buds), CCL (heart organoids observed to have a cardiac crescent-like structure), HT (heart organoids forming a heart tube-like structure), LHT (heart organoids forming a looping heart tube-like structure), LHT or CF (heart organoids observed to form a looping heart tube-like structure or to undergo cardiac chamber formation), and CF (heart organoids observed to undergo cardiac chamber formation) in order from the left.

In addition, as shown in FIG. 7, most of the heart organoids were cardiac crescent-like structures on day 3 of culture. These organoids shifted to the formation of a heart tube, a looping heart tube, and a cardiac chamber, and finally reached the formation of a cardiac chamber by days 10 to 15 of culture. This process is also similar to that of heart morphogenesis in vivo.

Thus, interestingly, the formation of heart organoids in this culture system can be said as a summary of the morphological change in embryonic heart development. The reason why such morphological change could be reproduced is not clear, but is assumed as follows. In the present culture system, the extracellular matrix was able to induce efficiently morphogenesis without inhibiting cell migration during the process of forming heart organoids and by reducing mechanical hindrance preventing proper patterning and self-organization.

Figure 8:
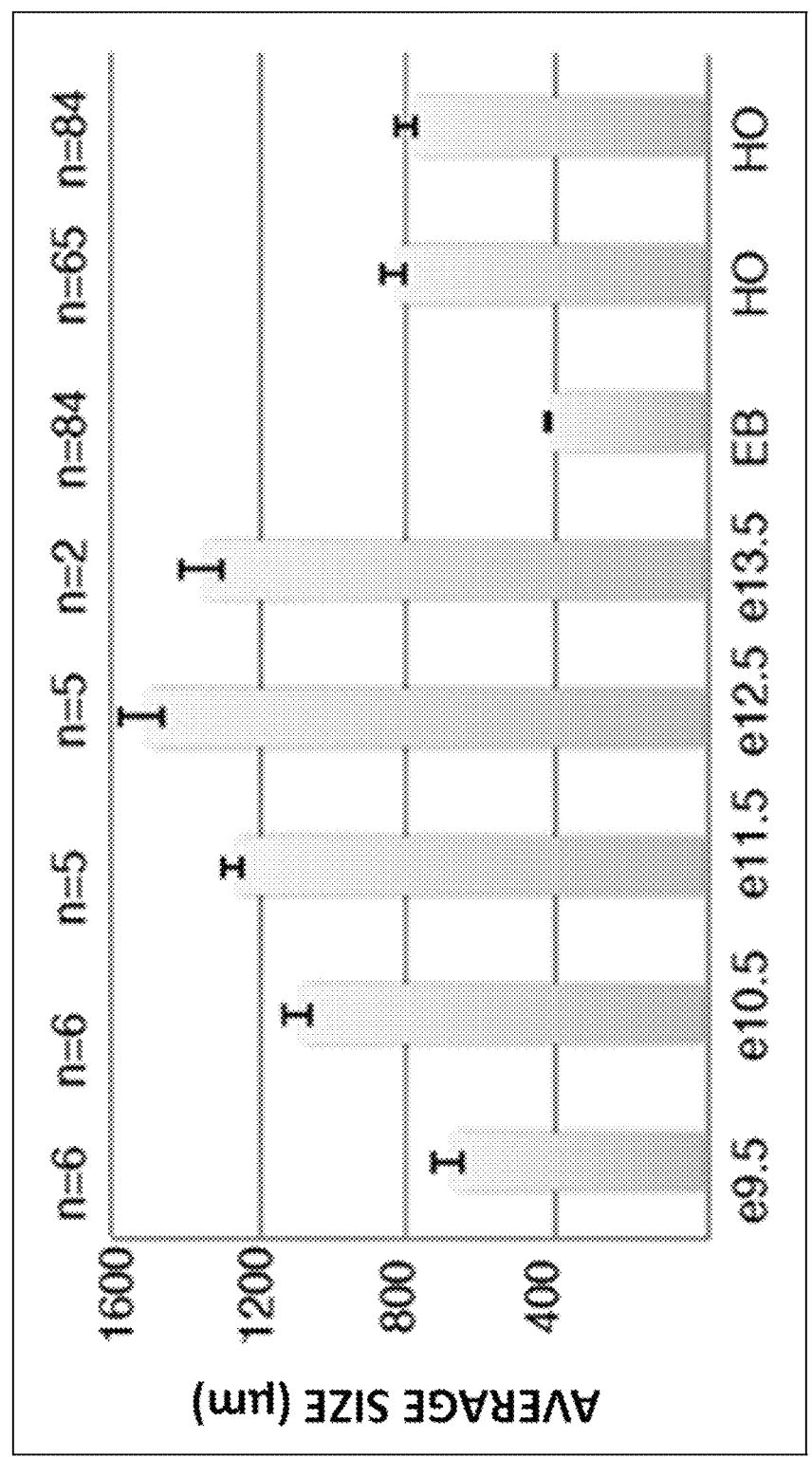
FIG. 8 is a graph showing the average sizes of mouse embryonic hearts (embryonic days 9.5 to 13.5), embryoid bodies (EB), and HO (heart organoids). Note that the size indicates the average value of each major axis.

In addition, as shown in FIG. 8, as a result of comparing the heart organoids obtained by culture (n=84 for all heart organoids, n=65 for heart organoids having a looping heart tube or a cardiac chamber formed therein and heart organoids having a cardiac chamber formed therein) with the embryonic hearts on embryonic days 9.5 to 13.5, the heart organoids were larger than the embryonic hearts on embryonic day 9.5. The results suggest that substantial cellular proliferation is associated with morphogenesis.

In addition, for the purpose of determining whether the initial cell number was a limiting factor for the efficiency of heart organoid generation, embryoid bodies derived from small numbers of cells (500 cells) were also cultured to attempt to induce differentiation into heart organoids (n=11).

Figure 9:
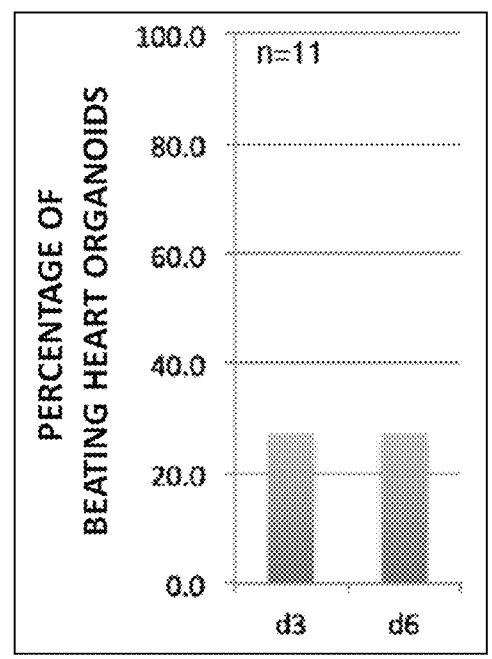
FIG. 9 is a graph showing the percentage of heart organoids exhibiting spontaneous beating in the process of producing heart organoids of the present invention using 500 mouse ES cells.
Figure 10:
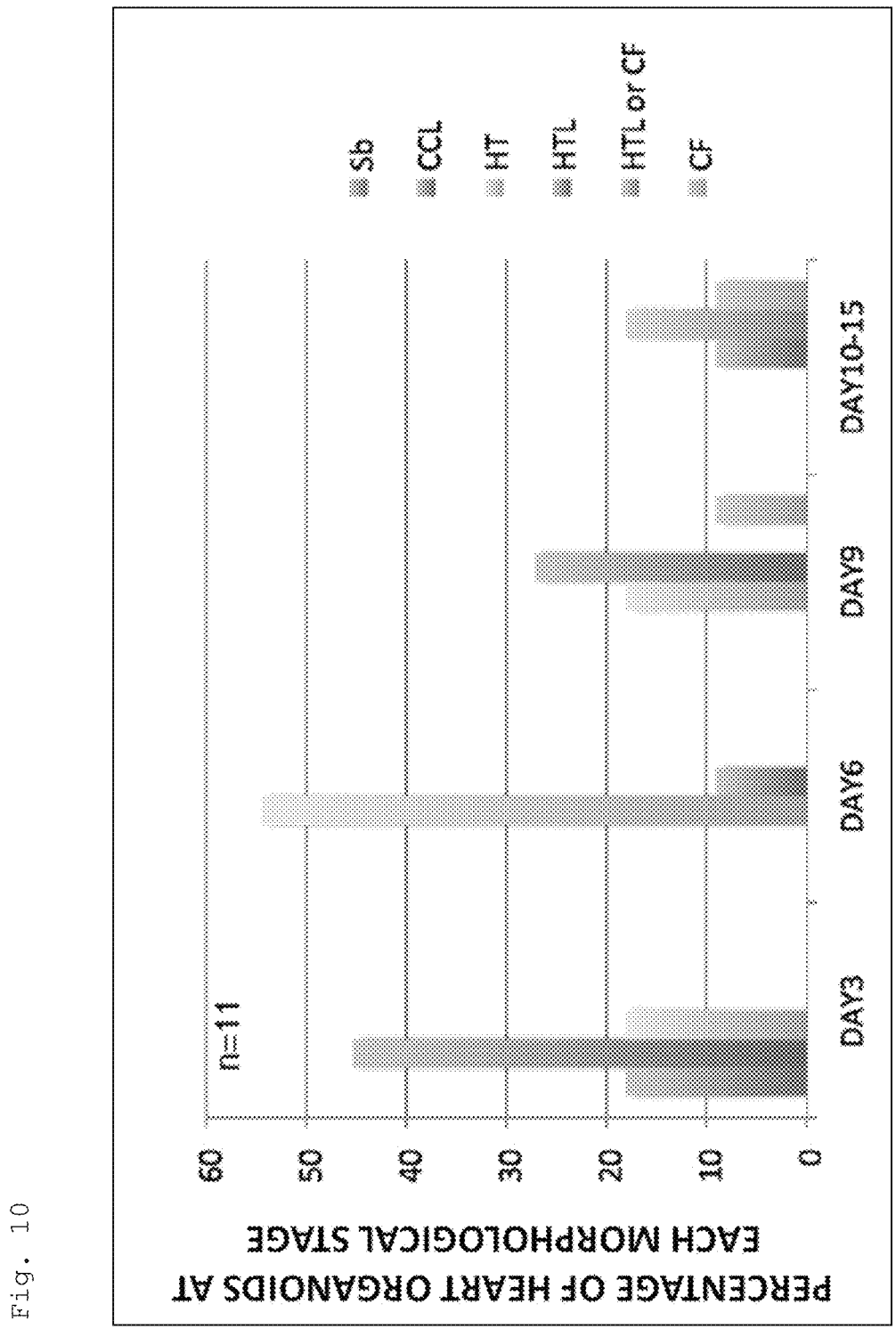
FIG. 10 is a graph showing the frequency of heart organoids with morphological features in the process of producing heart organoids of the present invention using 500 mouse ES cells. The notation in the figure is the same as that in FIG. 7.
Figure 11:
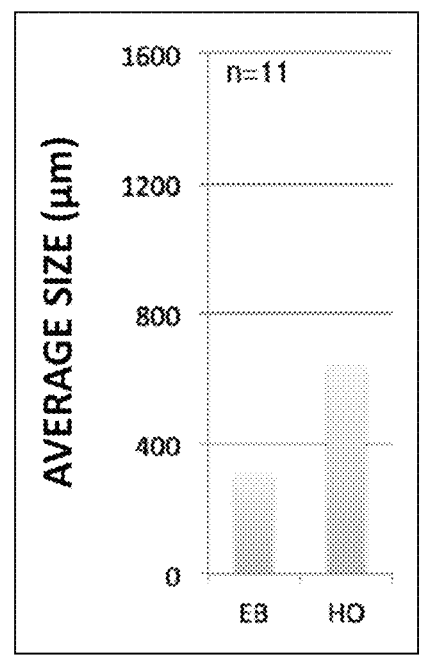
FIG. 11 is a graph showing the average sizes of embryoid bodies (EB) and HO (heart organoids) in the process of producing heart organoids of the present invention using 500 mouse ES cells. Note that the size indicates the average value of each major axis.

As a result, as shown in FIGS. 9 to 11, the size and beating ability of the obtained heart organoids were significantly reduced, and the number of heart organoids in the later morphogenetic steps (the stages of forming a looping heart tube and a cardiac chamber) was also reduced. From this, it is conceivable that a decrease in the number of cardiomyocytes caused a deficiency in morphogenesis, reducing beating.

Example 2

\<Detection of Cardiac Cell-Specific Marker in Heart Organoid\>

Next, morphological analysis was performed to determine whether cardiac-specific transcription factors and cardiac structural genes required for embryonic heart formation in heart organoids were to be properly expressed in these organoids (n=25).

Note that the T-box protein (Tbx5) is indispensable in early cardiac development, particularly in myocardial differentiation. In addition, it is known that the deletion of Tbx5 causes incomplete myocardial morphogenesis. Moreover, Tbx5 functions in coordination with zinc finger transcription factors and the GATA family to activate cardiac marker genes.

Figure 12:
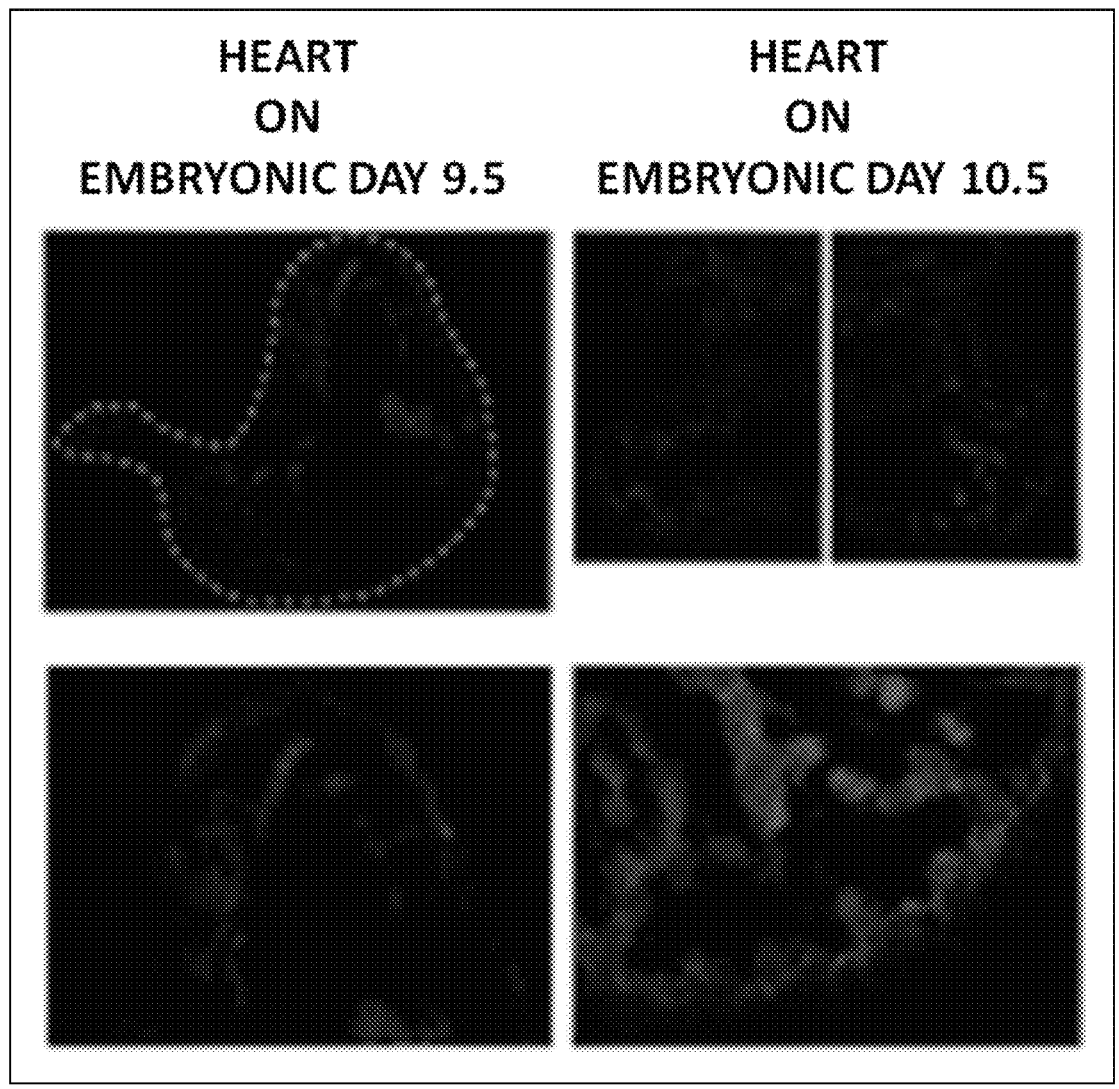
FIG. 12 is a photomicrograph showing the results of detecting the expression of PECAM and Tbx5 in mouse embryonic hearts (embryonic days 9.5 and 10.5) by immunofluorescent staining. In the figure, the expression of Tbx5 is shown in green, and the expression of PECAM is shown in red. In addition, the result of counterstaining with DAPI is shown in blue.
Figure 13:
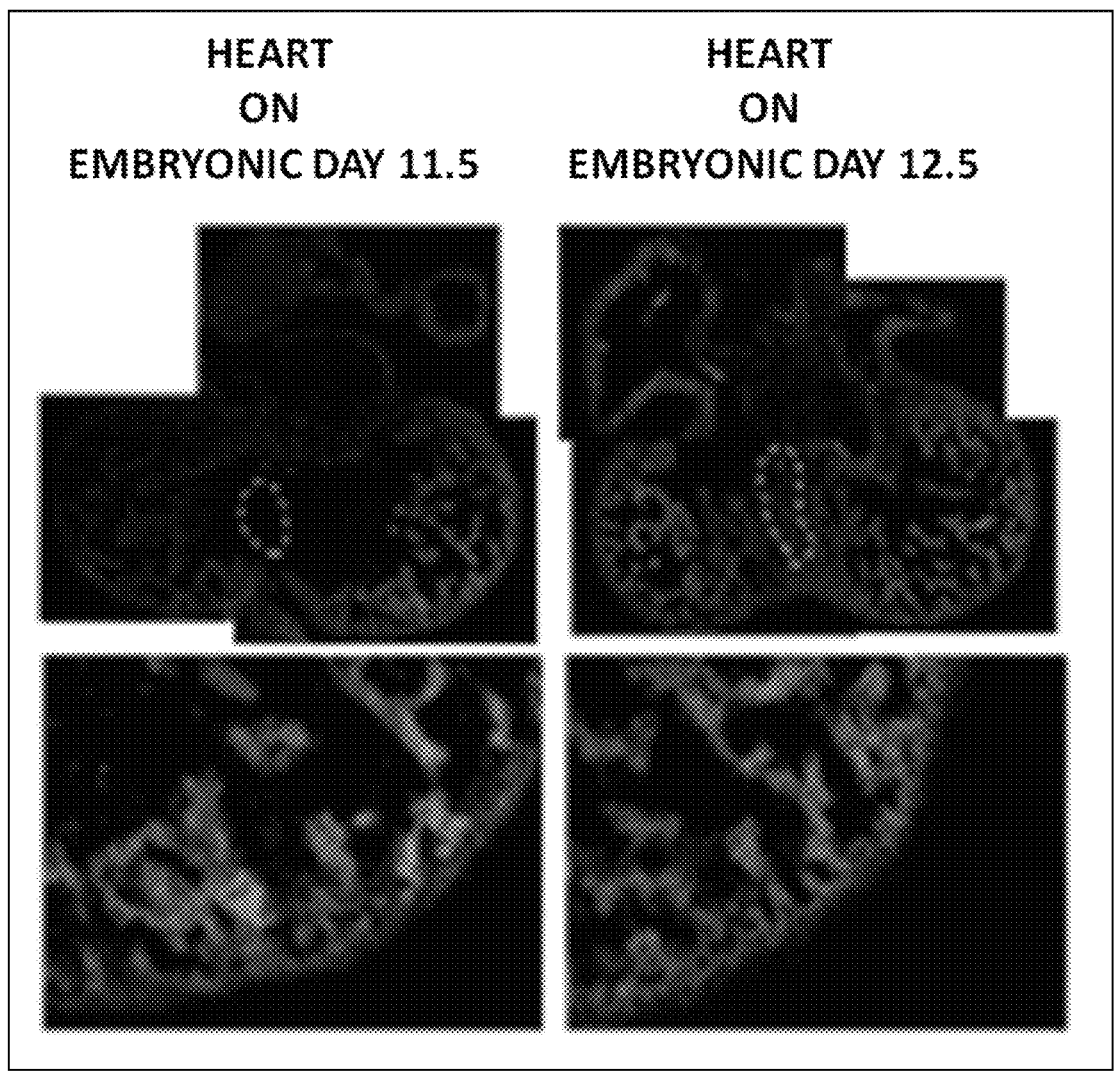
FIG. 13 is a photomicrograph showing the results of detecting the expression of PECAM and Tbx5 in mouse embryonic hearts (embryonic days 11.5 and 12.5) by immunofluorescent staining. In the figure, the expression of Tbx5 is shown in green, and the expression of PECAM is shown in red. In addition, the result of counterstaining with DAPI is shown in blue.

As shown in FIGS. 12 and 13, in vivo, Tbx5 is at an increased level on embryonic day 10.5 as compared with that of the heart on embryonic day 9.5, and continues to increase until embryonic day 12.5. Meanwhile, as shown in FIG. 14, an increase in Tbx5 expression was also observed in, for example, heart organoids on days 10 to 15 of culture.

Moreover, interestingly, as shown in FIGS. 15 and 16, the specific pattern of Tbx5 expression in heart organoids resembled that of the embryonic heart in vivo after cardiac chamber formation. For example, the expression of Tbx5 was positive in the left atrium, right atrium, and left ventricle derived from the first heart field, and was negative in the right ventricle derived from the second heart field.

In addition, as shown in FIG. 14, the segregated expression of platelet/endothelial cell adhesion molecule-1 (PECAM) was detected in most heart organoids. Specifically, expression of a representative EC marker was observed in inner membranes in primitive heart tubes and in vascular endothelial cells in multi-chambered heart organoids.

Furthermore, as a result of detecting the expression of SM-MHC, the expression of the marker revealed that the heart organoids cultured in vitro had cardiac structural cells essential in a three-dimensional structure similar to the heart in vivo, as shown in FIGS. 15 and 16.

Next, for the purpose of determining whether the cardiomyocytes in heart organoids were mature and acquired regionality in terms of cardiomyocyte subtypes (for example, atrial chamber and ventricular chamber), the expression of the sarcomeric proteins myosin light chain 2 atrial (Mlc-2a) and myosin light chain 2 ventricular (Mlc-2v) in heart organoids was examined.

As a result, as shown in FIG. 17, Mlc-2v was dominantly expressed in most of the heart organoids, and weak expression of Mlc-2a was observed in only a few heart organoids.

These results revealed that the present culture system was an efficient system for inducing mature cardiomyocytes with region specificity, as well as in vivo development after embryonic day 10.5.

In addition, as shown in FIGS. 18 and 19, expression of Mlc-2a was observed in the entire heart on embryonic day 9.5 (looping heart tube), but was observed in the atria on embryonic day 10.5 after cardiac chamber formation. Meanwhile, expression of Mlc-2v was observed in the atria on embryonic day 10.5, and very strong expression of Mlc-2v was observed in the left ventricle on embryonic day 12.5.

Moreover, for the purpose of determining whether structurally diverse cardiac cells (such as cardiomyocytes, endothelial cells, and smooth muscle cells) were co-expressed in heart organoids, the expression of cardiac troponin I (CM marker expressed in striated muscle), PECAM (EC marker), and SM-MHC (SM marker) was examined.

As a result, as shown in FIGS. 20 to 23, similar to the hearts on embryonic days 11.5 and 12.5, segregated expression of these markers was observed in most of the organoids.

These results indicate that heart organoids can mimic the structural characteristics of the embryonic heart.

In addition, the filamentous expression patterns of cardiac troponin I detected in some heart organoids were detected in the ventricles on embryonic day 12.5, and were similar to the expression patterns of sarcomere in mature long striated muscles, suggesting an organoid function such as muscle contraction (see FIGS. 20 to 23).

Furthermore, as a result of analyzing other cardiac marker genes including α-smooth muscle actin (αSMA) which is a marker of smooth muscle and Nkx2-5 (homeodomain transcription factor indicating cardiac lineage), the stage-specific intensity and localization of αSMA expression in the heart organoids was similar to those in vivo (for example, weak expression was observed in the heart on embryonic day 12.5).

Additionally, as shown in FIGS. 24 and 25, the broad expression of Nkx2-5 in heart organoids was similar to the expression observed on embryonic days 10.5, 11.5, and 12.5.

Furthermore, for the purpose of evaluating whether undifferentiated stem cells remained in the heart organoids, an immunostaining assay was performed on Oct3/4, a marker of pluripotent stem cells.

As shown in FIGS. 26 and 27, as a result of comparison with the expression of Oct3/4 in embryoid bodies before culture, the expression of Oct3/4 was not observed in the heart organoids. This revealed that cell differentiation successfully proceeded during in-vitro culture.

In addition, in embryonic hearts and brain tissues, the expression of nestin, expressed as a marker for neural stem cells, was detected in some heart organoids and the heart on embryonic day 12.5. These results suggest that nestin-positive cells derived from neural crest cells (NCC) contribute to cardiac innervation and conduction through the cardiac autonomic nervous system.

Finally, for the purpose of determining whether heart organoids was able to form atria, heart organoids were produced using ES cells expressing GFP-αMHC only in the atria in a restricted manner (αMHC-GFP ESCs, see Nemer, M. et al., Cardiovasc Pathol 17, 48-54, doi: 10.1016/j.carpath.2007.06.005 (2008)).

Although not shown in the figure, as expected, it was possible to produce heart organoids having multi-chambered heart organoids by the above differentiation induction protocol, similarly to wild-type ES cells. In addition, these heart organoids shoed αMHC-GFP expression in a region-restricted manner, indicating that the organoids possessed the capacity for atria formation.

Example 3

<Detection of Functional Contraction in Heart Organoid>

An evaluation was made as to whether a particular cardiac function, such as calcium oscillation, was obtained when spontaneous beating was detected in heart organoids. Specifically, an intracellular calcium indicator was used to measure $Ca^{2+}$ levels, thereby analyzing complete 3D heart organoids without dissociation (n=10).

As a result, although not shown in the figure, a transient increase in free $Ca^{2+}$ concentration, indicating functional contraction of myocardium through calcium oscillation, was confirmed in these organoids.

Example 4

<Analysis of Heart Organoid by Transmission Electron Microscope>

For the purpose of transmission electron microscope (TEM) analysis, a 90 nm ultrathin section was prepared from each of the mouse hearts on embryonic days 10.5 and 11.5 and heart organoid. Next, double staining was performed with uranyl acetate and lead citrate, and observation and photographing were performed. FIG. 28 shows the obtained results.

As shown in FIG. 28, the microstructure analysis using a transmission electron microscope revealed that the heart organoid of the present invention contained a sarcomere structure including a Z band, and an intercalated disc (ID) which is a characteristic structure of cardiomyocytes (see the two photographs on the left of FIG. 28). In addition, it was confirmed that these microstructures were similar to the microstructures of the embryonic heart (see the two photographs on the right of FIG. 28).

Example 5

<Quantification of Cardiomyocyte by Flow Cytometry Analysis>

For the purpose of flow cytometry analysis, an embryoid body and heart organoids on days 8 and 12 after culture were each treated with collagenase (1 mg/ml) at 37° C. for 15 minutes, and then treated with TrpLE (manufactured by Gibco) at 37° C. for 10 to 15 minutes. Then, the embryoid body, the heart organoids, and the heart of a living body were each subjected to a pipetting treatment so as to be separated into individual cells. The cells thus prepared were treated with 4% PFA/PBS at 4° C. for 10 minutes and immobilized. Next, these cells were treated with an antibody (Alexa647-conjugated anti-cTnT antibody) diluted with 4% FBS/PBS/0.5% saponin at 4° C. for 30 minutes and stained. Then, the cells were subjected to analysis using FACS Aria II (manufactured by BD). As a result, as shown in FIG. 29, a significant increase in cTnT (cardiac troponin)-positive cardiomyocytes was 6 observed in the heart organoids.

Example 6

<Principal Component Analysis (PCA) Using RNA-Seq Data>

An embryoid body and heart organoids on days 9 and 13 after culture were collected, and frozen and stored fresh in liquid nitrogen. In addition, they were dissected at each developmental stage, and the obtained embryonic heart was also collected and frozen in the same manner as the embryoid body and the like. Then, total RNA was extracted from each of the frozen samples using AllPrep DNA/RNA Micro Kit (manufactured by QIAGEN) according to the protocol. Next, a library for RNA-seq analysis was prepared using KAPA Standard mRNA-Seq Kit (manufactured by KAPA Biosystems). The obtained library was subjected to sequencing by HiSeq 1500 (single end 50 bp reads with HiSeq SR Rapid Cluster Kit v2 and HiSeq Rapid SBS Kit v2, manufactured by Illumina). With respect to the obtained sequence data, Bowtie2 was used to perform mapping to a mouse reference genome sequence (GRCm38/mm10). Then, Bioconductor package DEGseq was used to determine the read number and RPKM value of each gene.

As a result, as shown in FIG. 30, in the principal component analysis using the RNA-seq data, it was confirmed that the similarity between the heart organoid and the living heart also increased for PC1, excluding the hemoglobin-related genes of PC1 (10 genes including Hbb-y, Hba-x, and Hbb-bh). In addition, as shown in FIG. 31, as a result of analysis of heat map and hierarchical clustering, similarity of expression pattern was observed in the heart on embryonic day 9.5, the heart on embryonic day 11.5, and the heart organoids in terms of genes having expression difference among those hearts and embryoid body. From these results, it was confirmed that the heart organoids showed gene expression close to that of a living heart as a whole only except that they contained no blood components.

Moreover, as shown in FIG. 32, genes having a difference in expression between the heart organoids and the embryoid body were developed on an MA plot based on the above RNA-seq data. As a result, 39 genes highly expressed in heart organoids (regulated P-value<0.01, log 2Fold-Change>5) were extracted, and 55 genes lowly expressed in heart organoids (regulated P-value<0.01, log 2Fold-Change<−5) were extracted. Then, GO (gene ontology) analysis was performed on these genes, and as a result, among the 39 highly expressed genes, 26 out of the top 30 GO terms were heart-related (see FIG. 33). On the other hand, among the 55 lowly expressed genes, the terms of the top 30 GO did not include heart-related ones (see FIG. 34). As described above, it was confirmed that a large number of heart-related genes were included in the group of genes highly expressed in heart organoids.

Example 7

<Confirmation of Conduction System in Heart Organoid>

In heart organoids, the expression of TRPM4 expressed with cardiac troponin T and Purkinje fiber was detected by immunofluorescent staining. Note that the immunofluorescent staining was performed in the same manner as the above (immunofluorescent staining) except that cTnT (ab8295) and TRPM4 (ABN418) were used as primary antibodies.

As a result, as shown in FIG. 35, the presence of Purkinje cells (TRPM4 positive) was observed in the heart organoid. Since these cells are stimulation conduction system cells responsible for ventricular contraction, it was confirmed that a conduction system was formed also in the heart organoid as in the living heart.

Example 8

<Confirmation of Mature Cells in Heart Organoid>

In the heart organoid, the expression of potassium channel iK1 was detected by immunofluorescent staining. Note that the potassium channel iK1 is necessary for increasing the rate of rise of the action potential and the rate of conduction, and is detected only in mature cardiomyocytes. In addition, the immunofluorescent staining was performed in the same manner as the above (immunofluorescent staining) except that KCNN4 (iK1, GTX54786) was used as the primary antibody.

As a result, as shown in FIG. 36, since iK1 expression was observed in a heart organoid, it was confirmed that the cardiomyocytes of the heart organoid were mature cells containing the potassium channel.

Example 9

<Confirmation of T-Tubule in Heart Organoid>

As a new evaluation standard (FDA) for cardiomyocytes used for cardiotoxicity tests, the T-tubule (Transverse tubule) is regarded as important. However, it has not been observed in human iPS-derived cardiomyocytes, which is problematic (see Yang, X. et al., Circ Res 114(3) 511-23 (2014)).

When a cardiomyocyte receives an excitation stimulus, a dihydropyridine receptor (DHPR, voltage-dependent L-type $Ca^{2+}$ channel) present in the T-tubule of the cells is activated. The activated receptor causes a small amount of $Ca^{2+}$ to flow into cells. Then, in response, the ryanodine receptor (RYR, $Ca^{2+}$ release channel) in the sarcoplasmic reticulum (SR) releases a large amount of $Ca^{2+}$ in the sarcoplasmic reticulum, causing muscle contraction (see Steven, O. M et al., Cell, 101, 365 to 376 (2000)).

Then, for the purpose of proving that the SR/T-tubule junction involved in such myocardial excitation/contraction exists in the heart organoid of the present invention, an attempt was made to detect the expression of RYR important in the structure by immunofluorescent staining. Immunofluorescent staining was performed in the same manner as described above (immunofluorescent staining) except that RYR (ab2868) was used as the primary antibody. As a result, as shown in FIG. 37, it was confirmed that the SR/T-tubule junction was present in the heart organoid.

Example 10

<Electrophysiological Evaluation of Heart Organoid>

For the purpose of electrophysiologically evaluating heart organoids, optical mapping was performed by the following method. Note that, as another electrophysiological evaluation method, there is an extracellular potential recording method using a multipoint planar electrode (MBA), but this method cannot predict arrhythmia. On the other hand, use of optical mapping makes it possible to show that not only spontaneous excitation and membrane potential but also the interval between waveforms changes irregularly, so that arrhythmia can also be predicted.

Optical mapping was performed using a high-speed CMOS camera system (MiCAM Ultima, Brainvision, Tokyo, Japan) according to the method described by Ihara et al. (J Vis Exp. 2018; (132): 56478) (See FIG. 38).

The heart organoid was subjected to a staining treatment for 15 minutes using 15 μM di-4-ANEPPS (voltage-sensitive dye, Wako, Tokyo, Japan). After washing with PBS, the organoid was incubated for 15 minutes with 30 μM blebbistatin (excitation/contraction uncoupler, Sigma-Aldrich, St. Louis, MO) to suppress motion artifacts. Then, after washing, the heart organoid was transferred to a glass bottom dish filled with Tyrode's solution (135 mM NaCl, 5.4 mM KCl, 1.8 mM $CaCl_2$, 0.53 mM $MgCl_2$, 0.33 mM $NaH_2PO_4$, 5.5 mM D-glucose, and 5.0 mM HEPES (pH 7.40, adjusted with aeration of NaOH and 100% $O_2$)), and subjected to optical mapping. The temperature was maintained at 37° C. during the optical mapping process. In addition, all-optical mapping was performed using a 5× objective lens at a spatial resolution of 20 μm×20 μm/pixel, and data sampling was performed between 2.0 msec and 5.0 msec. Finally, the obtained data was analyzed using BV analysis software (Brainvision).

As a result, as shown in FIG. 39, it was possible to observe spontaneous excitation and membrane potential of heart organoid by electrophysiological analysis using optical mapping. From these results, it was confirmed that heart organoids also have electrophysiological properties extremely close to those of the heart of a living body.

Example 11

<Evaluation of Drug Responsiveness of Heart Organoid>

As indicated above, the heart organoid of the present invention has a high degree of maturity. For this reason, it can be an effective material for cardiotoxicity tests and the like for evaluating drug safety. Therefore, for the purpose of confirming its effectiveness, a drug causing cardiac dysfunction was used to evaluate the responsiveness of a drug to heart organoids.

Specifically, first, $Ca^{2+}$ measurement was performed by the method described above (Ca Measurement) in the presence and absence (control) of 1 μM isoproterenol, which is an adrenergic β-receptor agonist. A 15-second recording (movie) was taken, and image analysis was performed to detect the change in the intensity (Y-axis) of the fluorescent signal with time (X-axis).

As a result, as shown in FIG. 40, it was confirmed that the addition of isoproterenol made it possible to shorten the Ca signal cycle (tachycardia-like) in heart organoids. Specifically, it was confirmed that the use of the heart organoid of the present invention made it possible to evaluate drug responsiveness in which muscle contraction is controlled by calcium transients.

Next, it was examined by optical mapping whether addition of the IKr blocker E4031 would cause a change in QT prolongation and action potential in the heart organoid of the present invention. Note that the procedure was performed according to the method described in Example 10 except that 1 μM E4031 was added to the heart organoid.

As a result, as shown in FIG. 41, it was confirmed that an arrhythmia-like entity was induced in heart organoid by the IKr blocker (irregular variation in waveform intervals). In other words, the use of optical mapping and the heart organoid of the present invention made it possible to predict arrhythmia.

Example 12

<Examination of Extracellular Matrix Constituent Protein in Heart Organoid Formation>

In the same manner as described above (Cell Culture), mouse ES cells were cultured in a low-binding U-bottom 96-well plate in the absence of leukemia inhibitory factor (LIF) to obtain complete embryoid bodies. Then, the resulting embryoid bodies were cultured in the presence of an exogenous Fgf signal (FGF4) on the surface of laminin 411 ((manufactured by Nippi Inc., iMatrix-411; purified product of integrin binding site (E8 section) of human laminin 411 protein)), laminin 221 (manufactured by Nippi Inc., iMatrix-221; purified product of integrin binding site (E8 section) of human laminin 221 protein), or a mixture of laminins 221 and 411 in equal amounts, containing components of the extracellular matrix (ECM) in the connective tissue. The coating of each laminin was performed at 10.7 μg/cm$^2$. The culture period of the embryoid bodies and medium exchange were also performed as described above (Cell Culture), and after the culture, the heart organoids were collected for further analysis such as immunofluorescent staining.

As described above, as a result of culturing embryoid bodies on various laminins for 13 days, formation of cardiac chamber was observed in 80% or more of the samples under any conditions, as shown in FIG. 42. However, the heart organoids obtained under laminin 411 conditions had morphological characteristics closer to those of the living heart than those under laminin 221 conditions.

Next, the heart organoids obtained above were analyzed by the method described above (immunofluorescent staining). As a result, as shown in FIG. 43, the expression of Mlc2a and Mlc2v was lower in the organoids cultured on the surface of laminin 221 than in the heart organoids cultured on the surface of laminin 411. In addition, in the organoids cultured on the mixture of laminins 221 and 411, the state was conspicuous where atrial type cardiomyocytes were not separated but scattered. On the other hand, in the heart organoids cultured on the surface of laminin 411, spatial separation of ventricular-type cardiomyocytes (Mlc2v-positive cells) and atrial-type cardiomyocytes (Mlc2a-positive cells) was observed.

Next, the expression of cardiac troponin T and TRPM4 which is expressed with Purkinje fiber in the heart organoids obtained above was detected by immunofluorescent staining. Note that the detection was carried out by the method described above (immunofluorescent staining) except that cTnT (ab8295) and TRPM4 (ABN418) were used as primary antibodies.

As a result, as shown in FIG. 44, the organoids cultured on the surface of laminin 221 had low expression of cardiac troponin T and TRPM4. On the other hand, in the heart organoids cultured on the surface of laminin 411, expression of cardiac troponin T and TRPM4 equivalent to that in the mouse heart (embryonic day 10.5) was observed. Moreover, an appropriate positional relationship between normal cardiomyocytes and Purkinje cells was also confirmed, suggesting the formation of a conduction system.

From the above results, it is considered that laminin 411 contributes to self-organization that has acquired normal regionality in cardiac development.

Next, in addition to the expression of cardiac troponin T and TRPM4, the expression of Mlc2a expressed in atrial type myocardium and Mlc2v expressed in ventricular type myocardium was detected by immunofluorescent staining. As a result, in the expression of Mlc2a and Mlc2v, higher spatial segregation was observed depending on the sample in the heart organoids cultured on the surface of laminin 411 than in the heart organoids cultured on the LN/ET complex containing laminin 111, as shown in FIG. 45.

In addition, as mentioned in the above <Formation of Heart Organoid>, the results of the reanalysis of serial microarray data in the mouse embryonic heart revealed that laminin α1 showed the highest expression in the early stage of development, and laminin α4 showed the highest expression on embryonic day 14.5 at the time of separation (maturation of embryonic heart), although not shown in the figure.

Therefore, for the purpose of facilitating the production and long-term culture of mature heart organoids, an attempt was made to change the extracellular matrix during the culture. Specifically, first, in the same manner as described above (Cell Culture), mouse ES cells were cultured in a low-binding U-bottom 96-well plate in the absence of leukemia inhibitory factor (LIF) to obtain complete embryoid bodies. Then, the resulting embryoid bodies were cultured for 10 days in the presence of an exogenous Fgf signal (FGF4) on the surface of laminin 111-entactin (LN/ET complex) containing components of the extracellular matrix (ECM) in the connective tissue. Thereafter, the heart organoids were transferred onto a chamber slide coated with laminin 411 (0.5 µg/cm$^2$) or a mixture of laminin 411 and laminin 111, and the culture was continued until day 21 to observe their morphology under a microscope. Note that exchange of the medium of the embryoid bodies was performed as described above (Cell Culture) except for adding BMP4 (10 ng/mL), FGF4 (30 ng/mL), and LIF (1000 units/mL) from day 9 of culture.

As a result, as shown in FIG. 46, it was confirmed that it was possible to culture these heart organoids for at least 21 days. In addition, in these heart organoids, morphological changes were observed with beating.

Example 13

<Formation of Heart Organoid and Lung Organoid Using Human iPS Cells>

It was confirmed by the following method that it was possible to form heart organoids even when human iPS cells were used instead of the mouse ES cells described above.

As shown in FIG. 47, in the same manner as described above, human iPS cells (253G1 (Riken BRC # HPS0002) were cultured in a low-binding U-bottom 96-well plate in the absence of LIF to obtain embryoid bodies. Then, the resultant embryoid bodies were cultured on the surface of a gelated LN/ET complex under the conditions presented in the following table, that is, in the presence of FGF4 (conditions I, II, and IV) or in the presence of FGF4 and Y27632 (ROCK inhibitor) (condition III). On day 11 of culture, the cells were transferred to a new culture device and the culture was continued.

TABLE 1

| Condition | Experiment Count | Additive to Medium (Concentration) |
| --- | --- | --- |
| I | n = 29 | FGF4 (60 ng/mL) |
| II | n = 8 | FGF4 (30 ng/mL) |
| III | n = 28 | FGF4 (60 ng/mL), Y27632 (10 µM) |
| IV | n = 6 | FGF4 (100 ng/ml) |

As a result, it was possible to obtain a mouse heart organoid-like morphology in culture for 13 to 20 days. Moreover, it was possible to produce an organoid exhibiting a fetal period lung-like morphology.

It is not clear why the heart organoid and the lung organoid were produced at the same time as described above, but the present inventors speculate as follows.

For example, in mouse fetal development, lung development is known to begin with trachea formation on embryonic days 9.5 to 10 (fetal period) and end on embryonic day 12.5. Important points for lung development are branching morphogenesis and epithelial organization. Structural changes taking place during lung development are controlled by the expression of genes different at the proximal and terminal. As shown in the first row of FIG. 48, the heart on embryonic day 10.5 has completed the formation of two atria and two ventricles, but the lungs are in close contact with the heart while keeping the form of small tissues connected to the trachea, and their development is delayed in initial timing as compared with the development of the heart. In addition, as shown in the second and third rows of FIG. 48, since the size of the lungs increases rapidly on embryonic days 11.5 and 12.5, the differentiation of lung tissues and the division of cells become active in this period. In particular, Fgf10 and Shh (Sonic hedgehog) promote branching of the primitive lungs. Therefore, as described above, in vitro, it is considered that the FGF signal induced not only heart development but also lung development simultaneously.

In addition, as shown in FIG. 49 and FIG. 50, among the above conditions I to IV, the conditions with high efficiency of producing heart organoids and lung organoids (combined heart and lung, separated heart and lung) were condition II (62.5%) and condition III (60.7%). From this, it has been clarified that it is possible to produce heart-lung organoids simultaneously by limiting the concentration of FGF and by the action of the ROCK inhibitor.

Next, morphological analysis was performed as in the case of the mouse heart organoid described above to determine whether cardiac-specific transcription factors and cardiac structural genes required for embryonic heart formation were to be properly expressed in the human iPS cell-derived heart organoids obtained above. FIGS. 51 to 53 show the obtained results.

As shown in FIG. 51, in the human iPS cell-derived heart organoids, the expression of cardiac factors Tbx5 and Nkx2-5 was observed. In addition, as shown in FIG. 52, the expression of Mlc-2v, which is a mature ventricular marker, was also observed. Moreover, the expression of cardiac troponin I was observed in all human iPS cell-derived heart organoids examined, and the expression of PECAM was observed in some heart organoids (see FIG. 53).

In addition, histological analysis was performed as in the case of the heart organoids described above to determine whether the genes expressed in epithelial cells constituting the lung were to be properly expressed in the human iPS cell-derived lung organoids obtained above. Note that the analysis was performed in the same manner as described above (immunofluorescent staining) except that ECAD (ab11512) and CK8 (ab53280) were used as primary antibodies. FIG. 54 shows the obtained results.

It is known that the alveoli, which are an important structure of the lung, are surrounded by an alveoli wall composed of the type I alveoli cells and type II alveoli cells being epithelial cells.

On the other hand, as shown in FIG. 54, the expression of E cadherin (ECAD; co-localized with SFTPC, a type II alveoli cell, and expressed in the alveoli), an epithelial marker, and Cytokeratin 8 (CK8), a type II alveoli cell marker, was observed in the lung organoid of the present invention. The type II alveoli cells can also differentiate into type I alveoli cells with self-renewal. For this reason, it was suggested that the type I alveoli cells could potentially exist in the alveoli of the lung organoid of the present invention. In addition, in the lungs of a mouse fetus, the alveoli walls are organized in the alveoli by epithelial cells expressing ECAD and CK8. Similarly, in lung organoids, epithelial organization of alveolus-like portions was observed. That is, in the lung organoid of the present invention, an alveolar structure showing morphological similarity was observed.

As described above, it has been confirmed that the method of the present invention makes it possible to produce heart organoids regardless of the type of pluripotent stem cells (ES cells, iPS cells, and the like) and their origins (mouse, human, and the like). In addition, it has also been clarified that the method of the present invention makes it possible to produce a lung organoid having an alveolar structure.

INDUSTRIAL APPLICABILITY

As explained above, it has been clarified that, by culturing an embryoid body on the surface of a gel containing a cell-adhesive protein, it is possible to mimic the in vivo process of developing the heart exhibiting a unique spatial and temporal behavior with high self-forming ability. In short, the present invention has made it possible to produce heart organoids containing at least cardiomyocytes, endothelial cells, and smooth muscle cells.

In addition, the heart organoids thus obtained exhibited within a short culture period the same structural and functional characteristics as the in vivo counterpart, such as expression of transcription factors and structural proteins in the heart, region-specific expression of various types of cardiac cells, functional calcium oscillations, and electrophysiological properties.

Moreover, the present invention makes it possible to produce lung organoids. Besides, the lung organoids thus obtained have alveoli, which are an important structure responsible for the function of the lung.

Therefore, the heart organoid and lung organoid of the present invention reproduce their structures and functions in vivo, and thus are useful in regenerative medicine, pharmaceutical development, safety testing, and the like.

The invention claimed is:

1. A method for producing a heart organoid, consisting of the steps of:
    (a) culturing an embryoid body, on a surface of a gel containing an extracellular matrix constituent protein, in a medium comprising growth factors consisting of a fibroblast growth factor (FGF) protein, an insulin, a transferrin, and a selenite; and followed by
    (b) culturing the embryoid body in a medium comprising growth factors consisting of an FGF protein, a glycogen synthase kinase-3 (GSK-3) inhibitor, a bone morphogenic protein 4 (BMP4) protein, an insulin, a transferrin, a selenite, and a leukemia inhibitor factor (LIF),
    wherein
    the extracellular matrix constituent protein of (a) is laminin 111 or laminin 411; the FGF protein in steps (a) and (b) is an FGF2 protein or an FGF4 protein; and the heart organoid is a functional heart organoid with a conduction system.

2. The method for producing a heart organoid according to claim 1, wherein the embryoid body is a cell mass obtained by suspension culture of pluripotent stem cells in the absence of LIF protein.

3. A method for producing a heart organoid, consisting of the step of
    culturing an embryoid body on a surface of a gel containing an extracellular matrix constituent protein complex, in
    a medium comprising growth factors consisting of a fibroblast growth factor (FGF) protein, an insulin, a transferrin, and a selenite; or
    a medium comprising growth factors consisting of an FGF protein, an insulin, a transferrin, and a selenite, and a Rho-binding kinase inhibitor,
    wherein the extracellular matrix constituent protein complex comprises laminin 111 and entactin; the FGF protein is an FGF4 protein; and the heart organoid is a functional heart organoid with a conductive system.

* * * * *